(12) United States Patent
Lee et al.

(10) Patent No.: US 11,513,127 B2
(45) Date of Patent: Nov. 29, 2022

(54) METHODS FOR ASSAYING T-CELL DEPENDENT BISPECIFIC ANTIBODIES

(71) Applicant: Genentech, Inc., South San Francisco, CA (US)

(72) Inventors: Ho Young Lee, South San Francisco, CA (US); Guoying Jiang, South San Francisco, CA (US); Pin Yee Wong, South San Francisco, CA (US); Kendall Carey, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 746 days.

(21) Appl. No.: 16/072,486

(22) PCT Filed: Jan. 25, 2017

(86) PCT No.: PCT/US2017/014974
§ 371 (c)(1),
(2) Date: Jul. 24, 2018

(87) PCT Pub. No.: WO2017/132279
PCT Pub. Date: Aug. 3, 2017

(65) Prior Publication Data
US 2020/0182882 A1    Jun. 11, 2020

Related U.S. Application Data

(60) Provisional application No. 62/286,862, filed on Jan. 25, 2016.

(51) Int. Cl.
| | |
|---|---|
| C07K 16/28 | (2006.01) |
| G01N 33/68 | (2006.01) |
| C12Q 1/66 | (2006.01) |
| G01N 33/50 | (2006.01) |
| G01N 33/574 | (2006.01) |
| C12N 9/38 | (2006.01) |

(52) U.S. Cl.
CPC ..... *G01N 33/6854* (2013.01); *C07K 16/2803* (2013.01); *C07K 16/2809* (2013.01); *C07K 16/2863* (2013.01); *C07K 16/2887* (2013.01); *C07K 16/2896* (2013.01); *C12N 9/2471* (2013.01); *C12Q 1/66* (2013.01); *C12Y 301/03001* (2013.01); *C12Y 305/02006* (2013.01); *G01N 33/505* (2013.01); *G01N 33/574* (2013.01); *C07K 2317/31* (2013.01)

(58) Field of Classification Search
None
See application file for complete search history.

(56) References Cited

U.S. PATENT DOCUMENTS

| | | |
|---|---|---|
| 4,676,980 A | 6/1987 | Segal et al. |
| 4,816,567 A | 3/1989 | Cabilly et al. |
| 5,208,020 A | 5/1993 | Chari et al. |
| 5,229,275 A | 7/1993 | Goroff |
| 5,500,362 A | 3/1996 | Robinson et al. |
| 5,534,615 A | 7/1996 | Baker et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,571,894 A | 11/1996 | Wels et al. |
| 5,573,905 A | 11/1996 | Lerner et al. |
| 5,587,458 A | 12/1996 | King et al. |
| 5,589,369 A | 12/1996 | Seidman et al. |
| 5,591,669 A | 1/1997 | Hodge |
| 5,591,828 A | 1/1997 | Bosslet et al. |
| 5,641,870 A | 4/1997 | Barker |
| 5,648,237 A | 7/1997 | Carter |
| 5,693,780 A | 12/1997 | Newman et al. |
| 5,712,374 A | 1/1998 | Kuntsmann et al. |
| 5,731,168 A | 3/1998 | Carter et al. |
| 5,789,199 A | 8/1998 | Joly et al. |
| 5,821,337 A | 10/1998 | Carter et al. |
| 5,840,523 A | 11/1998 | Simmons et al. |
| 10,690,678 B2 | 6/2020 | Carey |
| 2006/0067930 A1 | 3/2006 | Adams et al. |
| 2014/0088295 A1 | 3/2014 | Smith et al. |
| 2015/0203579 A1 | 7/2015 | Papadopoulos |
| 2016/0169869 A1* | 6/2016 | Cong .................. A61K 38/1774 435/325 |
| 2017/0101472 A1* | 4/2017 | Ullman ................... A61P 31/12 |

(Continued)

FOREIGN PATENT DOCUMENTS

| | | |
|---|---|---|
| EP | 0 308 936 A2 | 9/1988 |
| EP | 0 404 097 B1 | 9/1996 |
| JP | 2006508163 A | 3/2006 |

(Continued)

OTHER PUBLICATIONS

ThermoFisher Scientific, "Luciferase Reporters," pp. 1-7, retrieved from the internet on Feb. 1, 2016. (Year: 2016).*
Zhou et al. (Molecular Medicine Reports, 12: 147-154, 2015). (Year: 2015).*
Promega, pNL3.2.NF-κB-RE[NlucP/NF-κB-RE/Hygro] Vector, pp. 1-2, Sep. 2016. (Year: 2016).*
Stieglmaier et al. (Expert Opinion on Biological Therapy, 15:8, 1093-1099, 2015). (Year: 2015).*
Nagorsen et al. (Pharmacology & Therapeutics 136 (2012) 334-342). (Year: 2012).*
Jutz et al. (Journal of Immunological Methods 430 (2016) 10-20). (Year: 2016).*
Frankel et al. (Current Opinion in Chemical Biology 2013, 17:385-392). (Year: 2013).*

(Continued)

*Primary Examiner* — Zachary S Skelding
(74) *Attorney, Agent, or Firm* — Morrison & Foerster LLP

(57) ABSTRACT

The present invention provides a cell-based assay for measuring T cell activation mediated by a T cell-dependent bispecific antibody (TDB). In some aspects, the assay is useful for detecting a TDB in a composition, quantitating the amount of TDB in a composition, determining the potency and/or specificity of a TDB, or determining if a population of cells expresses a target antigen. Compositions and kits are also contemplated.

14 Claims, 15 Drawing Sheets

Specification includes a Sequence Listing.

(56) References Cited

U.S. PATENT DOCUMENTS

| | | |
|---|---|---|
| 2018/0267055 A1 | 9/2018 | Carey |
| 2020/0378987 A1 | 12/2020 | Carey |

FOREIGN PATENT DOCUMENTS

| | | | |
|---|---|---|---|
| JP | 2015535828 A | 12/2015 | |
| WO | WO-1991/00360 A1 | 1/1991 | |
| WO | WO-1992/20373 A1 | 11/1992 | |
| WO | WO-1993/08829 A1 | 5/1993 | |
| WO | WO-1993/11161 A1 | 6/1993 | |
| WO | WO-1993/16185 A2 | 8/1993 | |
| WO | WO-1993/16185 A3 | 8/1993 | |
| WO | WO-1994/04690 A1 | 3/1994 | |
| WO | WO-1994/11026 A2 | 5/1994 | |
| WO | WO-1994/11026 A3 | 5/1994 | |
| WO | WO-1997/39722 A2 | 10/1997 | |
| WO | WO-2000/29004 A1 | 5/2000 | |
| WO | WO-2002/051870 A2 | 7/2002 | |
| WO | WO-2002/051870 A3 | 7/2002 | |
| WO | WO-2003/035694 A2 | 5/2003 | |
| WO | WO-2003/035694 A3 | 5/2003 | |
| WO | 2004050828 A2 | 6/2004 | |
| WO | 2004050828 A3 | 12/2004 | |
| WO | WO-2005/035572 A2 | 4/2005 | |
| WO | WO-2005/035572 A3 | 4/2005 | |
| WO | 2014047231 A1 | 3/2014 | |
| WO | 2014128185 A1 | 8/2014 | |
| WO | 2015142314 A1 | 9/2015 | |
| WO | WO2016191750 A1 | 12/2016 | |
| WO | 2017062888 A1 | 4/2017 | |
| WO | WO-2018108759 A1 * | 6/2018 | ....... G01N 33/57484 |

OTHER PUBLICATIONS

Dong et al. (Infection and Immunity, Jan. 1999, p. 220-229). (Year: 1999).*

Cheng et al. Promega Poster: "Development of a Robust Reporter-based T cell Activation Assay for Therapeutic Biologics in Immunotherapy," May 2, 2014, 1 page. (Year: 2014).*

International Search Report for International Application No. PCT/EP2017/082112, published Mar. 19, 2018, pp. 1-5. (Year: 2018).*

Junttila et al. (Cancer Res; 74(19); pp. 5561-5571 and Supplementary pp. 1-9 (2014)). (Year: 2014).*

Anonymous: "T Cell Activation Bioassay (NFAT)," retrieved from https://nld.promega.com/-/media/files/resources/protocols/technical-manuals/101/t-cell-activation-bioassay-nfat-protocol.pdf, last visited Mar. 21, 2017.

Brennan. M. et al. "Preparation Of Bispecific Antibodies by Chemical Recombination Of Monoclonal Immunoglobulin $G_1$ Fragments," Science 229:81-83, (Jul. 5, 1985).

Brodeur, B.R. et al."Mouse-Human Myeloma Partners For The Production Of Heterohybridomas,"in Monoclonal Antibody Production Techniques and Applications, pp. 51-63 Marcel Dekker, Inc., New York, (1987).

Brogan, J, et al. "Imaging Molecular Pathways: Reporter Genes," Radiat. Res. 177(4):508-513, (Apr. 2012), 9 pages.

Brown, W.M. "Anti-CD3 Antibody MacroGenics Inc.," Curr. Opin Investig Drugs 7(4):381-388, (Apr. 2006).

Bruggermann, M. et al. "Designer Mice: The Production Of Human Antibody Repertoires In Transgenic Animals," Year in Immuno. 7:33-40, (1993).

Buhmann, R, et al. "Immunotherapy Of Recurrent B-Cell Malignancies After Allo-SCT With Bi20 (FBTA05), A Trifunctional Anti-CD3 × Anti-CD20 antibody and Donor Lymphocyte Infusion," Bone Marrow Transplant. 43(5):383-397, (2009, e-pub. Oct. 13, 2008).

Capel, P.J.A. et al. "Heterogeneity Of Human IgG Fc Receptors," Immunomethods 4:25-34 (1994).

Caron, P.C. et al. Engineered Humanized Dimerica Forms of IgG Are More Effective Antibodies, J. Exp. Med. 176:1191-1195, (Oct. 1, 1992).

Carter, P. et al. "High Level Escherichia coli Expression and Production of a Bivalent Humanized Antibody Fragment," Biotech. 10:163-167, (Feb. 1992).

Carter, P. et al. "Humanization Of An Anti-p185$^{HER2}$ Antibody For Human Cancer Therapy," Proc. Natl. Acad. Sci. USA 89:4285-4289, (May 1992).

Chames, P. et al. "Bispecific antibodies for cancer therapy: The Light At The End Of The Tunnel?" 1(6):539-547, Nov./Dec. 2009, e-pub. Nov. 1, 2009).

Chan, J.K. et al. "Enhanced Killing of Primary Ovarian Cancer by Retargeting Autologous Cytokine-Induced Killer Cells with Bispecific Antibodies: A Preclinical Study," Clin Cancer Res. 12(6):1859-1867, Mar. 15, 2006).

Charlton, K.A. "Expression and Isolation Of Recombinant Antibody Fragments in E. coli," in Methods in Molecular Biology, vol. 248 B. K. C. Lo, ed, Humana Press, Totowa, N.1 , pp. 245-254, (2003).

Cheng, Z.-J.J. et al. "Development of a Robust Reporter-based T cell Activation Assay for Therapeutic Biologies in Immunotherapy," Poster, retrieved from <https://cdn.technologynetworks.com/TN/Resources/PDF/development-of-a-robust-reporter-based-t-cell-activation-assay-for-therapeutic-biologics-in.pdf>, last visited on Mar. 20, 2017.

Chothia, C. et al. "Canonical Structures For The Hypervariable Regions Of Immunoglobulins," J. Mol. Biol. 196:901-917, (1987).

Clackson, T. et al. "Making Antibody Fragments Using Phage Display Libraries," Nature 352:624-628, (Aug. 15, 1991).

Clynes, R. et al. "Fc Receptors Are Required in Passive and Active Immunity To Melanoma," Proc. Natl. Acad. Sci. USA 95:652-656, (Jan. 1998).

Cunningham, B.C. et al. "High-Resolution Epitope Mapping of hGH-receptor Interactions By Alanine-Scanning Mutagenesis," Science 244:1081-1085, (Jun. 2, 1989).

Daeron, M. "Fc Receptor Biology," Annu. Rev. Immunol. 15:203-234, (1997).

Davies, J. et al. "'Camelising' Human Antibody Fragments: NMR Studies On VH Domains," FEBS Lett. 339(3):285-290, (Feb. 1994).

De Gast, G.C. et al. "CD8 T cell Activation After Intravenous Administration Of CD3 × CD19 Bispecific Antibody In Patients With Non-Hodgkin Lymphoma," Cancer Immunol. Immunother. 40(6):390-396, (Jun. 1995).

De Haas, M. et al. "Fcγ Receptors of Phagocytes," J. Lab. Clin. Med. 126:330-341, (1995).

Dooley, M.F. et al. "Antibody Repertoire Development In Cartilaginous Fish," Dev Comp Immunol. 30(1-2):43-56, (2006).

Ferran, C. et al. "In Vivo T Cell Activation Properties Of Anti-T Cell Monoclonal Antibodies," Exp. Nephrol. 1(2):83-89, (Mar.-Apr. 1993).

Fournier, P. et al. "Bispecific Antibodies and Trispecific Immunocytokines For Targeting The Immune System Against Cancer: Preparing For The Future," BioDrugs 27(1):35-53, (2013, e-pub. Dec. 21, 2012).

Gazzano-Santoro, H. et al. "A Non-Radioactive Complement-Dependent Cytotoxicity Assay For Anti-CD20 Monoclonal Antibody," J. Immunol. Methods 202:163-171, (1997).

Goding, J.W. Monoclonal Antibodies: Principles and Practice pp. 59-103, (1983).

Griffiths, A.D. et al. "Human Anti-Self Antibodies With High Specificity From Phage Display Libraries," EMBO J. 12(2):725-734, (1993).

Gruber, M. et al. "Efficient Tumor Cell Lysis Mediated By a Bispecific Single Chain Antibody Expressed in Escherichia coli," J. Immunol. 152:5368-5374, (1994).

Guyer, R.L. et al. "Immunoglobulin Binding By Mouse Intestinal Epithelial Cell Receptors," J. Immunol. 117(2):587-593, (Aug. 1976).

Holliger, P. et al. "Diabodies: Small Bivalent and Bispecific Antibody Fragments," Proc. Natl. Acad. Sci. USA 90:6444-6448, (Jul. 1993).

Holt, L.J. et al. "Domain Antibodies: Proteins For Therapy," Trends Biotechnol. 21(11):484-490, (Nov. 2003).

Jakobovits, A. et al. "Germ-Line Transmission and Expression of a Human-Derived Yeast Artificial Chromosome," Nature 362:255-258, (Mar. 18, 1993).

(56) References Cited

OTHER PUBLICATIONS

Jakobovits, A. et al. "Analysis of Homozygous Mutant Chimeric Mice: Deletion of the Immunoglobulin Heavy-Chain Joining Region Blocks B-cell development and antibody production," *PNAS* 90:2551-2555, (Mar. 1993).

Jiang, G.et al. "Evaluation Of Semi-Homogeneous Assay Formats For Dual-Specificity Antibodies", *Journal Of Immunological Methods.* 387(1-2):51-56, (2013, e-pub. Oct. 9, 2012).

Johnson, K.S. et al. "Human Antibody Engineering," *Current Opinion in Structural Biology* 3:564-571, (1993).

Jones, P.T. et al. "Replacing the Complementarity—Determining Regions in a Human Antibody With Those From a Mouse," *Nature* 321:522-525, (May 29, 1986).

Kim, J.K., et al. "Localization of the Site of the Murine IgG1 Molecule That Is Involved in Binding To the Murine Intestinal Fc Receptor," *J. Immunol.* 24:2429-2434, (1994).

Klieger, Y. et al. "Unique Z-Chain Motifs Mediate a Direct TCR-Actin Linkage Critical For Immunological Synapse Formation and T-Cell Activation," 2014, *Eur. J. Immunol.* 44(1):58-68.

Kohler, G. et al. "Continuous Cultures of Fused Cells Secreting Antibody of Predefined Specificity," *Nature* 256:495-497, (Aug. 7, 1975).

Kostelny, S.A. et al. "Formation of a Bispecific Antibody By the Use of Leucine Zippers," *J. Immunol.* 148(5):1547-1553, (Mar. 1, 1992).

Kozbor, D. "A Human Hybrid Myeloma For Production of human Monoclonal Antibodies," *J. Immunol.* 133(6):3001-3005, (Dec. 1984).

Krogsgaard, M. et al. "Linking Molecular and Cellular Events In T-Cell Activation and Synapse Formation," *Semin. Immunol.* 15(6):307-315, (Dec. 2003).

Lehninger, A.L. *Biochemistry 2nd ed.*, pp. 73-75, Worth Publishers, New York, (1975).

Marks, J.D. et al. "By-passing immunization. Human Antibodies From V-Gene Libraries Displayed On Phage," *J. Mol. Biol.* 222:581-597, (1991).

Marks, J.D. et al. "By-Passing Immunization: Building High Affinity Human Antibodies by Chain Shuffling," *Bio/Technology* 10:779-783, (Jul. 1992).

McCafferty, J. et al. "Phage Antibodies: Filamentous Phage Displaying Antibody Variable Domains," *Nature* 348:552-554, (Dec. 6, 1990).

Milstein, C. "Hybrid Hybridomas and Their Use In Immunohistochemistry," *Nature* 305:537-540, (Oct. 6, 1983).

Miraglia, L.J. et al. "Seeing the Light: Luminescent Reporter Gene Assays," *Comb Chem. & High Throughput Screening* 14(8):648-657, (2011).

Morimoto, K. et al. "Single-Step Purification Of F(ab')2 fragments Of Mouse Monoclonal Antibodies (Immunoglobulins G1) by Hydrophobic Interaction High Performance Liquid Chromatography Using TSKgel Phenyl-5PW," *J. Biochem. And Biophysical Methods* 24:107-117, (1992).

Morrison, S.L. et al. "Chimeric Human Antibody Molecules: Mouse Antigen-Binding Domains With Human Constant Region Domains," *Proc. Natl. Acad. Sci. USA* 81:6851-6855, (Nov. 1984).

Munson, P.J. et al. "Ligand: A Versatile Computerized Approach For Characterization Of Ligand-Binding Systems," *Anal. Biochem.* 107:220-239, (1980).

Muyldermans, S. et al. "Recognition Of Antigens By Single-Domain Antibody Fragments: The Superfluous Luxury Of Paired Domains," *Trend Biochem. Sci.* 26(4):230-235, (Apr. 2001).

Nakajima, Y. et al. "Bioluminescence assays: Multicolor Luciferase Assay, Secreted Luciferase Assay and Imaging Luciferase Assay," *Expert Opin Drug Dzscovery*, 5(9):835-849, 2010.

Nakamura, G.R. et al. "Strain Specificity and Binding Affinity Requirements Of Neutralizing Monoclonal Antibodies to The C4 Domain Of gp120 From Human Immunodeficiency Virus Type 1," *J. Virol.* 67(10):6179-6191, (Oct. 1993).

Naldini, L. et al. "In Vivo Gene Delivery and stable Transduction Of Nondividing Cells By a Lentiviral Vector," *Science* 272(5259):263-267, (Apr. 12, 1996).

Osaka, G. et al. "Pharmacokinetics, Tissue Distribution, And Expression Efficiency Of Plasmid 32P-DNA Following Intravenous Administration Of DNA/Cationic Lipid Complexes In Mice: Use Of A Novel Radionuclide Approach," *J. Pharm. Sci.* 85:612-618, (Jun. 1996).

Pardo, J, et al. "Differential implication Of Protein Kinase C Isoforms In Cytotoxic T Lymphocyte Degranulation And TCR-Induced Fas Ligand Expression," *Int. Immunol.* 15(12):1441-1450, (Dec. 2003).

Parekh, B.S. et al. "Development and Validation Of An Antibody-Dependent Cell-Mediated Cytotoxicity-Reporter Gene Assay," *mAbs* 4(3):310-318, (May/Jun. 2012).

Pattu, V. et al. "In The Crosshairs: Investigating Lytic Granules By High-Resolution Microscopy And Electrophysiology," *Front. Immunol.* 4(411):1-8, (Nov. 27, 2013).

Pipkin, M.E. et al. "The Transcriptional Control Of The Perforin Locus," *Immunol Rev.* 235(1):55-72, (May 2010), 30 pages.

Pluckthun, A. "Mono- and Bivalent Antibody Fragments Produced In *Escherichia coli*: Engineering, Folding and Antigen Binding," *Immunol. Revs.* 130:151-188 (1992).

Pluckthun, A. "Antibodies From *Escherichia coli*," in *The Pharmacology of Monoclonal Antibodies*, vol. 113, Rosenburg and Moore eds., Springer-Verlag, New York, pp. 269-315, (1994).

Pores-Fernando, A.T. et al. "Calcium Influx and Signaling In Cytotoxic T-Lymphocyte Lytic Granule Exocytosis," *Immunol. Rev.* 231(I):160-173, (Sep. 10, 2009).

Presta, L.G. et al. "Antibody Engineering," *Curr. Op. Struct. Biol.* 2:593-596, (1992).

Presta, L.G. et al. "Humanization Of An Antibody Directed Against IgE" *J. Immunol.* 151(5):2623-2632, (Sep. 1, 1993).

Ravetch, J.V. et al. "Fc Receptors," *Annu. Rev. Immunol.* 9:457-492, (1991).

Riechmann, L. et al. "Reshaping Human Antibodies For Therapy," *Nature* 332:323-329, (1988).

Schwartz, J.C. et al. "Structural Mechanisms Of Costimulation," *Nat. Immunol.* 3(5):427-434, (May 2002).

Shannon, M.F. et al. "GM-CSF and IL-2 Share Common Control Mechanisms In Response To Costimulatory Signals In T Cells," *J. Leukoc. Biol.* 57:767-773, (May 1995).

Shapiro, V.S.et al. "Cutting Edge: Nuclear Factor Of Activated T Cells and AP-1 Are Insufficient For IL-2 Promoter Activation: Requirement for CD28 Up-Regulation Of RE/AP," *The Journal of Immunology*, 161:6455-6458, (1998).

Shipkova, M. et al. "Surface Markers Of Lymphocyte Activation And Markers Of Cell Proliferation," *Clin. Chim. Acta* 413:1338-1349, (Sep. 8, 2012, e-Pub. Nov. 19, 2011).

Shopes, B. "A Genetically Engineered Human IgG Mutant With Enhanced Cyolytic Activity," *Immunol.* 148(9):2918-2922, (May 1, 1992).

Signosis: "NFAT Luciferase Reporter Stable Cell Line," retrieved from <http://www.signosisinc.com/images/uploaded/1439927240> last visited Mar. 20, 2017, 2 pages.

Sims, M.J. et al. "A Humanized CD18 Antibody Can Block Function Without Cell Destruction," *J. Immunol.* 151(4):2296-2308, (Aug. 15, 1993).

Skerra, A. "Bacterial Expression Of Immunoglobulin Fragments," *Curr. Opinion in Immunol.* 5:256-262 (1993).

Stecha, P. et al. "Abstract 5439: Development Of a Robust Reporter-Based T-Cell Activation Assay For Bispecific Therapeutic Antibodies In Immunotherapy," *Cancer Research* 75(15):Abstract 5439, (Aug. 2015), 3 pages.

Stevenson, G.T. et al. "A Chimeric Antibody With Dual Fc Regions (bisFabFc) Prepared By Manipulations At The IgG Hinge," *Anti-Cancer Drug Design* 3:219-230, (1989).

Suresh, M.R. et al. "Bispecific Monoclonal Antibodies From Hybrid Hybridomas," *Meth. In Enzymology* 121:210-228, (1986).

Svobodova, K. et al. "New In Vitro Reporter Gene Bioassays For Screening Of Hormonal Active Compounds In The Environment," *Appl. Microbiol. Biotechnol.* 88(4): 39-847, (Oct. 2010, e-pub. Aug. 25, 2010).

(56) References Cited

OTHER PUBLICATIONS

Traunecker, A. et al. "Bispecific Single Chain Molecules (Janusins) Target Cytotoxic Lymphocytes On HIV Infected Cells," *EMBO J.* 10(12):3655-3659, (1991).

Tutt, A. et al. "Trispecific F(ab')3 Derivatives That Use Cooperative Signaling Via The TCR/CD3 Complex and CD2 To Activate and Redirect Resting Cytotoxic T Cells," *J. Immunol.* 147(1):60-69, (Jul. 1, 1991).

Verhoeyen, M. et al. "Reshaping Human Antibodies: Grafting An Antilysozyme Activity," *Science* 239:1534-1536, (Mar. 25, 1988).

Vitetta, E.S. et al, "Redesigning Nature's Poisons to Create Anti-Tumor Reagents," Science, 238:1098-1104, (1987).

Ward, E.S. et al. "Binding Activities Of a Repertoire Of Single Immunoglobulin Variable Domains Secreted From *Escherichia coli*," *Nature* 341(6242):544-546, (Oct. 12, 1989).

Waterhouse, P. et al. "Combinatorial Infection and in vivo Recombination: A Strategy For Making Large Phage Antibody Repertoires," *Nuc. Acids. Res.* 21(9):2265-2266, (1993).

Wolff, E.A. et al. "Monoclonal Antibody Homodimers: Enhanced Antitumor Activity In Nude Mice," *Cancer Research* 53:2560-2565, (Jun. 1, 1993).

Zapata, G. et al. "Engineering Linear F(ab')$_2$ Fragments For Efficient Production In *Escherichia coli* and Enhanced Antiproliferative Activity," *Protein Eng.* 8(10):1057-1062, (1995).

Ziegler, S.F. et al. "The Activation Antigen CD69," *Stem Cells* 12(5):456-465, (Sep. 1994).

International Preliminary Report On Patentability, dated Jul. 31, 2018, for PCT Application No. PCT/US2017/014974, filed on Jan. 25, 2017, 8 pages.

International Search Report dated Apr. 7, 2017, for PCT Application No. PCT/US2017/014974, filed on Jan. 25, 2017, 6 pages.

Written Opinion dated Apr. 7, 2017, for PCT Application No. PCT/US2017/014974, filed on Jan. 25, 2017, 7 pages.

U.S. Appl. No. 16/874,550, filed May 14, 2020, for Carey, K.

Li, Y. (Mar. 31, 2015). "Regulatory Mechanisms of Signal Transduction in Antiviral Innate Immunity," Wuhan University Press, p. 51 with English Translation, 3 pages.

Sun, Z. et al. (Jan. 2014). "Clinical and Examination of Kidney Markers," People's Military Medical Press, p. 227 with English Translation, 4 pages.

Wang, D. et al. (Jan. 2004). "CD3/CD28 Costimulation Inducted NF kB Activation Is Mediated By Recruitment of Protein Kinase C-⊖, Bcl10, an IkB Kinase β to the Immunological Synapse Through CARMA1," Molecular and Cellular Biology 24(1):164-171.

\* cited by examiner

SEQUENCE LISTING

```
<160> NUMBER OF SEQ ID NOS: 40

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct

<400> SEQUENCE: 1

Asn Tyr Tyr Ile His
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic Construct

<400> SEQUENCE: 2

Trp Ile Tyr Pro Gly Asp Gly Asn Thr Lys Tyr Asn Glu Lys Phe Lys
1               5                   10                  15

Gly

<210> SEQ ID NO 3
```

```
<211> LENGTH: 10
<212> TYPE: PRT
<213> ORGANISM: Artificial Sequence
<220> FEATURE:
<223> OTHER INFORMATION: Synthetic Construct

<400> SEQUENCE: 3

Asp Ser Tyr Ser Asn Tyr Phe Asp Tyr
1               5                   10

<210> SEQ ID NO 4
<211> LENGTH: 17
<212> TYPE: PRT
<213> ORGANISM: Artificial Sequence
<220> FEATURE:
<223> OTHER INFORMATION: Synthetic Construct

<400> SEQUENCE: 4

Lys Ser Ser Gln Ser Leu Leu Asn Ser Arg Thr Arg Lys Asn Tyr Leu
1               5                   10                  15
Ala

<210> SEQ ID NO 5
<211> LENGTH: 7
<212> TYPE: PRT
<213> ORGANISM: Artificial Sequence
<220> FEATURE:
<223> OTHER INFORMATION: Synthetic Construct

<400> SEQUENCE: 5

Trp Ala Ser Thr Arg Glu Ser
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic Construct

<400> SEQUENCE: 6

Thr Gln Ser Phe Ile Leu Arg Thr
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic Construct

<400> SEQUENCE: 7

Ser Tyr Tyr Ile His
1               5

<210> SEQ ID NO 8
<211> LENGTH: 17
<212> TYPE: PRT
<213> ORGANISM: Artificial Sequence
<220> FEATURE:
<223> OTHER INFORMATION: Synthetic Construct

<400> SEQUENCE: 8

Trp Ile Tyr Pro Glu Asn Asp Asn Thr Lys Tyr Asn Glu Lys Phe Lys
1               5                   10                  15
Asp
```

<210> SEQ ID NO 9
<211> LENGTH: 10
<212> TYPE: PRT
<213> ORGANISM: Artificial Sequence
<220> FEATURE:
<223> OTHER INFORMATION: Synthetic Construct

<400> SEQUENCE: 9

Asp Gly Tyr Ser Arg Tyr Tyr Phe Asp Tyr
1               5                   10

<210> SEQ ID NO 10
<211> LENGTH: 17
<212> TYPE: PRT
<213> ORGANISM: Artificial Sequence
<220> FEATURE:
<223> OTHER INFORMATION: Synthetic Construct

<400> SEQUENCE: 10

Lys Ser Ser Gln Ser Leu Leu Asn Ser Arg Thr Arg Lys Asn Tyr Leu
1               5                   10                  15

Ala

<210> SEQ ID NO 11
<211> LENGTH: 7
<212> TYPE: PRT
<213> ORGANISM: Artificial Sequence
<220> FEATURE:
<223> OTHER INFORMATION: Synthetic Construct

<400> SEQUENCE: 11

Trp Thr Ser Thr Arg Lys Ser
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic Construct

<400> SEQUENCE: 12

Lys Gln Ser Phe Ile Leu Arg Thr
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic Construct

<400> SEQUENCE: 13

Gly Tyr Thr Met Asn
1               5

<210> SEQ ID NO 14
<211> LENGTH: 17
<212> TYPE: PRT
<213> ORGANISM: Artificial Sequence
<220> FEATURE:
<223> OTHER INFORMATION: Synthetic Construct

<400> SEQUENCE: 14

Leu Ile Asn Pro Tyr Lys Gly Val Ser Thr Tyr Asn Gln Lys Phe Lys

```
                1               5                  10                 15
Asp

<210> SEQ ID NO 15
<211> LENGTH: 13
<212> TYPE: PRT
<213> ORGANISM: Artificial Sequence
<220> FEATURE:
<223> OTHER INFORMATION: Synthetic Construct

<400> SEQUENCE: 15

Ser Gly Tyr Tyr Gly Asp Ser Asp Trp Tyr Phe Asp Val
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Synthetic Construct

<400> SEQUENCE: 16

Arg Ala Ser Gln Asp Ile Arg Asn Tyr Leu Asn
1               5                   10

<210> SEQ ID NO 17
<211> LENGTH: 7
<212> TYPE: PRT
<213> ORGANISM: Artificial Sequence
<220> FEATURE:
<223> OTHER INFORMATION: Synthetic Construct

<400> SEQUENCE: 17

Tyr Thr Ser Arg Leu Glu Ser
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic Construct

<400> SEQUENCE: 18

Gln Gln Gly Asn Thr Leu Pro Trp Thr
1               5

<210> SEQ ID NO 19
<211> LENGTH: 119
<212> TYPE: PRT
<213> ORGANISM: Artificial Sequence
<220> FEATURE:
<223> OTHER INFORMATION: Synthetic Construct

<400> SEQUENCE: 19

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Arg Gln Ala Pro Gly Gln Gly Leu Glu Trp Ile
        35                  40                  45

Gly Trp Ile Tyr Pro Gly Asp Gly Asn Thr Lys Tyr Asn Glu Lys Phe
    50                  55                  60

Lys Gly Arg Ala Thr Leu Thr Ala Asp Thr Ser Thr Ser Thr Ala Tyr
```

```
                65                  70                  75                  80
Leu Glu Leu Ser Ser Leu Arg Ser Glu Asp Thr Ala Val Tyr Tyr Cys
                        85                  90                  95

Ala Arg Asp Ser Tyr Ser Asn Tyr Tyr Phe Asp Tyr Trp Gly Gln Gly
                100                 105                 110

Thr Leu Val Thr Val Ser Ser
        115

<210> SEQ ID NO 20
<211> LENGTH: 112
<212> TYPE: PRT
<213> ORGANISM: Artificial Sequence
<220> FEATURE:
<223> OTHER INFORMATION: Synthetic Construct

<400> SEQUENCE: 20

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
                20                  25                  30

Arg Thr Arg Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Thr Gln
                85                  90                  95

Ser Phe Ile Leu Arg Thr Phe Gly Gln Gly Thr Lys Val Glu Ile Lys
                100                 105                 110

<210> SEQ ID NO 21
<211> LENGTH: 119
<212> TYPE: PRT
<213> ORGANISM: Artificial Sequence
<220> FEATURE:
<223> OTHER INFORMATION: Synthetic Construct

<400> SEQUENCE: 21

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
                20                  25                  30

Tyr Ile His Trp Val Arg Gln Ala Pro Gly Gln Gly Leu Glu Trp Ile
            35                  40                  45

Gly Trp Ile Tyr Pro Glu Asn Asp Asn Thr Lys Tyr Asn Glu Lys Phe
    50                  55                  60

Lys Asp Arg Val Thr Ile Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Gly Tyr Ser Arg Tyr Tyr Phe Asp Tyr Trp Gly Gln Gly
                100                 105                 110

Thr Leu Val Thr Val Ser Ser
        115

<210> SEQ ID NO 22
<211> LENGTH: 112
```

```
<212> TYPE: PRT
<213> ORGANISM: Artificial Sequence
<220> FEATURE:
<223> OTHER INFORMATION: Synthetic Construct

<400> SEQUENCE: 22

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Thr Ser Thr Arg Lys Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Ile Leu Arg Thr Phe Gly Gln Gly Thr Lys Val Glu Ile Lys
            100                 105                 110

<210> SEQ ID NO 23
<211> LENGTH: 122
<212> TYPE: PRT
<213> ORGANISM: Artificial Sequence
<220> FEATURE:
<223> OTHER INFORMATION: Synthetic Construct

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Thr Met Asn Trp Val Arg Gln Ala Pro Gly Lys Asp Leu Glu Trp Val
        35                  40                  45

Ala Leu Ile Asn Pro Tyr Lys Gly Val Ser Thr Tyr Asn Gln Lys Phe
    50                  55                  60

Lys Asp Arg Phe Thr Ile Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Tyr Gly Asp Ser Asp Trp Tyr Phe Asp Val Trp
            100                 105                 110

Gly Gln Gly Thr Leu Val Thr Val Ser Ser
        115                 120

<210> SEQ ID NO 24
<211> LENGTH: 107
<212> TYPE: PRT
<213> ORGANISM: Artificial Sequence
<220> FEATURE:
<223> OTHER INFORMATION: Synthetic Construct

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
```

```
                35                  40                  45
Tyr Tyr Thr Ser Arg Leu Glu Ser Gly Val Pro Ser Arg Phe Ser Gly
         50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Gln Gly Asn Thr Leu Pro Trp
                 85                  90                  95

Thr Phe Gly Gln Gly Thr Lys Leu Glu Leu Lys
            100                 105

<210> SEQ ID NO 25
<211> LENGTH: 10
<212> TYPE: PRT
<213> ORGANISM: Artificial Sequence
<220> FEATURE:
<223> OTHER INFORMATION: Synthetic Construct

<400> SEQUENCE: 25

Gly Tyr Thr Phe Thr Ser Tyr Asn Met His
 1               5                  10

<210> SEQ ID NO 26
<211> LENGTH: 17
<212> TYPE: PRT
<213> ORGANISM: Artificial Sequence
<220> FEATURE:
<223> OTHER INFORMATION: Synthetic Construct

<400> SEQUENCE: 26

Ala Ile Tyr Pro Gly Asn Gly Asp Thr Ser Tyr Asn Gln Lys Phe Lys
 1               5                  10                  15

Gly

<210> SEQ ID NO 27
<211> LENGTH: 13
<212> TYPE: PRT
<213> ORGANISM: Artificial Sequence
<220> FEATURE:
<223> OTHER INFORMATION: Synthetic Construct

<400> SEQUENCE: 27

Val Val Tyr Tyr Ser Asn Ser Tyr Trp Tyr Phe Asp Val
 1               5                  10

<210> SEQ ID NO 28
<211> LENGTH: 10
<212> TYPE: PRT
<213> ORGANISM: Artificial Sequence
<220> FEATURE:
<223> OTHER INFORMATION: Synthetic Construct

<400> SEQUENCE: 28

Arg Ala Ser Ser Ser Val Ser Tyr Met His
 1               5                  10

<210> SEQ ID NO 29
<211> LENGTH: 7
<212> TYPE: PRT
<213> ORGANISM: Artificial Sequence
<220> FEATURE:
<223> OTHER INFORMATION: Synthetic Construct

<400> SEQUENCE: 29

Ala Pro Ser Asn Leu Ala Ser
```

<210> SEQ ID NO 30
<211> LENGTH: 9
<212> TYPE: PRT
<213> ORGANISM: Artificial Sequence
<220> FEATURE:
<223> OTHER INFORMATION: Synthetic Construct

<400> SEQUENCE: 30

Gln Gln Trp Ser Phe Asn Pro Pro Thr
1               5

<210> SEQ ID NO 31
<211> LENGTH: 122
<212> TYPE: PRT
<213> ORGANISM: Artificial Sequence
<220> FEATURE:
<223> OTHER INFORMATION: Synthetic Construct

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Asn Met His Trp Val Arg Gln Ala Pro Gly Lys Gly Leu Glu Trp Val
        35                  40                  45

Gly Ala Ile Tyr Pro Gly Asn Gly Asp Thr Ser Tyr Asn Gln Lys Phe
    50                  55                  60

Lys Gly Arg Phe Thr Ile Ser Val Asp Lys Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Val Tyr Tyr Ser Asn Ser Tyr Trp Tyr Phe Asp Val Trp
            100                 105                 110

Gly Gln Gly Thr Leu Val Thr Val Ser Ser
        115                 120

<210> SEQ ID NO 32
<211> LENGTH: 107
<212> TYPE: PRT
<213> ORGANISM: Artificial Sequence
<220> FEATURE:
<223> OTHER INFORMATION: Synthetic Construct

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Ser Tyr Met
            20                  25                  30

His Trp Tyr Gln Gln Lys Pro Gly Lys Ala Pro Lys Pro Leu Ile Tyr
        35                  40                  45

Ala Pro Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Phe Asn Pro Pro Thr
                85                  90                  95

Phe Gly Gln Gly Thr Lys Val Glu Ile Lys Arg
            100                 105

```
<210> SEQ ID NO 33
<211> LENGTH: 5
<212> TYPE: PRT
<213> ORGANISM: Artificial Sequence
<220> FEATURE:
<223> OTHER INFORMATION: Synthetic Construct

<400> SEQUENCE: 33

Asp Thr Tyr Ile His
1               5

<210> SEQ ID NO 34
<211> LENGTH: 17
<212> TYPE: PRT
<213> ORGANISM: Artificial Sequence
<220> FEATURE:
<223> OTHER INFORMATION: Synthetic Construct

<400> SEQUENCE: 34

Arg Ile Tyr Pro Thr Asn Gly Tyr Thr Arg Tyr Ala Asp Ser Val Lys
1               5                  10                  15

Gly

<210> SEQ ID NO 35
<211> LENGTH: 11
<212> TYPE: PRT
<213> ORGANISM: Artificial Sequence
<220> FEATURE:
<223> OTHER INFORMATION: Synthetic Construct

<400> SEQUENCE: 35

Trp Gly Gly Asp Gly Phe Tyr Ala Met Asp Tyr
1               5                  10

<210> SEQ ID NO 36
<211> LENGTH: 11
<212> TYPE: PRT
<213> ORGANISM: Artificial Sequence
<220> FEATURE:
<223> OTHER INFORMATION: Synthetic Construct

<400> SEQUENCE: 36

Arg Ala Ser Gln Asp Val Asn Thr Ala Val Ala
1               5                  10

<210> SEQ ID NO 37
<211> LENGTH: 7
<212> TYPE: PRT
<213> ORGANISM: Artificial Sequence
<220> FEATURE:
<223> OTHER INFORMATION: Synthetic Construct

<400> SEQUENCE: 37

Ser Ala Ser Phe Leu Tyr Ser
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic Construct

<400> SEQUENCE: 38

Gln Gln His Tyr Thr Thr Pro Pro Thr
```

```
<210> SEQ ID NO 39
<211> LENGTH: 120
<212> TYPE: PRT
<213> ORGANISM: Artificial Sequence
<220> FEATURE:
<223> OTHER INFORMATION: Synthetic Construct

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 40
<211> LENGTH: 107
<212> TYPE: PRT
<213> ORGANISM: Artificial Sequence
<220> FEATURE:
<223> OTHER INFORMATION: Synthetic Construct

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105
```

METHODS FOR ASSAYING T-CELL DEPENDENT BISPECIFIC ANTIBODIES

CROSS-REFERENCE TO RELATED APPLICATIONS

This application is a U.S. National Phase Application under 35 U.S.C. § 371 of International Application No. PCT/US2017/014974, filed Jan. 25, 2017, which claims the benefit of U.S. Provisional Application 62/286,862, filed Jan. 25, 2016, the contents of which are hereby incorporated by reference in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 146392036200SEQLIST.TXT, date recorded: Jul. 23, 2018, size: 17 KB).

FIELD OF THE INVENTION

The present invention provides methods for analyzing preparations of multispecific antibodies having an antigen binding fragment that binds a T cell receptor complex subunit, such as a CD3 subunit, and an antigen binding fragment that binds a target antigen. In some embodiments, the invention provides methods for detecting a TDB in a composition, quantitating the amount of TDB in a composition, determining the potency and/or specificity of a TDB, or determining if a population of cells expresses a target antigen. Compositions and kits are also contemplated.

BACKGROUND OF THE INVENTION

T cell dependent bispecific antibodies (TDBs) are bispecific antibodies designed to bind a target antigen expressed on a target cell and a T cell receptor (TCR) complex subunit (e.g., CD3 subunit, such as CD3) expressed on a T cell. Binding of the bispecific antibody to the extracellular domains of both the target antigen and the TCR complex subunit (TCS) results in T cell recruitment to target cells, leading to T cell activation and target cell depletion Certain combinations of target antigen-specific and TCS-specific (such as CD3-specific) antigen binding fragments will be more effective than others for specifically activating T cells in the presence of target cells. Weakly activating TDBs will have little therapeutic benefit. Non-specific activation of T cells in the presence of off-target cells could lead to undesirable release of inflammatory cytokines. It is therefore desirable to assay the degree and specificity of T cell activation mediated by various TDBs in order to support the development of safe and efficacious clinical drug candidates.

Optimal T cell activation assays should be accurate, precise, and user-friendly, with short turnaround time and suitability for automation and high-throughput scaling. Several traditional bioassays are available, such as PBMC-based methods, FACS-based methods, and ELISA for secreted cytokines. Unfortunately, many of these assays yield highly variable results and/or are time consuming. The novel TDB assays described herein use a cell-based approach with target cells and reporter T cells to detect T cell activation, and are validated by ELISA-based bridging binding assays to detect simultaneous binding of both TDB antigen binding fragments to their targets.

All references cited herein, including patent applications and publications, are incorporated by reference in their entirety.

BRIEF SUMMARY

The invention provides methods for detecting T cell activation mediated by a T cell dependent bispecific antibody (TDB), wherein the TDB comprises a target antigen-binding fragment and a cell receptor complex subunit (TCS)-binding fragment, and various uses thereof In some embodiments, there is provided a method of detecting a TDB in a composition, wherein the TDB comprises a target antigen-binding fragment and a TCS-binding fragment (such as a CD3-binding fragment), the method comprising contacting the composition with a population of cells comprising a) T cells comprising nucleic acid encoding a reporter operably linked to a promoter and/or enhancer responsive to T cell activation; and b) target cells expressing the target antigen, wherein expression of the reporter indicates the presence of the TDB in the composition. In some embodiments, the reporter is a luciferase, a fluorescent protein, an alkaline phosphatase, a beta lactamase, or a beta galactosidase. In some embodiments, the luciferase is a firefly luciferase, a *Renilla* luciferase, or a nanoluciferase. In some embodiments, the promoter and/or enhancer responsive to T cell activation is an NFAT promoter, an AP-1 promoter, an NFκB promoter, a FOXO promoter, a STAT3 promoter, a STAT5 promoter or an IRF promoter. In some embodiments, the promoter and/or enhancer responsive to T cell activation comprises T cell activation responsive elements from any one or more of NFAT, AP-1. NFκB, FOXO, STAT3, STAT5 and IRF. In some embodiments, the T cells in the population of cells are $CD4^+$ T cells or $CD8^+$ T cells. In some embodiments, the T cells in the population of cells are Jurkat T cells or CELL-2 T cells. In some embodiments, the TCS-binding fragment is a CD3-binding fragment. In some embodiments, the CD3-binding fragment is a CD3ε-binding fragment. In some embodiments, the target antigen is expressed on the surface of the target cells. In some embodiments, the target antigen is CD4, CD8, CD18, CD19, CD11a, CD11b, CD20, CD22, CD34, CD40, CD79α (CD79a), CD79β (CD79b), EGF receptor, HER2 receptor, HER3 receptor, HER4 receptor, FcRH5, CLL1, LFA-1, Mac1, p150, 95, VLA-4, ICAM-1, VCAM, αv/β3 integrin, VEGF, flk2/flt3 receptor; obesity (OB) receptor; mpl receptor; CTLA-4; protein C, BR3, c-met, tissue factor, β7, Tenb2, STEAP, or transmembrane tumor-associated antigens (TAA). In some embodiments, a) the target antigen is HER2 receptor and the target cell is a BT-474 cell, b) the target antigen is HER2 receptor and the target cell is a SKBR3 cell, c) the target antigen is CD20 and the target cell is a Wil2-S cell, or d) the target antigen is CD79b and the target cell is a BJAB cell. In some embodiments, the ratio of T cells to target cells in the population of cells is about 1:1, about 1:2, about 1:3, about 1:4, about 1:5, about 1:6, about 1:7, about 1:8, about 1:9, or about 1:10. In some embodiments, the ratio of T cells to target cells in the population of cells is about 1:4. In some embodiments, the population of cells ranges from about $1\times10^3$ to about $1\times10^6$. In some embodiments, the population of cells is about $1\times10^4$ to about $5\times10^4$.

In some embodiments of any of the methods of detecting a TDB in a composition described above, the population of cells is contacted with a composition comprising the TDB at a concentration range of any of about 0.01 ng/mL to about 5000 ng/mL, about 0.05 ng/mL to about 5000 ng/mL, about 0.1 ng/mL to about 5000 ng/mL, about 0.5 ng/mL to about 5000 ng/mL, about 1 ng/mL to about 5000 ng/mL, about 5 ng/mL to about 5000 ng/mL, about 10 ng/mL to about 5000 ng/mL, about 0.01 ng/mL to about 4000 ng/mL, about 0.01 ng/mL to about 3000 ng/mL, about 0.01 ng/mL to about 2000 ng/mL, about 0.01 ng/ml, to about 1000 ng/mL, about 0.01 ng/mL to about 500 ng/mL, about 0.01 ng/mL to about 100 ng/mL, about 0.01 ng/mL to about 50 ng/mL, about 0.01 ng/mL to about 10 ng/mL, about 0.01 ng/mL to about 5 ng/mL, about 0.1 ng/mL to about 1000 ng/mL, about 0.5 ng/mL to about 1000 ng/mL, about 1 ng/mL to about 100 ng/mL, about 1 ng/mL to about 1000 ng/mL, or about 5 ng/mL to about 5000 ng/mL.

In some embodiments of any of the methods of detecting a TDB in a composition described above, the reporter is detected after more than about any of 1 hr, 2 hr, 3 hr, 4 hr, 5 hr, 6 hr, 7 hr, 8 hr, 9 hr, 10 hr, 12 hr, 16 hr, 20 hr, or 24 hr after contacting the cells with the composition. In some embodiments, the reporter is detected between any of about 1 hr and about 24 hr, about 1 hr and about 12 hr, about 1 hr and about 8 hr, about 1 hr and about 6 hr, about 1 hr and about 4 hr, about 1 hr and about 2 hr, about 4 hr and about 24 hr, about 4 hr and about 12 hr, about 4 hr and about 8 hr, about 8 hr and about 24 hr, about 8 hr and about 12 hr, about 16 hr and about 24 hr, about 16 hr and about 20 hr, or about 20 hr and about 24 hr after contacting the cells with the composition.

In some embodiments, there is provided a method of quantifying the amount of a TDB in a composition, wherein the TDB comprises a target antigen-binding fragment and a TCS-binding fragment (such as a CD3-binding fragment), the method comprising contacting the composition with a population of cells comprising a) T cells comprising nucleic acid encoding a reporter operably linked to a promoter and/or enhancer responsive to T cell activation; and b) target cells expressing the target antigen, and correlating the expression of the reporter as a function of antibody concentration with a standard curve generated by contacting the population of T cells and target cells with different concentrations of a purified reference TDB. In some embodiments, the reporter is a luciferase, a fluorescent protein, an alkaline phosphatase, a beta lactamase, or a beta galactosidase. In some embodiments, the luciferase is a firefly luciferase, a *Renilla* luciferase, or a nanoluciferase. In some embodiments, the promoter and/or enhancer responsive to T cell activation is an NFAT promoter, an AP-1 promoter, an NFκB promoter, a FOXO promoter, a STAT3 promoter, a STAT5 promoter or an IRF promoter. In some embodiments, the promoter and/or enhancer responsive to T cell activation comprises T cell activation responsive elements from any one or more of NFAT, AP-1, NFκB, FOXO, STAT3, STAT5 and IRF. In some embodiments, the T cells in the population of cells are CD4$^+$ T cells or CD8$^+$ T cells. In some embodiments, the T cells in the population of cells are Jurkat T cells or CTLL-2 T cells. In some embodiments, the TCS-binding fragment is a CD3-binding fragment. In some embodiments, the CD3-binding fragment is a CD3ε-binding fragment. In some embodiments, the target antigen is expressed on the surface of the target cells. In some embodiments, the target antigen is CD4, CD8, CD18, CD19, CD11a, CD11b, CD20, CD22, CD34, CD40, CD79α (CD79a), CD79β (CD79b), EGF receptor, HER2 receptor, HER3 receptor, HER4 receptor, FcRH5, CLL1, LFA-1, Mac1, p150, 95, VLA-4, ICAM-1, VCAM, αv/β3 integrin, VEGF, flk2/flt3 receptor; obesity (OB) receptor; mpl receptor; CTLA-4; protein C, BR3, c-met, tissue factor, β7, Tenb2, STEAP, or transmembrane tumor-associated antigens (TAA). In some embodiments, a) the target antigen is HER2 receptor and the target cell is a BT-474 cell, b) the target antigen is HER2 receptor and the target cell is a SKBR3 cell, c) the target antigen is CD20 and the target cell is a Wil2-S cell, or d) the target antigen is CD79b and the target cell is a BJAB cell. In some embodiments, the ratio of T cells to target cells in the population of cells is about 1:1, about 1:2, about 1:3, about 1:4, about 1:5, about 1:6, about 1:7, about 1:8, about 1:9. or about 1:10. In some embodiments, the ratio of T cells to target cells in the population of cells is about 1:4. In some embodiments, the population of cells ranges from about $1\times10^3$ to about $1\times10^6$. In some embodiments, the population of cells is about $1\times10^4$ to about $5\times10^4$.

In some embodiments of any of the methods of quantifying the amount of a TDB in a composition described above, the standard curve is generated by contacting the population of cells with the purified reference TDB at a plurality of concentrations ranging from about 0.01 ng/mL to about 5000 ng/mL. In some embodiments, the plurality of concentrations of purified reference TDB include about any one of 0.01 ng/ml, 0.1 ng/ml, 1 ng/ml, 10 ng/ml, 100 ng/mL, 150 ng/mL, 200 ng/mL, 250 ng/mL, 500 ng/mL, 750 ng/mL, 1 μg/mL, 2.5 μg/mL, 5 μg/mL, 10 μg/mL, 25 μg/mL, 50 μg/mL, 100 μg/mL, 250 μg/mL, or 500 μg/mL. In some embodiments, the plurality of concentrations of reference TDB is about three, four, five, six, seven, eight, nine, ten or more than ten concentrations.

In some embodiments of any of the methods of quantifying the amount of a TDB in a composition described above, the reporter is detected after more than about any of 1 hr, 2 hr, 3 hr, 4 hr, 5 hr, 6 hr, 7 hr, 8 hr, 9 hr, 10 hr, 12 hr, 16 hr, 20 hr, or 24 hr after contacting the cells with the composition. In some embodiments, the reporter is detected between any of about 1 hr and about 24 hr, about 1 hr and about 12 hr, about 1 hr and about 8 hr, about 1 hr and about 6 hr, about 1 hr and about 4 hr, about 1 hr and about 2 hr, about 4 hr and about 24 hr, about 4 hr and about 12 hr, about 4 hr and about 8 hr, about 8 hr and about 24 hr, about 8 hr and about 12 hr, about 16 hr and about 24 hr, about 16 hr and about 20 hr, or about 20 hr and about 24 hr after contacting the cells with the composition.

In some embodiments, there is provided a method of determining the specificity of T cell activation mediated by a TDB, wherein the TDB comprises a target antigen-binding fragment and a TCS-binding fragment (such as a CD3-binding fragment), the method comprising a) contacting a composition comprising the TDB with a population of cells comprising i) T cells comprising nucleic acid encoding a reporter operably linked to a promoter and/or enhancer responsive to T cell activation; and ii) test cells that do not express the target antigen and b) contacting a composition comprising the TDB with a population of cells comprising i) T cells comprising nucleic acid encoding a reporter operably linked to a promoter and/or enhancer responsive to T cell activation; and ii) target cells that express the target antigen, and comparing expression of the reporter in the presence of the test cell in part a) with expression of the reporter in the presence of target cells in part b), wherein the ratio of expression of the reporter of the test cells to the target cells is indicative of the specificity of the TDB for the target cells. In some embodiments, the reporter is a luciferase, a fluorescent protein, an alkaline phosphatase, a beta lactamase, or a beta galactosidase. In some embodiments, the luciferase is a firefly luciferase, a *Renilla* luciferase, or a nanoluciferase. In some embodiments, the promoter and/or enhancer responsive to T cell activation is an NFAT promoter, an AP-1 promoter, an NFκB promoter, a FOXO promoter, a STAT3 promoter, a STAT5 promoter or an IRF promoter. In some embodiments, the promoter and/or enhancer responsive to T cell activation comprises T cell activation responsive elements from any one or more of NFAT, AP-1, NFκB, FOXO, STAT3, STAT5 and IRF. In some embodiments, the T cells in the population of cells are CD4+ T cells or CD8+ T cells. In some embodiments, the T cells in the population of cells are Jurkat T cells or CTLL-2 cells. In some embodiments, the TCS-binding fragment is a CD3-binding fragment. In some embodiments, the CD3-binding fragment is a CD3ε-binding fragment. In some embodiments, the target antigen is expressed on the surface of the target cells. In some embodiments, the target antigen is CD4, CD8, CD18, CD19, CD11a, CD11b, CD20, CD22, CD34, CD40, CD79α (CD79a), CD79β (CD79b), EGF receptor, HER2 receptor, HER3 receptor, HER4 receptor, FcRH5, CLL1, LFA-1, Mac1, p150, 95, VLA-4, ICAM-1, VCAM, αv/β3 integrin, VEGF, flk2/flt3 receptor; obesity (OB) receptor; mpl receptor; CTLA-4; protein C, BR3, c-met, tissue factor, β7, Tenb2, STEAP, or transmembrane tumor-associated antigens (TAA), in some embodiments, a) the target antigen is HER2 receptor and the target cell is a BT-474 cell, b) the target antigen is HER2 receptor and the target cell is a SKBR3 cell, c) the target antigen is CD20 and the target cell is a Wil2-S cell, or d) the target antigen is CD79b and the target cell is a BJAB cell. In some embodiments, the ratio of T cells to test cells in the population of cells of step a) and/or the ratio of T cells to target cells in the population of cells of step b) is about 1:1, about 1:2, about 1:3, about 1:4, about 1:5, about 1:6, about 1:7, about 1:8, about 1:9 or about 1:10. In some embodiments, the ratio of T cells to test cells in the population of cells of step a) and/or the ratio of T cells to target cells in the population of cells or step b) is about 1:4. In some embodiments, the population of cells of steps a) and/or b) ranges from about $1\times10^3$ to about $1\times10^6$. In some embodiments, the population of cells of steps a) and/or b) ranges from about $1\times10^4$ to about $5\times10^4$.

In some embodiments of any of the methods of determining the specificity of T cell activation mediated by a TDB described above, the population of T cells and test cells of step a) and the population of T cells and target cells of step b) are contacted with a composition comprising the TDB at a concentration range of any of about 0.01 ng mL to about 5000 ng/mL, about 0.05 ng/mL to about 5000 ng/mL, about 0.1 ng/mL to about 5000 ng/mL, about 0.5 ng/mL to about 5000 ng/mL, about 1 ng/mL to about 5000 ng/mL, about 5 ng/mL to about 5000 ng/mL, about 10 ng/mL to about 5000 ng/mL, about 0.01 ng/mL, to about 4000 ng/mL, about 0.01 ng/mL to about 3000 ng/mL, about 0.01 ng/mL to about 2000 ng/mL, about 0.01 ng/mL to about 1000 ng/mL, about 0.01 ng/mL to about 500 ng/mL, about 0.01 ng/mL to about 100 ng/mL, about 0.01 ng/mL to about 50 ng/mL, about 0.01 ng/mL to about 10 ng/mL, about 0.01 ng/mL, to about 5 ng/mL, about 0.1 ng/mL to about 1000 ng/mL, about 0.5 ng/mL to about 1000 ng/mL, about 1 ng/mL to about 100 ng/mL, about 1 ng/mL to about 1000 ng/mL, or about 5 ng/mL to about 5000 ng/mL.

In some embodiments of any of the methods of determining the specificity of T cell activation mediated by a TDB described above, the reporter is detected after more than about any of 1 hr, 2 hr, 3 hr, 4 hr, 5 hr, 6 hr, 7 hr, 8 hr, 9 hr, 10 hr, 12 hr, 16 hr, 20 hr, or 24 hr after contacting the cells with the composition. In some embodiments, the reporter is detected between any of about 1 hr and about 24 hr, about 1 hr and about 12 hr, about 1 hr and about 8 hr, about 1 hr and about 6 hr, about 1 hr and about 4 hr, about 1 hr and about 2 hr, about 4 hr and about 24 hr, about 4 hr and about 12 hr, about 4 hr and about 8 hr, about 8 hr and about 24 hr, about 8 hr and about 12 hr, about 16 hr and about 24 hr, about 16 hr and about 20 hr, or about 20 hr and about 24 hr after contacting the cells with the composition.

In some embodiments, there is provided a kit for the detection of a TDB in a composition comprising a bispecific antibody comprising a target antigen-binding fragment and a TCS-binding fragment, wherein the kit comprises an engineered T cell comprising a reporter operably linked to a promoter and/or enhancer that is responsive to T cell activation. In some embodiments, the kit further comprises a reference TDB assay standard (a purified TDB of known concentration), and/or a TDB control. In some embodiments, the kit further comprises a composition comprising target cells expressing the target antigen. In some embodiments, the reporter is a luciferase, a fluorescent protein, an alkaline phosphatase, a beta lactamase, or a beta galactosidase. In some embodiments, the luciferase is a firefly luciferase, a *Renilla* luciferase, or a nanoluciferase. In some embodiments, the promoter and/or enhancer responsive to T cell activation is an NFAT promoter, an AP-1 promoter, an NFκB promoter, a FOXO promoter, a STAT3 promoter, a STAT5 promoter or an IRF promoter. In some embodiments, the promoter and/or enhancer responsive to T cell activation comprises T cell activation responsive elements from any one or more of NFAT, AP-1, NFκB, FOXO, STAT3, STAT5 and IRF. In some embodiments, the engineered T cells are CD4+ T cells or CD8+ T cells. In some embodiments, the engineered T cells are Jurkat T cells or CTLL-2 T cells. In some embodiments, the TCS-binding fragment is a CD3-binding fragment. In some embodiments, the CD3-binding fragment is a CD3ε-binding fragment. In some embodiments, the target antigen is expressed on the surface of the target cells. In some embodiments, the target antigen is CD4, CD8, CD18, CD19, CD11a, CD11b, CD20, CD22, CD34, CD40, CD79α (CD79a), CD79β (CD79b), EGF receptor, HER2 receptor, HER3 receptor, HER4 receptor, FcRH5, CULL1, LFA-1, Mac1, p150, 95, VLA-4, ICAM-1, VCAM, αv/β3 integrin, VEGF, flk2/flt3 receptor; obesity (OB) receptor; mpl receptor; CTLA-4; protein C, BR3, c-met, tissue factor, β7, Tenb2, STEAP, or transmembrane tumor-associated antigens (TAA). In some embodiments, a) the target antigen is HER2 receptor and the target cell is a BT-474 cell, b) the target antigen is HER2 receptor and the target cell is a SKBR3 cell, c) the target antigen is CD20 and the target cell is a Wil2-S cell, or d) the target antigen is CD79b and the target cell is a BJAB cell. In some embodiments, the kit is used in any of the methods described above.

In some embodiments, there is provided a method of determining if a population of test cells expresses a target antigen, the method comprising a) contacting the population of test cells with a population of T cells, wherein the T cells comprise nucleic acid encoding a reporter operably linked to a promoter and/or enhancer that is responsive to T cell activation; and b) contacting the population of T cells and test cells with the TDB, wherein the TDB comprises a target antigen-binding fragment and a TCS-binding fragment (such as a CD3-binding fragment), wherein expression of the reporter indicates the presence of the target antigen expressed by the test cell. In some embodiments, the reporter is a luciferase, a fluorescent protein, an alkaline phosphatase, a beta lactamase, or a beta galactosidase. In some embodiments, the luciferase is a firefly luciferase, a *Renilla* luciferase, or a nanoluciferase. In some embodiments, the promoter and/or enhancer responsive to T cell activation is an NFAT promoter, an AP-1 promoter, an NFκB promoter, a FOXO promoter, a STAT3 promoter, a STAT5 promoter or an IRF promoter. In some embodiments, the promoter and/or enhancer responsive to T cell activation comprises T cell activation responsive elements from any one or more of NFAT, AP-1, NFκB, FOXO, STAT3, STAT5 and IRF. In some embodiments, the population of T cells is CD4$^+$ T cells or CD8$^+$ T cells. In some embodiments, the population of T cells is Jurkat T cells or CTLL-2 T cells. In some embodiments, the TCS-binding fragment is a CD3-binding fragment. In some embodiments, the CD3-binding fragment is a CD3ε-binding fragment. In some embodiments, the target antigen is expressed on the surface of the target cells. In some embodiments, the target antigen is CD4, CD8, CD18, CD19, CD11a, CD11b, CD20, CD22, CD34, CD40, CD79α (CD79a), CD79β (CD79b), EGF receptor, HER2 receptor, HER3 receptor, HER4 receptor, FcRH5, CLL1, Mac1, p150, 95, VLA-4, ICAM-1, VCAM, αv/β3 integrin, VEGF, flk2/flt3 receptor; obesity (OB) receptor; mpl receptor; CTLA-4; protein C, BR3, c-met, tissue factor, β7, Tenb2, STEAP, or transmembrane tumor-associated antigens (TAA). In some embodiments, the population of test cells are is a population of tumor cells, immune cells or vascular cells. In some embodiments, the population of test cells does not comprise T cells. In some embodiments, the ratio of T cells to test cells is about 1:1, about 1:2, about 1:3, about 1:4, about 1:5, about 1:6, about 1:7, about 1:8, about 1:9 or about 1:10. In some embodiments, the ratio of T cells to test cells is about 1:4. In some embodiments, the population of test cells and T cells comprises from about 1×10$^3$ to about 1×10$^6$ cells. In some embodiments, the population of test cells and T cells comprises from about 1×10$^4$ to about 5×10$^4$ cells.

In some embodiments of any of the methods of determining if a population of test cells expresses a target antigen described above, the population of test cells and T cells is contacted with a composition comprising the TDB at a concentration range of any of about 0.01 ng/mL to about 5000 ng/mL, about 0.05 ng/mL to about 5000 ng/mL, about 0.1 ng/mL to about 5000 ng/m1about 0.5 ng/mL, to about 5000 ng/mL, about 1 ng/mL to about 5000 ng/mL, about 5 ng/mL to about 5000 ng/mL, about 10 ng/mL to about 5000 ng/mL, about 0.01 ng/mL to about 4000 ng/mL, about 0.01 ng/mL to about 3000 ng/mL, about 0.01 ng/mL to about 2000 ng/mL, about 0.01 ng/mL to about 1000 ng/mL, about 0.01 ng/mL to about 500 ng/mL, about 0.01 ng/mL to about 100 ng/mL, about 0.01 ng/mL to about 50 ng/mL, about 0.01 ng/mL to about 10 ng/mL, about 0.01 ng/mL to about 5 ng/mL, about 0.1 ng/mL to about 1000 ng/mL, about 0.5 ng/mL to about 1000 ng/mL, about 1 ng/mL to about 100 ng/mL, about 1 ng/mL to about 1000 ng/mL, or about 5 ng/mL to about 5000 ng/mL.

In some embodiments of any of the methods of determining if a population of test cells expresses a target antigen described above, the reporter is detected after more than about any of 1 hr, 2 hr, 3 hr, 4 hr, 5 hr, 6 hr, 7 hr, 8 hr, 9 hr, 10 hr, 12 hr, 16 hr, 20 hr, or 24 hr after contacting the cells with the composition. In some embodiments, the reporter is detected between any of about 1 hr and about 24 hr, about 1 hr and about 12 hr, about 1 hr and about 8 hr, about 1 hr and about 6 hr, about 1 hr and about 4 hr, about 1 hr and about 2 hr, about 4 hr and about 24 hr, about 4 hr and about 12 hr, about 4 hr and about 8 hr, about 8 hr and about 24 hr, about 8 hr and about 12 hr, about 16 hr and about 24 hr, about 16 hr and about 20 hr, or about 20 hr and about 24 hr after contacting the cells with the composition.

BRIEF DESCRIPTION OF THE DRAWINGS

FIG. 4A shows a comparison of purified CD20 TDB and purified anti-CD3 homodimer potential to activate T cells. Jurkat T cells expressing a NFκBLuciferase reporter gene are activated dose-dependently by CD20 TDB in the presence of target antigen expressing cells. CD20 TDB activates Jurkat/NFκB-fireflyLuciferase cells in the presence of the target antigen expressing cell line. Purified CD20 TDB is 1000-fold more active than purified anti-CD3 homodimer, in the presence of co-stimulatory target antigen-expressing cells. FIG. 4B shows that in the absence of target antigen-expressing cells (squares), CD20 TDB does not activate Jurkat/NFκBLuciferase cells, but purified anti-CD3 homodimer dose-dependently induces NFκB-dependent luciferase activity (diamonds).

FIG. 6A shows flow cytometry analysis of T cell activation by an exemplary αCD20/αCD3 TDB, BCTC4465A, at various concentrations. FIG. 6B shows quantification of the flow cytometry results.

FIG. 10A shows the relative potencies calculated using each assay and plotted for each condition tested. FIG. 10B shows the linear correlation between the relative potencies for calculated using each assay.

DETAILED DESCRIPTION OF THE INVENTION

Figure 1:
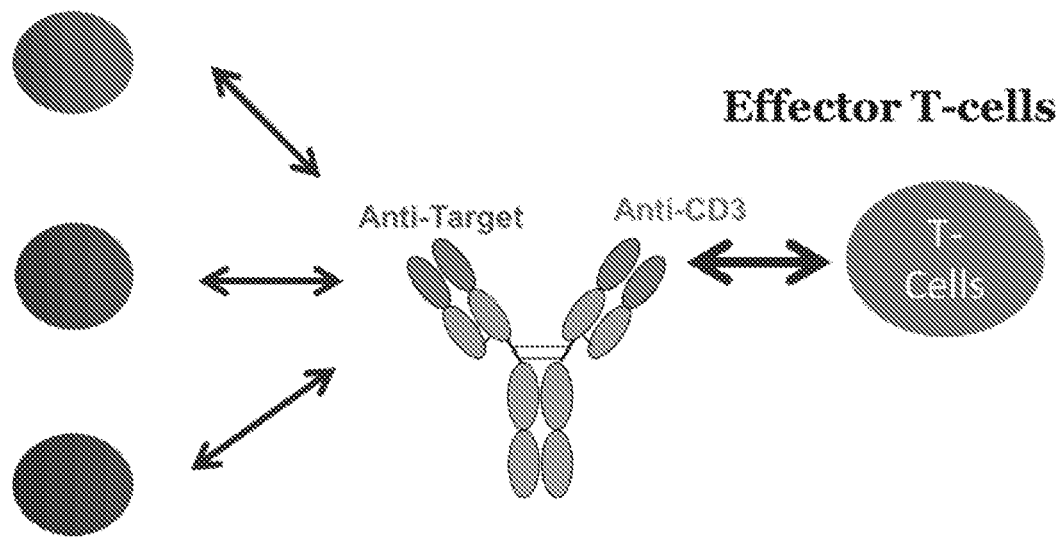
FIG. 1 shows a schematic representation of an exemplary T cell dependent bi-specific antibody (TDB), with a first arm having binding specificity for a target antigen and a second arm having specificity for a CD3 subunit.

The invention provides methods for detecting T cell activation mediated by a T cell dependent bispecific antibody (TDB) and/or determining the potency of a TDB, wherein the TDB comprises an antigen binding fragment that binds to a target antigen and an antigen binding fragment that binds to a T cell receptor complex subunit (TCS), such as a CD3 subunit, e.g., CD3ε, expressed on a T cell, and various uses thereof, including, inter cilia, detecting a TDB in a composition, quantitating the amount of TDB in a composition, determining the specificity of a TDB, and determining if a population of cells expresses a target antigen.

In other aspects, the invention provides kits for detecting T cell activation mediated by a TDB and/or determining the potency of a TDB, wherein the kit comprises an engineered T cell comprising a reporter operably linked to a promoter and/or enhancer responsive to T cell activation, and optionally includes the TDB, a reference TDB, a control TDB, and/or target cells.

I. Definitions

The term "polypeptide" or "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component or toxin. Also included within the definition are, for example, polypeptides containing one or more analogs of an amino acid (including, for example, unnatural amino acids, etc.), as well as other modifications known in the art. The terms "polypeptide" and "protein" as used herein specifically encompass antibodies.

"Purified" polypeptide (e.g., antibody or immunoadhesin) means that the polypeptide has been increased in purity, such that it exists in a form that is more pure than it exists in its natural environment and/or when initially synthesized and/or amplified under laboratory conditions. Purity is a relative term and does not necessarily mean absolute purity.

The term "antagonist" is used in the broadest sense, and includes any molecule that partially or fully blocks, inhibits, or neutralizes a biological activity of a native polypeptide. In a similar manner, the term "agonist" is used in the broadest sense and includes any molecule that mimics a biological activity of a native polypeptide. Suitable agonist or antagonist molecules specifically include agonist or antagonist antibodies or antibody fragments, fragments or amino acid sequence variants of native polypeptides, etc. Methods for identifying agonists or antagonists of a polypeptide may comprise contacting a polypeptide with a candidate agonist or antagonist molecule and measuring a detectable change in one or more biological activities normally associated with the polypeptide.

A polypeptide "which binds" an antigen of interest, e.g. a tumor-associated polypeptide antigen target, is one that binds the antigen with sufficient affinity such that the polypeptide is useful as a diagnostic and/or therapeutic agent in targeting a cell or tissue expressing the antigen, and does not significantly cross-react with other polypeptides. In such embodiments, the extent of binding of the polypeptide to a "non-target" polypeptide will be less than about 10% of the binding of the poly peptide to its particular target polypeptide as determined by fluorescence activated cell sorting (FACS) analysis or radioimmunoprecipitation (RIA).

With regard to the binding of a polypeptide to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target.

The term "antibody" herein is used in the broadest sense and specifically covers monoclonal antibodies, polyclonal antibodies, multispecific antibodies (e.g. bispecific antibodies including TDB) formed from at least two intact antibodies, and antibody fragments so long as they exhibit the desired biological activity. The term "immunoglobulin" (Ig) is used interchangeable with antibody herein.

Antibodies are naturally occurring immunoglobulin molecules which have varying structures, all based upon the immunoglobulin fold. For example, IgG antibodies have two "heavy" chains and two "light" chains that are disulphide-bonded to form a functional antibody. Each heavy and light chain itself comprises a "constant" (C) and a "variable" (V) region. The V regions determine the antigen binding specificity of the antibody, whilst the C regions provide structural support and function in non-antigen-specific interactions with immune effectors. The antigen binding specificity of an antibody or antigen-binding fragment of an antibody is the ability of an antibody to specifically bind to a particular antigen.

The antigen binding specificity of an antibody is determined by the structural characteristics of the V region. The variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" (HVRs) that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest,* 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

Each V region typically comprises three HVRs, e.g. complementarity determining regions ("CDRs", each of which contains a "hypervariable loop"), and four framework regions. An antibody binding site, the minimal structural unit required to bind with substantial affinity to a particular desired antigen, will therefore typically include the three CDRs, and at least three, preferably four, framework regions interspersed there between to hold and present the CDRs in the appropriate conformation. Classical four chain antibodies have antigen binding sites which are defined by $V_H$ and $V_L$ domains in cooperation. Certain antibodies, such as camel and shark antibodies, lack light chains and rely on binding sites formed by heavy chains only. Single domain engineered immunoglobulins can be prepared in which the binding sites are formed by heavy chains or light chains alone, in absence of cooperation between $V_H$ and $V_L$.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest,* 5th Ed. Public Health Service, National Institutes of Health, Bethesda, Md., (1991)). The constant domains are not involved directly in binding an antibody to an antigen, but exhibit various effector functions, such as participation of the antibody in antibody dependent cellular cytotoxicity (ADCC).

The term "hypervariable region" (HVR) when used herein refers to the amino acid residues of an antibody that are responsible for antigen binding. The hypervariable region may comprise amino acid residues from a "complementarity determining region" or "CDR" (e.g., around about residues 24-34 (L1), 50-56 (L2) and 89-97 (L3) in the $V_L$, and around about 31-35B (H1), 50-65 (H2) and 95-102 (H3) in the $V_H$ (Kabat et al., *Sequences of Proteins of Immunological Interest,* 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the $V_L$, and 26-32 (H1), 52A-55 (H2) and 96-101 (H3) in the $V_H$ (Chothia and Lesk *J. Mol. Biol.* 196:901-917 (1987)).

"Framework" or "FR" residues are those variable domain residues other than the hypervariable region residues as herein defined.

As used herein, "T cell dependent bispecific" antibodies or "TDB" are bispecific antibodies designed to bind a target antigen expressed on a cell, and to bind to T cells, such as by binding to a T cell receptor complex subunit (e.g., CD3ε) expressed on a T cell.

"Antibody fragments" comprise a portion of an intact antibody, preferably comprising the antigen binding region thereof. Examples of antibody fragments include Fab, Fab', F(ab')$_2$, and Fv fragments; diabodies; tandem diabodies (taDb), linear antibodies (e.g., U.S. Pat. No. 5,641,870, Example 2; Zapata et al., *Protein Eng.* 8(10):1057-1062 (1995)); one-armed antibodies, single variable domain antibodies, minibodies, single-chain antibody molecules multi-specific antibodies formed from antibody fragments (e.g., including but not limited to, Db-Fc, taDb-Fc, taDb-CH3, (scFV)4-Fc, bi-scFv, or tandem (di,tri)-scFv); and Bi-specific T-cell engagers (BiTEs).

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-binding sites and is still capable of cross-linking antigen.

"Fv" is the minimum antibody fragment that contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments that have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes). IgG1, IgG2IgG3, IgG4, IgA, and IgA2. The heavy chain constant domains that correspond to the different classes of antibodies are called α, δ, ε, γ, and μ, respectively. The subunit structures and three-dimensional configurations of different classes of immunoglobulins are well known.

"Single-chain Fv" or "scFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains that enables the scFv to form the desired structure for antigen binding. For a review of scFv see Plückthun in *The Pharmacology of Monoclona Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

The term "multispecific antibody" is used in the broadest sense and specifically covers an antibody that has polyepitopic specificity. Such multispecific antibodies include, but are not limited to, an antibody comprising a heavy chain variable domain ($V_H$) and a light chain variable domain ($V_L$), where the $V_H V_L$ unit has polyepitopic specificity, antibodies having two or more $V_L$ and $V_H$ domains with each $V_H V_L$ unit binding to a different epitope, antibodies having two or more single variable domains with each single variable domain binding to a different epitope, full length antibodies, antibody fragments such as Fab, Fv, dsFv, scFv, diabodies, bispecific diabodies, triabodies, tri-functional antibodies, antibody fragments that have been linked covalently or non-covalently. "Polyepitopic specificity" refers to the ability to specifically bind to two or more different epitopes on the same or different target(s). "Monospecific" refers to the ability to bind only one epitope. According to one embodiment the multispecific antibody is an IgG antibody that binds to each epitope with an affinity of 5 µM to 0.001 pM, 3 µM, to 0.001 pM, 1 µM to 0.001 pM, 0.5 µM to 0.001 pM, or 0.1 µM to 0.001 pM.

The expression "single domain antibodies" (sdAbs) or "single variable domain (SVD) antibodies" generally refers to antibodies in which a single variable domain (VH or VL) can confer antigen binding. In other words, the single variable domain does not need to interact with another variable domain in order to recognize the target antigen. Examples of single domain antibodies include those derived from camelids (lamas and camels) and cartilaginous fish (e.g., nurse sharks) and those derived from recombinant methods from humans and mouse antibodies (*Nature* (1989) 341:544-546; *Dev Comp Immunol* (2006) 30:43-56; *Trend Biochem Sci* (2001) 26:230-235; *Trends Biotechnol* (2003): 21:484-490; WO 2005/035572; WO 03/035694; *Febs Lett* (1994) 339:285-290; WO00/29004; WO 02/051870).

The term "monoclonal antibody" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. In addition to their specificity, the monoclonal antibodies are advantageous in that they are uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the methods provided herein may be made by the hybridoma method first described by Kohler et al., *Nature* 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature* 352:624-628 (1991) and Marks et al., *J. Mol, Biol.* 222:581-597 (1991), for example.

The monoclonal antibodies herein specifically include "chimeric" antibodies (immunoglobulins) which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Nod. Acad. Sci. USA* 81:6851-6855 (1984)), Chimeric antibodies of interest herein include "primatized" antibodies comprising variable domain antigen-binding sequences derived from a non-human primate (e.g. Old World Monkey, such as baboon, rhesus or cynomolgus monkey) and human constant region sequences (U.S. Pat. No. 5,693,780).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence, except for FR substitution(s) as noted above. The humanized antibody optionally also will comprise at least a portion of an immunoglobulin constant region, typically that of a human immunoglobulin. For further details, see Jones et at., *Nature* 321:522-525 (1986); Riechmann et at., *Nature* 332: 323-329 (1988); and Presta, *Curr. Op. Street. Blot.* 2:593-596 (1992).

For the purposes herein, an "intact antibody" is one comprising heavy and light variable domains as well as an Fc region. The constant domains may be native sequence constant domains (e.g. human native sequence constant domains) or amino acid sequence variant thereof. Preferably, the intact antibody has one or more effector functions.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

A "naked antibody" is an antibody (as herein defined) that is not conjugated to a heterologous molecule, such as a cytotoxic moiety or radiolabel.

In some embodiments, antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells in summarized is Table 3 on page 464 of Ravetch and Kinet, *Anna. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al., *Proc. Natl. Acad. Sci. (USA)* 95:652-656 (1998).

"Human effector cells" are leukocytes that express one or more FcRs and perform effector functions. In some embodiments, the cells express at least FcγRIII and carry out ADCC effector function. Examples of human leukocytes that mediate ADCC include peripheral blood mononuclear cells (PBMC), natural killer (NK) cells, monocytes, cytotoxic T cells and neutrophils; with PBMCs and NK cells being preferred.

"Complement dependent cytotoxicity" or "CDC" refers to the ability of a molecule to lyse a target in the presence of complement. The complement activation pathway is initiated by the binding of the first component of the complement system (C1q) to a molecule (e.g. polypeptide an antibody)) complexed with a cognate antigen. To assess complement activation, a CDC assay, e.g as described in Gazzano-Santoro et at., *J. Immunol. Methods* 202:163 (1996), may be performed.

The terms "Fe receptor" or "FcR" are used to describe a receptor that binds to the Fc region of an antibody. In some embodiments, the FcR is a native sequence human FcR. Moreover, a preferred FcR is one that binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see Daëron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al. *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al. *J. Immunol.* 117:587 (1976) and Kim et al., *J. Immunol.* 24:249 (1994)).

"Contaminants" refer to materials that are different from the desired polypeptide product. In some embodiments of the invention, contaminants include charge variants of the polypeptide. In some embodiments of the invention, contaminants include charge variants of an antibody or antibody fragment. In other embodiments of the invention, the contaminant includes, without limitation: host cell materials, such as CHOP; leached Protein A; nucleic acid; a variant, fragment, aggregate or derivative of the desired polypeptide; another polypeptide; endotoxin; viral contaminant; cell culture media component, etc. In some examples, the contaminant may be a host cell protein (HCP) from, for example but not limited to, a bacterial cell such as an *E. coli* cell, an insect cell, a prokaryotic cell, a eukaryotic cell, a yeast cell, a mammalian cell, an avian cell, a fungal cell.

As used herein, the term "immunoadhesin" designates antibody-like molecules which combine the binding specificity of a heterologous polypeptide with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

By "reporter molecule", as used in the present specification, is meant a molecule which, by its chemical nature, provides an analytically identifiable signal which allows the detection of antigen-bound antibody. The most commonly used reporter molecules in this type of assay are either enzymes, fluorophores or radionuclide containing molecules (i.e. radioisotopes) and chemiluminescent molecules.

As used herein "essentially the same" indicates that a value or parameter has not been altered by a significant effect. For example, an ionic strength of a chromatography mobile phase at column exit is essentially the same as the initial ionic strength of the mobile phase if the ionic strength has not changed significantly. For example, an ionic strength at column exit that is within 10%, 5% or 1% of the initial ionic strength is essentially the same as the initial ionic strength.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise. It is understood that aspects and variations of the invention described herein include "consisting" and/or "consisting essentially of" aspects and variations.

ps II. Cell-Based Reporter Assays

The present invention provides cell-based assays to detect TDB-mediated T cell activation in the presence of target cells and/or to determine the potency of a TDB, wherein one antigen binding fragment of the TDB binds a TCR complex subunit (such as a CD3 subunit, e.g., CD3ε) and activates T cells and the other antigen binding fragment binds a target antigen on the target cell. The cell-based assays are useful, inter alia, for detecting a TDB in a composition, quantitating the amount of TDB in a composition, determining the specificity of a TDB, and determining if a population of cells expresses a target antigen.

A. T Cell Activation

The mechanism of action of a TDB is to specifically deplete a target antigen-expressing cell. Simultaneous binding of the TDB to a T cell receptor (TCR) complex subunit, or TCS, (such as CD3ε) and to a target antigen expressed on the surface of a target cell results in TCR clustering, leading to T cell activation and the cytotoxic depletion of the target cell. There have been many TDBs in the clinic (αCD3/αCD19, αCD3/αCD20, αCD3/αHER2; de Gast G C, et al., 1995, *Cancer Immunol Immunother.* 40(6):390-396; Buhmann R, et al.,2009 *Bone Marrow Transplant.* 43(5):383-397; Chan J K, et al., 2006. *Clin Cancer Res.* 12(6):1859-1867) and new versions of TDB-like bispecifics are being evaluated to improve clinical efficacy (Chames, P. and Baty, D. 2009, *MAbs* 1(6):539-547; Fournier, P. and Schirrmacher, V., 2013, *BioDrugs* 27(1):35-53). TDB bi-specifics are capable of activating both CD4+ and CD8+ T cell lineages, provided the right target-expressing cells are present. Activation of CD4+ T cells will result in the induction of cytokine gene expression (IL-2, etc.), leading to the recruitment and activation of other immune cells, including the expansion and proliferation of CD8+ T cells. CD8+ CTL activation results from the formation of an immunological synapse-like structure with target cells via TDB-mediated cellular bridging, leading to induction of transcription of Perforin and Granzymes (A, B, C; depending on CTL subtype), degranulization, and the localized release of Perforin and Granzymes across the 'immunological synapse'-like interface between the target and effector cell, and resulting in the killing of the target cell (Pores-Fernando, Pores-Fernando A T, Zweifach A, 2009, *Immunol Rev.,* 231(1):160-173; Pipkin, M E, et al., 2010, *Immunol Rev.,* 235(1):55-72). Effector cell-mediated cell killing is a relatively slow process requiring the stabilization of the synapse for several hours and requires the transcriptional dependent activation of the prfl gene and granzyme genes to ensure complete cell killing. Alternatively, CTL-mediated killing of target cells has also been shown to occur by Fas-mediated apoptosis (Pardo, J, et al., 2003, *Int Immunol.,* 15(12):1441-1450). The transcriptional regulation of the prfl, grB and Fas-mediated cell killing machinery is dependent on NFAT, NFκB and STAT enhancer elements located within the promoters of the genes required to mediate B cell depletion (Pipkin, M E, et al, 2010, *Immunol Rev.,* 235(1):55-72, Pardo, J, et al., 2003, *Int Immunol.,* 15(12):1441-1450). The strength of the interaction between the target and effector cells (immunological synapse) is dependent on other co-stimulatory molecules from which signaling is also necessary to stabilize and maintain the interaction between target and effector cell (Krogsgaard M, et al., 2003, *Semin Immunol.* 15(6):307-315; Pattu V, et al., 2013, *Front Immunol.,* 4:411; Klieger Y, et al., 2014, *Eur J Immunol.* 44(1):58-68; Schwartz J C, et al., 2002, *Nat Immunol.* 3(5):427-434). The monitoring of the transcriptional induction of target genes, through the use of reporter gene assays, is therefore a mechanism of action (MoA)-reflective alternative assay system to observe the activation of T cells by TDB.

T cell activation requires the spatial and kinetic reorganization of cell surface proteins and signaling molecules at the contact site of the antigen presenting cell to form the immunological synapse. Coordination of the activation and signaling of the TCR and co-stimulatory receptors (CD28, CD40, ICOS, etc.) and ligands regulates both the duration and signaling that is required for T cell activation. Antigens presented on the surface of antigen presenting cells (APCs) as MHC/peptide complexes can be recognized by TCRs on the surface of the T cell. MHC and TCR clustering initiates the recruitment and activation of signaling pathways that can lead to T cell activation, depending on the expression of co-stimulatory and immunomodulatory receptors, which play a key role in regulating T cell activation. Antibodies that bind to subunits of the TCR complex, such as CDR3ε (OKT3; Brown, W M, 2006, *Curr Opin Investig Drugs* 7:381-388; Ferran, C et al., 1993 *Exp Nephrol* 1:83-89), can induce T cell activation by cross-linking TCRs and thereby mimicking the clustering of TCRs at the immunological synapse, and have been used clinically, as well as for many years as a surrogate activators to study TCR signaling in vitro. TCR clustering by anti-CD3 antibodies without co-stimulation weakly activates T cells, but still leads to T cell activation and limited cytokine transcription and release. Anti-CD3 mediated signaling has been shown to activate several transcription factors, including NFAT, AP1, and NFκB (MF et al., 1995, *J, Leukoc. Biol.* 57:767-773; Shapiro V S et al., 1998, *J. Immunol.* 161(12)6455-6458; Pardo, J, et al., 2003, *Int Immunol.,* 15(12):1441-1450). Co-stimulation regulates the level and type of cytokine release via the modulation of signaling, impacting transcriptional regulation of cytokine expression and the nature of the T cell activation response (Shannon, M F et 471, 1995, *J. Leukoc. Biol.* 57:767-773). The TDB clusters TCRs on the cell surface of the T cell as a result of the bridge formed between the T cell and the target antigen-expressing cell. Transcriptional regulatory elements driving the expression of reporter genes that may be transcriptional induced by cell activation were tested in T cell lines to determine which events are activated by the TDB in the presence and absence of target cells.

B. Reporter Molecules

A reporter assay is an analytical method that enables the biological characterization of a stimulus by monitoring the induction of expression of a reporter in a cell. The stimulus leads to the induction of intracellular signaling pathways that result in a cellular response that typically includes modulation of gene transcription. In some examples, stimulation of cellular signaling pathways result in the modulation of gene expression via the regulation and recruitment of transcription factors to upstream non-coding regions of DNA that are required for initiation of RNA transcription leading to protein production. Control of gene transcription and translation in response to a stimulus is required to elicit the majority of biological responses such as cellular proliferation, differentiation, survival and immune responses. These non-coding regions of DNA, also called enhancers, contain specific sequences that are the recognition elements for transcription factors which regulate the efficiency of gene transcription and thus, the amount and type of proteins generated by the cell in response to a stimulus. In a reporter assay, an enhancer element and minimal promoter that is responsive to a stimulus is engineered to drive the expression of a reporter gene using standard molecular biology methods. The DNA is then transfected into a cell, which contains all the machinery to specifically respond to the stimulus, and the level of reporter gene transcription, translation, or activity is measured as a surrogate measure of the biological response.

In some aspects, the invention provides methods of detecting TDB-mediated T cell activation by contacting a TDB comprising a TCS-specific (such as a CD3 subunit-specific, e.g., a CD3ε-specific) antigen binding fragment and a target antigen-specific antigen binding fragment with a population of cells comprising a) cells comprising nucleic acid encoding a reporter operably linked to a promoter and/or enhancer responsive to T cell activation; and b) target cells presenting the target antigen on their surface, such that expression of the reporter indicates activation of the T cells. A reporter molecule may be any molecule for which an assay can be developed to measure the amount of that molecule that is produced by the cell in response to the stimulus. For example, a reporter molecule may be a reporter protein that is encoded by a reporter gene that is responsive to the stimulus (e.g., T cell activation). Commonly used examples of reporter molecules include, but are not limited to, luminescent proteins such as luciferase, which emit light that can be measured experimentally as a by-product of the catalysis of substrate. Luciferases are a class of luminescent proteins that are derived from many sources and include firefly luciferase (from the species, *Photinus pyralis*), *Renilla* luciferase from sea pansy (*Renilla reniformis*), click beetle luciferase (from *Pyrearinus termitilluminans*), marine copepod *Gaussia* luciferase (from *Gaussia princeps*), and deep sea shrimp Nano luciferase (from *Oplophorus gracilirostris*). Firefly luciferase catalyzes the oxygenation of luciferin to oxyluciferin, resulting in the emission of a photon of light, while other luciferases, such as *Renilla*, emit light by catalyzing the oxygenation of coelenterazine. The wavelength of light emitted by different luciferase forms and variants can be read using different filter systems, which facilitates multiplexing. The amount of luminescence is proportional to the amount of luciferase expressed in the cell, and luciferase genes have been used as a sensitive reporter to quantitatively evaluate the potency of a stimulus to elicit a biological response. Reporter gene assays have been used for many years for a wide range of purposes including basic research, HTS screening, and for potency (Brogan T, et al., 2012, *Radiat Res.* 177(4):508-513; Miraglia L J, et al., 2011, *Comb Chem High Throughput Screen.* 14(8):648-657; Nakajima Y, and Ohmiya Y. 2010, *Expert Opin Drug Discovery*, 5(9):835-849; Parekh B S, et al., 2012, *Mabs*, 4(3):310-318; Svobodova K, and Cajtham L T., 2010, *Appl Microbiol Biotechnol.*, 88(4): 839-847).

In some embodiments, the invention provides cell-based assays to detect TDB-mediated T cell activation in T cells comprising nucleic acid encoding a reporter operably linked to a promoter and/or enhancer responsive to T cell activation. In some embodiments, the reporter construct comprises a luciferase. In some embodiments, the luciferase is a firefly luciferase (e.g from the species *Photinus pyralis*), *Renilla* luciferase from sea pansy (e.g., from the species *Renilla reniformis*), click beetle luciferase (e.g., from the species *Pyrearinus termitilluminans*), marine copepod *Gaussia* luciferase (e.g., from the species *Gaussia princeps*), or deep sea shrimp Nano luciferase (e.g., from the species *Oplophorus gracilirostris*). In some embodiments, expression of luciferase in the engineered T cell indicates the activation of T cells by the TDB. In other aspects, the reporter construct encodes a β-glucuronidase (GUS); a fluorescent protein such as Green fluorescent protein (GFP), red fluorescent protein (RFP), blue fluorescent protein (BFP), yellow fluorescent protein (YFP) or variants thereof; a chloramphenicoal acetyltransferase (CAT); a β-galactosidase; a β-lactamase; or a secreted alkaline phosphatase (SEAP).

In some embodiments, there are provided engineered T cells comprising nucleic acid encoding a reporter molecule (e.g., a reporter protein, such as a luciferase) operably linked to control sequences comprising a promoter and/or enhancers responsive to T cell activation. Promoter and/or enhancer sequences can be selected from among any of those known in the art to be responsive to T cell activation. In some embodiments, the nucleic acid is stably integrated into the T cell genome.

In some embodiments, there are provided engineered T cells comprising nucleic acid encoding a reporter molecule under the control of a minimal promoter operably linked to one or more T cell activation responsive enhancer elements. In some embodiments, the minimal promoter is a thymidine kinase (TK) minimal promoter, a minimal promoter from cytomegalovirus (CMV), an SV40-derived promoter, or a minimal elongation factor 1 alpha (EF1α) promoter. In some embodiments, the minimal promoter is a minimal TK promoter. In some embodiments, the minimal promoter is a minimal CMV promoter. In some embodiments, the T cell activation responsive enhancer elements are NFAT (Nuclear Factor of Activated T cells) enhancers, AP-1 (Fos/Jun) enhancers, NFAT/AP1 enhancers, NFκB enhancers, FOXO enhancers. STAT3 enhancers, STAT5 enhancers or IRF enhancers. In some embodiments, the T cell activation responsive enhancer elements are arranged as tandem repeats (such as about any of 2, 3, 4, 5, 6, 7, 8, or more tandem repeats). The T cell activation responsive enhancer elements may be positioned 5' or 3' to the reporter-encoding sequence. In some embodiments, the T cell activation responsive enhancer elements are located at a site 5' from the minimal promoter. In some embodiments, the T cell activation responsive enhancer elements are NFκB enhancers. In some embodiments, the reporter molecule is a luciferase, such as firefly or *Renilla* luciferase. In some embodiments, the nucleic acid is stably integrated into the T cell genome.

C. Cells

In some embodiments, there are provided methods of detecting TDB-mediated T cell activation by contacting a TDB comprising a TCS-specific (such as CD3-specific, e.g., CD3ε-specific) antigen binding fragment and a target antigen-specific antigen binding fragment with a population of cells comprising a) T cells comprising nucleic acid encoding a reporter operably linked to a promoter and/or enhancer responsive to T cell activation; and b) target cells presenting the target antigen on their surface, such that expression of the reporter indicates activation of the T cells In some embodiments, the T cells are $CD8^+$ T cells. In yet other embodiments, the T cell is a $CD4^+/CD8^+$ T cell. In some embodiments, the $CD4^+$ and/or $CD8^+$ T cells exhibit increased release of cytokines selected from the group consisting of IFN-γ, TNF-α, and interleukins. In some embodiments, the population of T cells is a population of immortalized T cells (e.g., an immortalized T cell line). In some embodiments, the population of T cells is a population of immortalized CD4$^+$ and/or CD8$^+$ cells that expressed TCR/CD3ε. In some embodiments, the T cell is a Jurkat cell. In some embodiments, the T cell is a CTLL-2 T cell.

In some embodiments, T cells of the invention comprise a cell receptor. T cell receptors exist as a complex of several proteins. The T cell receptor itself is composed of two separate peptide chains encoded by the independent T cell receptor alpha and beta (TCRα and TCRβ) genes. Other proteins in the complex include the CD3 proteins: CD3ε, CD3γ, CD3δ and CD3ζ. The CD3 proteins are found as CD3εγ and CD3εδ heterodimers and a CD3ζ homodimer. The CD3 ζ homodimer allows the aggregation of signaling complexes around these proteins. In some embodiments, one arm of the TDB binds a T cell receptor complex. In some embodiments, the TDB binds CD3. In some embodiments, the TDB binds the CD3ε subunit.

In some embodiments, the invention provides compositions comprising T cells for use in a cell-based assay to detect and/or quantitate TDB-mediated T cell activation. In some embodiments the T cells of the composition are CD4$^+$ T cell. In some embodiments, the T cells of the composition are CD8$^+$ T cell. In yet other embodiments, the T cells of the composition are CD4$^+$/CD8$^+$ cells. In some embodiments, the T cells of the composition are immortalized T cells. In some embodiments, the cells of the composition are Jurkat cells. In some embodiments, the T cells of the composition are CTLL-2 T cells. In some embodiments, the T cells of the composition comprise a reporter construct responsive to T cell activation. In some embodiments, the reporter construct comprises a polynucleotide encoding a luciferase. In some embodiments, the luciferase is a firefly luciferase, a *Renilla* luciferase, or a nanoluciferase. In some embodiments, the polynucleotide encoding the reporter (e.g., luciferase) is operably linked to a T cell activation responsive regulatory element (e.g., a cell activation responsive promoter and/or enhancer). In some embodiments, the promoter and/or enhancer responsive to T cell activation is an NFAT promoter, an AP-1 promoter, an NFκB promoter, a FOXO promoter, a STAT3 promoter, a STAT5 promoter or an IRF promoter.

In some embodiments, the invention provides compositions of cells engineered with a T cell activation reporter construct encoding a reporter molecule operably linked to control sequences comprising a promoter and/or enhancers responsive to T cell activation. In some embodiments, the reporter molecule is a luciferase, a fluorescent protein (e.g., a GFP, aYFP, etc.), an alkaline phosphatase, or a beta galactosidase. In some embodiments, the luciferase is a firefly luciferase, a *Renilla* luciferase, or a nanoluciferase. In some embodiments, the promoter and/or enhancer responsive to T cell activation is an NFAT promoter, an AP-1 promoter, an NFκB promoter, a FOXO promoter, a STAT3 promoter, a STAT5 promoter or an IRF promoter. In some embodiments, the enchancer responsive to T cell activation comprises T cell responsive enhancer elements from any one or more of NFAT, AP-1, NFκB, FOXO, STAT3, STAT5 and IRF. In some embodiments, the composition of T cells comprises CD4$^+$ T cells and/or CD8$^+$ T cells. In some embodiments, the T cells are Jurkat cells or CTLL-2 cells, in some embodiments, the T cells are Jurkat cells comprising a polynucleotide encoding a luciferase operably linked to an NFκB promoter.

In some embodiments, the reporter effector cells are Jurkat-Dual™ Cells (InvivoGen), Jurkat-Dual™ Cells comprise the Lucia™ secreted lucifierase gene under the control of five copies of the consensus NF-κB transcriptional response element and three copies of the c-Rel binding site. The cells also comprise a secreted embryonic alkaline phosphatase (SEAP) gene under the control of an ISG54 minimal promoter and five interferon-stimulated response elements.

D. TDB-Mediated T Cell Activation Assay, and Uses Thereof

In some aspects, the invention provides methods for detecting T cell activation mediated by a TDB, wherein the TDB comprises a target antigen-binding fragment and a TCS-binding fragment (such as a CD3-binding fragment), the method comprising contacting a composition comprising the TDB with a population of cells comprising a) T cells comprising nucleic acid encoding a reporter operably linked to a promoter and/or enhancer responsive to T cell activation; and b) target cells expressing the target antigen, wherein expression of the reporter indicates the presence of TDB-mediated T cell activation. In some embodiments, the reporter is a luciferase, a fluorescent protein, an alkaline phosphatase, a beta lactamase, or a beta galactosidase. In some embodiments, the luciferase is a firefly luciferase, a *Renilla* luciferase, or a nanoluciferase. In some embodiments, the promoter and/or enhancer responsive to T cell activation is an NFAT promoter, an AP-1 promoter, an NFκB promoter, a FOXO promoter, a STAT3 promoter, a STAT5 promoter or an IRF promoter. In some embodiments, the promoter and/or enhancer responsive to T cell activation comprises T cell activation responsive elements from any one or more of NFAT, AP-1, NFκB, FOXO, STAT3, STAT5 and IRF. In some embodiments, the cells in the population of cells are CD4$^+$ T cells or CD8$^+$ T cells. In some embodiments, the cells in the population of cells are Jurkat T cells or CTLL-2 T cells. In some embodiments, the TCS-binding fragment is a CD3-binding fragment. In some embodiments, the CD3-binding fragment is a CD3ε-binding fragment. In some embodiments, the target antigen is expressed on the surface of the target cells. In some embodiments, the target antigen is CD4, CD8, CD18, CD19, CD11a, CD11b, CD20, CD22, CD34, CD40, CD79α (CD79a), CD79β (CD79b), EGF receptor, HER2 receptor, HER3 receptor, HER4 receptor, FcRH5, CLL1, LFA-1, Mac1, p150, 95, VLA-4, ICAM-1, VCAM, αv/β3 integrin, VEGF, flk2/flt3 receptor; obesity (OB) receptor; mpl receptor; CTLA-4; protein C, BR3, c-met, tissue factor, β7, Tenb2, STEAP, or transmembrane tumor-associated antigens (TAA). In some embodiments, a) the target antigen is HER2 receptor and the target cell is a BT-474 cell, b) the target antigen is HER2 receptor and the target cell is a SKBR3 cell, c) the target antigen is CD20 and the target cell is a Wil2-S cell, or d) the target antigen is CD79b and the target cell is a BJAB cell. In some embodiments, the ratio of T cells to target cells in the population of cells is about 1:1, about 1:2, about 1:3, about 1:4, about 1:5, about 1:6, about 1:7, about 1:8, about 1:9, or about 1:10. In some embodiments, the ratio of T cells to target cells in the population of cells is about 1:4. In some embodiments, the population of cells ranges from about 1×10$^3$ to about 1×10$^6$. In some embodiments, the population of cells is about 1×10$^4$ to about 5×10$^4$.

In some embodiments, the population of cells is contacted with a composition comprising the TDB at a concentration range of any of about 0.01 ng/mL to about 5000 ng/mL, about 0.05 ng/mL to about 5000 ng/mL, about 0.1 ng/mL to about 5000 ng/mL, about 0.5 ng/mL to about 5000 ng/mL, about 1 ng/mL, to about 5000 ng/mL about 5 ng/mL to about 5000 ng/mL, about 10 ng/mL to about 5000 ng/mL, about 0.01 ng/mL, to about 4000 ng/mL, about 0.01 ng/mL to about 3000 ng/mL, about 0.01 ng/mL to about 2000 ng/mL, about 0.01 ng/mL to about 1000 ng/mL, about 0.01 ng/mL to about 500 ng/mL, about 0.01 ng/mL to about 100 ng/mL, about 0.01 ng/mL to about 50 ng/mL, about 0.01 ng/mL to about 10 ng/mL, about 0.01 ng/mL, to about 5 ng/mL, about 0.1 ng/mL to about 1000 ng/mL, about 0.5 ng/mL to about 1000 ng/mL, about 1 ng/mL to about 100 ng/mL, about 1 ng/mL to about 1000 ng/mL, or about 5 ng/mL to about 5000 ng/mL.

In some embodiments, the reporter is detected after more than about any of 1 hr, 2 hr, 3 hr, 4 hr, 5 hr, 6 hr, 7 hr, 8 hr, 9 hr, 10 hr, 12 hr, 16 hr, 20 hr, or 24 hr after contacting the cells with the composition. In some embodiments, the reporter is detected between any of about 1 hr and about 24 hr, about 1 hr and about 12 hr, about 1 hr and about 8 hr, about 1 hr and about 6 hr, about 1 hr and about 4 hr, about 1 hr and about 2 hr, about 4 hr and about 24 hr, about 4 hr and about 12 hr, about 4 hr and about 8 hr, about 8 hr and about 24 hr, about 8 hr and about 12 hr, about 16 hr and about 24 hr, about 16 hr and about 20 hr, or about 20 hr and about 24 hr after contacting the cells with the composition.

In some aspects, the invention provides methods for detecting a TDB in a composition, wherein the TDB comprises a target antigen-binding fragment and a TCS-binding fragment (such as a CD3-binding fragment), the method comprising contacting the composition with a population of cells comprising a) T cells comprising nucleic acid encoding a reporter operably linked to a promoter and/or enhancer responsive to T cell activation; and b) target cells expressing the target antigen, wherein expression of the reporter indicates the presence of the TDB in the composition. In some embodiments, the reporter is a luciferase, a fluorescent protein, an alkaline phosphatase, a beta lactamase, or a beta galactosidase. In some embodiments, the luciferase is a firefly luciferase, a Renilla luciferase, or a nanoluciferase. In some embodiments, the promoter and/or enhancer responsive to T cell activation is an NFAT promoter, an AP-1 promoter, an NFκB promoter, a FOXO promoter, a STAT3 promoter, a STAT5 promoter or an IRF promoter. In some embodiments, the promoter and/or enhancer responsive to T cell activation comprises T cell activation responsive elements from any one or more of NFAT, AP-1, NFκB, FOXO, STAT3, STAT5 and IRF. In some embodiments, the T cells in the population of cells are CD4$^+$ cells or CD8$^+$ T cells. In some embodiments, the T cells in the population of cells are Jurkat T cells or CTLL-2 T cells. In some embodiments, the TCS-binding fragment is a CD3-binding fragment. In some embodiments, the CD3-binding fragment is a CD3ε-binding fragment. In some embodiments, the target antigen is expressed on the surface of the target cells. In some embodiments, the target antigen is CD4, CD8, CD18, CD19, CD11a, CD11b, CD20, CD22, CD34, CD40, CD79α (CD79a), CD79β (CD79b), EGF receptor, HER2 receptor, HER3 receptor, HER4 receptor, FcRH5, CLL1, LFA-1, Mac1, p150, 95, VLA-4, ICAM-1, VCAM, αv/β3 integrin, VEGF, flk2/flt3 receptor; obesity (OB) receptor; mpl receptor; CTLA-4; protein C, BR3, c-met, tissue factor, β7, Tenb2, STEAP, or transmembrane tumor-associated antigens (TAA). In some embodiments, a) the target antigen is HER2 receptor and the target cell is a BT-474 cell, b) the target antigen is HER2 receptor and the target cell is a SKBR3 cell, c) the target antigen is CD20 and the target cell is a Wil2-S cell, or d) the target antigen is CD79b and the target cell is a BJAB cell. In some embodiments, the ratio of T cells to target cells in the population of cells is about 1:1, about 1:2, about 1:3, about 1:4, about 1:5, about 1:6, about 1:7, about 1:8, about 1:9, or about 1:10. In some embodiments, the ratio of T cells to target cells in the population of cells is about 1:4. In some embodiments, the population of cells r s from about $1 \times 10^3$ to about $1 \times 10^6$ some embodiments, the population of cells is about $1 \times 10^4$ to about $5 \times 10^4$.

In some embodiments, the population of cells is contacted with a composition comprising the TDB at a concentration range of any of about 0.01 ng/mL to about 5000 ng/mL, about 0.05 ng/mL to about 5000 ng/mL, about 0.1 ng/mL to about 5000 ng/mL, about 0.5 ng/mL to about 5000 ng/mL, about 1 ng/mL to about 5000 ng/mL, about 5 ng/mL to about 5000 ng/mL, about 10 ng/mL to about 5000 ng/mL, about 0.01 ng/mL to about 4000 ng/mL, about 0.01 ng/mL to about 3000 ng/mL, about 0.01 ng/mL to about 2000 ng/mL, about 0.01 ng/mL to about 1000 ng/mL, about 0.01 ng/mL to about 500 ng/mL, about 0.01 ng/mL to about 100 ng/mL, about 0.01 ng/mL to about 50 ng/mL, about 0.01 ng/mL to about 10 ng/mL, about 0.01 ng/mL, to about 5 ng/mL, about 0.1 ng/mL to about 1000 ng/mL, about 0.5 ng/mL to about 1000 ng/mL, about 1 ng/mL to about 100 ng/mL, about 1 ng/mL to about 1000 ng/mL, or about 5 ng/mL to about 5000 ng/mL.

In some embodiments, the reporter is detected after more than about any of 1 hr, 2 hr, 3 hr, 4 hr, 5 hr, 6 hr, 7 hr, 8 hr, 9 hr, 10 hr, 12 hr, 16 hr, 20 hr, or 24 hr after contacting the cells with the composition. In some embodiments, the reporter is detected between any of about 1 hr and about 24 hr, about 1 hr and about 12 hr, about 1 hr and about 8 hr, about 1 hr and about 6 hr, about 1 hr and about 4 hr, about 1 hr and about 2 hr, about 4 hr and about 24 hr, about 4 hr and about 12 hr, about 4 hr and about 8 hr, about 8 hr and about 24 hr, about 8 hr and about 12 hr, about 16 hr and about 24 hr, about 16 hr and about 20 hr, or about 20 hr and about 24 hr after contacting the cells with the composition.

In some aspects, the invention provides methods for quantifying the amount of a TDB in a composition, wherein the TDB comprises a target antigen-binding fragment and a TCS-binding fragment (such as a CD3-binding fragment), the method comprising contacting the composition with a population of cells comprising a) T cells comprising nucleic acid encoding a reporter operably linked to a promoter and/or enhancer responsive to T cell activation; and b) target cells expressing the target antigen, and correlating the expression of the reporter as a function of antibody concentration with a standard curve generated by contacting the population of T cells and target cells with different concentrations of a purified reference TDB. In some embodiments, the reporter is a luciferase, a fluorescent protein, an alkaline phosphatase, a beta lactamase, or a beta galactosidase. In some embodiments, the luciferase is a firefly luciferase, a Renilla luciferase, or a nanoluciferase. In some embodiments, the promoter and/or enhancer responsive to T cell activation is an NFAT promoter, an AP-1 promoter, an NFκB promoter, a FOXO promoter, a STAT3 promoter, a STAT5 promoter or an IRF promoter. In some embodiments, the promoter and/or enhancer responsive to T cell activation comprises T cell activation responsive elements from any one or more of NFAT, AP-1, NFκB, FOXO, STAT3, STAT5 and IRF. In some embodiments, the T cells in the population of cells are CD4$^+$ T cells or CD8$^+$ T cells. In some embodiments, the T cells in the population of cells are Jurkat T cells or CTLL-2 T cells. In some embodiments, the TCS-binding fragment is a CD3-binding fragment. In some embodiments, the CD3-binding fragment is a CD3ε-binding fragment. In some embodiments, the target antigen is expressed on the surface of the target cells. In some embodiments, the target antigen is CD4, CD8, CD18, CD19, CD11a, CD11b, CD20, CD22, CD34, CD40, CD79α (CD79a), CD79β (CD79b), EGF receptor, HER2 receptor, HER3 receptor, HER4 receptor, FcRH5, CLL1, LFA-1, Mac1, p150, 95, VLA-4, ICAM-1, VCAM, αv/β3 integrin, VEGF, flk2/flt3 receptor; obesity (OB) receptor; mpl receptor; CTLA-4; protein C, BR3, c-met, tissue factor, β7, Tenb2, STEAP, or transmembrane tumor-associated antigens (TAA). In some embodiments, a) the target antigen is HER2 receptor and the target cell is a BT-474 cell, b) the target antigen is HER2 receptor and the target cell is a SKBR3 cell, c) the target antigen is CD20 and the target cell is a Wil2-S cell, or d) the target antigen is CD79b and the target cell is a BJAB cell. In some embodiments, the ratio of T cells to target cells in the population of cells is about 1:1, about 1:2, about 1:3, about 1:4, about 1:5, about 1:6, about 1:7; about 1:8, about 1:9, or about 1:10. In some embodiments, the ratio of T cells to target cells in the population of cells is about 1:4. In some embodiments, the population of cells ranges from about $1\times10^3$ to about $1\times10^6$. In some embodiments, the population of cells is about $1\times10^4$ to about $5\times10^4$.

In some embodiments, the standard curve is generated by contacting the population of cells with the purified reference TDB at a plurality of concentrations ranging from about 0.01 ng/mL to about 5000 ng/mL. In some embodiments, the plurality of concentrations of purified reference TDB include about any one of 0.01 ng/ml, 0.1 ng/ml, 1 ng/ml, 10 ng/ml, 100 ng/mL, 150 ng/mL, 200 ng/mL, 250 ng/mL, 500 ng/mL, 750 ng/mL, 2.5 µg/mL, 5 µg/mL, 10 µg/mL, 25 µg/mL, 50 µg/mL, 100 µg/mL, 250 µg/mL, or 500 µg/mL. In some embodiments, the plurality of concentrations of reference TDB is about three, four, five, six, seven, eight, nine, ten or more than ten concentrations.

In some embodiments, the reporter is detected after more than about any of 1 hr, 2 hr, 3 hr, 4 hr, 5 hr, 6 hr, 7 hr, 8 hr, 9 hr, 10 hr, 12 hr, 16 hr, 20 hr, or 24 hr after contacting the cells with the composition. In some embodiments, the reporter is detected between any of about 1 hr and about 24 hr, about 1 hr and about 12 hr, about 1 hr and about 8 hr, about 1 hr and about 6 hr, about 1 hr and about 4 hr, about 1 hr and about 2 hr, about 4 hr and about 24 hr, about 4 hr and about 12 hr, about 4 hr and about 8 hr, about 8 hr and about 24 hr, about 8 hr and about 12 hr, about 16 hr and about 24 hr, about 16 hr and about 20 hr, or about 20 hr and about 24 hr after contacting the cells with the composition.

In some aspects, the invention provides methods for determining the potency of T cell activation mediated by a TDB, wherein the TDB comprises a target antigen-binding fragment and a TCS-binding fragment (such as a CD3-binding fragment), the method comprising contacting a composition comprising the TDB with a population of cells comprising a) T cells comprising nucleic acid encoding a reporter operably linked to a promoter and/or enhancer responsive to T cell activation; and b) target cells expressing the target antigen, and correlating the expression of the reporter as a function of antibody concentration with a standard curve generated by contacting the population of cells with different concentrations of a reference TDB, thereby obtaining a relative measure of the potency of T cell activated mediated by the TDB. In some embodiments, the reporter is a luciferase, a fluorescent protein, an alkaline phosphatase, a beta lactamase, or a beta galactosidase. In some embodiments, the luciferase is a firefly luciferase, a Renilla luciferase, or a nanoluciferase. In some embodiments, the promoter and/or enhancer responsive to T cell activation is an NFAT promoter, an AP-1 promoter, an NFκB promoter, a FOXO promoter, a STAT3 promoter, a STAT5 promoter or an IRF promoter. In some embodiments, the promoter and/or enhancer responsive to T cell activation comprises T cell activation responsive elements from any one or more of NFAT, AP-1, NFκB, FOXO, STAT3, STAT5 and IRF. In some embodiments, the T cells in the population of cells are CD4$^+$ T cells or CD8$^+$ T cells. In some embodiments, the T cells in the population of cells are Jurkat T cells or CTLL-2 T cells. In some embodiments, the TCS-binding fragment is a CD3-binding fragment. In some embodiments, the CD3-binding fragment is a CD3ε-binding fragment. In some embodiments, the target antigen is expressed on the surface of the target cells. In some embodiments, the target antigen is CD4, CD8, CD18, CD19, CD11a, CD11b, CD20, CD22, CD34, CD40, CD79α, (CD79a), CD79β (CD79b), EGF receptor, HER2 receptor, HER3 receptor, HER4 receptor, FcRH5, CLL1, LFA-1, Mac1, p150, 95, VLA-4, ICAM-1, VCAM, αv/β3 integrin, VEGF, flk2/flt3 receptor; obesity (OB) receptor; mpl receptor; CTLA-4; protein C, BR3, c-met, tissue factor, β7, Tenb2, STEAP, or transmembrane tumor-associated antigens (TAA). In some embodiments, a) the target antigen is HER2 receptor and the target cell is a BT-474 cell, b) the target antigen is HER2 receptor and the target cell is a SKBR3 cell, c) the target antigen is CD20 and the target cell is a Wil2-S cell, or d) the target antigen is CD79b and the target cell is a BJAB cell. In some embodiments, the ratio of T cells to target cells in the population of cells is about 1:1. about 1:2, about 1:3, about 1:4, about 1:5, about 1:6, about 1:7, about 1:8, about 1:9, or about 1:10. In some embodiments, the ratio of T cells to target cells in the population of cells is about 1:4. In some embodiments, the population of cells ranges from about $1\times10^3$ to about $1\times10^6$. In some embodiments, the population of cells is about $1\times10^4$ to about $5\times10^4$.

In some embodiments, the population of cells is contacted with a composition comprising the TDB at a concentration range of any of about 0.01 ng/mL to about 5000 ng/mL, about 0.05 ng/mL to about 5000 ng/mL, about 0.1 ng/mL to about 5000 ng/mL, about 0.5 ng/mL to about 5000 ng/mL, about 1 ng/mL to about 5000 ng/mL, about 5 ng/mL to about 5000 ng/mL, about 10 ng/mL to about 5000 ng/mL, about 0.01 ng/mL to about 4000 ng/mL, about 0.01 ng/mL to about 3000 ng/mL, about 0.01 ng/mL to about 2000 ng/mL, about 0.01 ng/mL to about 1000 ng/mL, about 0.01 ng/mL to about 500 ng/mL, about 0.01 ng/mL, to about 100 ng/mL, about 0.01 ng/mL to about 50 ng/mL, about 0.01 ng/mL to about 10 ng/mL, about 0.01 ng/mL to about 5 ng/mL, about 0.1 ng/mL to about 1000 ng/mL, about 0.5 ng/mL to about 1000 ng,/mL, about 1 ng/mL to about 100 ng/mL, about 1 ng/mL to about 1000 ng/mL, or about 5 ng/mL to about 5000 ng/mL.

In some embodiments, the standard curve is generated by contacting the population of cells with the purified reference TDB at a plurality of concentrations ranging from about 0.01 ng/mL to about 5000 ng/mL. In some embodiments, the plurality of concentrations of purified reference TDB include about any one of 0.01 ng/ml, 0.1 ng/ml, 1 ng/ml, 10 ng/ml, 100 ng/mL, 150 ng/mL, 200 ng/mL, 250 ng/mL, 500 ng/mL, 750 ng/mL, 1 µg/mL, 2.5 µg/mL, 5 µg/mL, 10 µg/mL, 25 µg/mL, 50 µg/mL, 100 µg/mL, 250 µg/mL, or 500 µg/mL. In some embodiments, the plurality of concentrations of reference TDB is about three, four, five, six, seven, eight, nine, ten or more than ten concentrations.

In some embodiments, the reporter is detected after more than about any of 1 hr, 2 hr, 3 hr, 4 hr, 5 hr, 6 hr, 7 hr, 8 hr, 9 hr, 10 hr, 12 hr, 16 hr, 20 hr, or 24 hr after contacting the cells with the composition. In some embodiments, the reporter is detected between any of about 1 hr and about 24 hr, about 1 hr and about 12 hr, about 1 hr and about 8 hr, about 1 hr and about 6 hr, about 1 hr and about 4 hr, about 1 hr and about 2 hr, about 4 hr and about 24 hr, about 4 hr and about 12 hr, about 4 hr and about 8 hr, about 8 hr and about 24 hr, about 8 hr and about 12 hr, about 16 hr and about 24 hr, about 16 hr and about 20 hr, or about 20 hr and about 24 hr after contacting the cells with the composition.

In some aspects, the invention provides methods for determining the specificity of T cell activation mediated by a TDB, wherein the TDB comprises a target antigen-binding fragment and a TCS-binding fragment (such as a CD3-binding fragment), the method comprising a) contacting a composition comprising the TDB with a population of cells comprising i) T cells comprising nucleic acid encoding a reporter operably linked to a promoter and/or enhancer responsive to T cell activation; and ii) test cells that do not express the target antigen; and b) contacting a composition comprising the TDB with a population of cells comprising i) T cells comprising nucleic acid encoding a reporter operably linked to a promoter and/or enhancer responsive to T cell activation; and ii) target cells that express the target antigen, and comparing expression of the reporter in the presence of the test cell in part a) with expression of the reporter in the presence of target cells in part b), wherein the ratio of expression of the reporter of the test cells to the target cells is indicative of the specificity of the TDB for the target cells. In some embodiments, the reporter is a luciferase, a fluorescent protein, an alkaline phosphatase, a beta lactamase, or a beta galactosidase. In some embodiments, the luciferase is a firefly luciferase, a *Renilla* luciferase, or a nanoluciferase. In some embodiments, the promoter and/or enhancer responsive to T cell activation is an NFAT promoter, an AP-1 promoter, an NFκB promoter, a FOXO promoter, a STAT3 promoter, a STAT5 promoter or an IRF promoter. In some embodiments, the promoter and/or enhancer responsive to T cell activation comprises T cell activation responsive elements from any one or more of NFAT, AP-1, NFκB, FOXO, STAT3, STAT5 and IRF. In some embodiments, the T cells in the population of cells are $CD4^+$ T cells or $CD8^+$ T cells. In some embodiments, the T cells in the population of cells are Jurkat T cells or CTLL-2 cells. In some embodiments, the TCS-binding fragment is a CD3-binding fragment. In some embodiments, the CD3-binding fragment is a CD3ε-binding fragment. In some embodiments, the target antigen is expressed on the surface of the target cells. In some embodiments, the target antigen is CD4, CD8, CD18, CD19, CD11a, CD11b, CD20, CD22, CD34, CD40, CD79α (CD79a), CD79β (CD79b), EGF receptor, HER2 receptor, HER3 receptor, HER4 receptor, FcRH5, CLL1, LFA-1, Mac1, p150, 95, VLA-4, ICAM-1, TCAM, αv/β3 integrin, VEGF, flk2/flt3 receptor; obesity (OB) receptor; mpl receptor; CTLA-4; protein C, BR3, c-met, tissue factor, β7, Tenb2, STEAP, or transmembrane tumor-associated antigens (TAA). In some embodiments, a) the target antigen is HER2 receptor and the target cell is a BT-474 cell, b) the target antigen is HER2 receptor and the target cell is a SKBR3 cell, c) the target antigen is CD20 and the target cell is a Wil2-S cell, or d) the target antigen is CD79b and the target cell is a BJAB cell. In some embodiments, the ratio of T cells to test cells in the population of cells of step a) and/or the ratio of T cells to target cells in the population of cells of step b) is about 1:1, about 1:2, about 1:3, about 1:4, about 1:5, about 1:6, about 1:7, about 1:8, about 1:9 or about 1:10. In some embodiments, the ratio of T cells to test cells in the population of cells of step a) and/or the ratio of T cells to target cells in the population of cells or step b) is about 1:4. In some embodiments, the population of cells of steps a) and/or b) ranges from about $1\times10^3$ to about $1\times10^6$. In some embodiments, the population of cells of steps a) and/or b) ranges from about $1\times10^4$ to about $5\times10^4$.

In some embodiments, the population of T cells and test cells of step a) and the population of T cells and target cells of step b) are contacted with a composition comprising the TDB at a concentration range of any of about 0.01 ng/mL, to about 5000 ng/mL, about 0.05 ng/mL to about 5000 ng/mL, about 0.1 ng/mL to about 5000 ng/mL, about 0.5 ng/mL to about 5000 ng/mL, about 1 ng/mL to about 5000 ng/mL, about 5 ng/mL to about 5000 ng/mL, about 10 ng/mL to about 5000 ng/mL, about 0.01 ng/mL to about 4000 ng/mL, about 0.01 ng/mL to about 3000 ng/mL, about 0.01 ng/mL to about 2000 ng/mL, about 0.01 ng/mL to about 1000 ng/mL, about 0.01 ng/mL to about 500 ng/mL, about 0.01 ng/mL to about 100 ng/mL, about 0.01 ng/mL to about 50 ng/mL, about 0.01 ng/mL to about 10 ng/mL, about 0.01 ng/mL to about 5 ng/mL, about 0.1 ng/mL to about 1000 ng/mL, about 0.5 ng/mL to about 1000 ng/mL, about 1 ng/mL to about 100 ng/mL, about 1 ng/mL to about 1000 ng/mL, or about 5 ng/mL to about 5000 ng/mL.

In some embodiments, the reporter is detected after more than about any of 1 hr, 2 hr, 3 hr, 4 hr, 5 hr, 6 hr, 7 hr, 8 hr, 9 hr, 10 hr, 12 hr, 16 hr, 20 hr, or 24 hr after contacting the cells with the composition. In some embodiments, the reporter is detected between any of about 1 hr and about 24 hr, about 1 hr and about 12 hr, about 1 hr and about 8 hr, about 1 hr and about 6 hr, about 1 hr and about 4 hr, about 1 hr and about 2 hr, about 4 hr and about 24 hr, about 4 hr and about 12 hr, about 4 hr and about 8 hr, about 8 hr and about 24 hr, about 8 hr and about 12 hr, about 16 hr and about 24 hr, about 16 hr and about 20 hr, or about 20 hr and about 24 hr after contacting the cells with the composition.

In some aspects, the invention provides methods for determining if a population of test cells expresses a target antigen, the method comprising a) contacting the population of test cells with a population of T cells, wherein the T cells comprise nucleic acid encoding a reporter operably linked to a promoter and/or enhancer that is responsive to T cell activation; and b) contacting the population of T cells and test cells with the TDB, wherein the TDB comprises a target antigen-binding fragment and a TCS-binding fragment (such as a CD3-binding fragment), wherein expression of the reporter indicates the presence of the target antigen expressed by the test cell. In some embodiments, the reporter is a luciferase, a fluorescent protein, an alkaline phosphatase, a beta lactamase, or a beta galactosidase. In some embodiments, the luciferase is a firefly luciferase, a *Renilla* luciferase, or a nanoluciferase. In some embodiments, the promoter and/or enhancer responsive to T cell activation is an NFAT promoter, an AP-1 promoter, an NFκB promoter, a FOXO promoter, a STAT3 promoter, a STAT5 promoter or an IRF promoter. In some embodiments, the promoter and/or enhancer responsive to T cell activation comprises T cell activation responsive elements from any one or more of NFAT, AP-1, NFκB, FOXO, STAT3, STAT5 and IRF. In some embodiments, the population of T cells is a population of $CD4^+$ T cells or $CD8^+$ T cells. In some embodiments, the population of T cells is a population of Jurkat T cells or CTLL-2 T cells. In some embodiments, the TCS-binding fragment is a CD3-binding fragment. In some embodiments, the CD3-binding fragment is a CD3ε-binding fragment. In some embodiments, the target antigen is expressed on the surface of the target cells, in some embodiments, the target antigen is CD4, CD8, CD18, CD19, CD11a, CD11b, CD20, CD22, CD34, CD40, CD79α (CD79a), CD79β (CD79b), EGF receptor, HER2 receptor, HER3 receptor, HER4 receptor, FcRH5, CLL1, LFA-1, Mac1, p150, 95, VLA-4, ICAM-1, VCAM, αv/β3 integrin, VEGF, flk2/flt3 receptor; obesity (OB) receptor; mpl receptor; CTLA-4; protein C, BR3, c-met, tissue factor, β7, Tenb2, STEAP, or transmembrane tumor-associated antigens (TAA). In some embodiments, the population of test cells is a population of tumor cells, immune cells or vascular cells. In some embodiments, the population of test cells does not comprise T cells. In some embodiments, the ratio of T cells to test cells is about 1:1, about 1:2, about 1:3, about 1:4, about 1:5, about 1:6, about 1:7, about 1:8, about 1:9 or about 1:10. In some embodiments, the ratio of T cells to test cells is about 1:4. In some embodiments, the population of test cells and T cells comprises from about $1 \times 10^3$ to about $1 \times 10^6$ cells, in some embodiments, the population of test cells and T cells comprises from about $1 \times 10^4$ to about $5 \times 10^4$ cells.

In some embodiments, the population of test cells and T cells is contacted with a composition comprising the TDB at a concentration range of any of about 0.01 ng/mL to about 5000 ng/mL, about 0.05 ng/mL to about 5000 ng/mL, about 0.1 ng/mL to about 5000 ng/mL, about 0.5 ng/mL to about 5000 ng/mL, about 1 ng/mL to about 5000 ng/mL, about 5 ng/mL to about 5000 ng/mL, about 10 ng/mL to about 5000 ng/mL, about 0.01 ng/mL to about 4000 ng/mL, about 0.01 ng/mL to about 3000 ng/mL, about 0.01 ng/mL to about 2000 ng/mL, about 0.01 ng/mL to about 1000 ng/mL, about 0.01 ng/mL to about 500 ng/mL, about 0.01 ng/mL to about 100 ng/mL, about 0.01 ng/mL to about 50 ng/mL, about 0.01 ng/mL to about 10 ng/mL, about 0.01 ng/mL to about 5 ng/mL, about 0.1 ng/mL to about 1000 ng/mL, about 0.5 ng/mL to about 1000 ng/mL, about 1 ng/mL to about 100 ng/mL, about 1 ng/mL to about 1000 ng/mL, or about 5 ng/mL to about 5000 ng/mL.

In some embodiments, the reporter is detected after more than about any of 1 hr, 2 hr, 3 hr, 4 hr, 5 hr, 6 hr, 7 hr, 8 hr, 9 hr, 10 hr, 12 hr, 16 hr, 20 hr, or 24 hr after contacting the cells with the composition. In some embodiments, the reporter is detected between any of about 1 hr and about 24 hr, about 1 hr and about 12 hr, about 1 hr and about 8 hr, about 1 hr and about 6 hr, about 1 hr and about 4 hr, about 1 hr and about 2 hr, about 4 hr and about 24 hr, about 4 hr and about 12 hr, about 4 hr and about 8 hr, about 8 hr and about 24 hr, about 8 hr and about 12 hr, about 16 hr and about 24 hr, about 16 hr and about 20 hr, or about 20 hr and about 24 hr after contacting the cells with the composition.

E. Assay Development

The following is an exemplary but non-limiting method of developing a cell-based assay to detect TDB-mediated T cell activity.

DNA constructs: Lentivirus is used to generate the stable reporter T cell lines used to evaluate the potency of the TDB bi-specific antibody. Lentiviral vectors are constructed that express the reporter gene firefly luciferase, *Renilla* luciferase, or Nanoluciferase under the control of a minimal TK promoter regulated by DNA recognition elements for NFAT (Nuclear Factor of Activated T cells), AP-1 (Fos/Jun), MAT/AP1, NFκB, FOXO, STAT3/5, or IRF. The lentiviral expression cassettes used for the generation of the stable reporter cell lines may be third generation self-inactivating bi-cistronic vectors that express various antibiotic selection markers under the control of constitutive promoters/enhancers (EF1alpha or SV40) to enable the generation of stable cell lines. The reporter lentiviral vectors used are modified from the pCDH.MCS.EF1a. Puro commercially available vector (SBI biosciences; Cat No. CD510B-1). Promoter modifications include the removal of the CMV minimal promoter and substitution with various enhancer elements (NFAT, NFκB, etc.), addition of a minimal core RNA polymerase promoter (TATA box) from pRK5.CMV. Luciferase (Osaka, G et al., 1996 *J Pharm Sci.* 1996, 85:612-618), and substitution of different selection cassettes from internal DNAs (Neomycin resistance gene from pRK5.tk.neo, Hygromycin resistance gene from pRK5.tk.hygro, and the blasticidin resistance gene from pRK5.tk.blastocidin). Impact of the constitutive promoters used for selection on the activation of the enhancer elements is minimal due to the incorporation of a non-coding stretch of DNA designed to minimize promoter/enhancer cross-talk. Firefly Luciferase from pRK5.CMV.Luciferase (Osaka, 1996) is cloned into the HindIII-NotI site of the modified lentiviral parent vector. Other luminescent proteins including *Renilla* Luciferase and NanoLuciferase may also be subcloned into the HindIII-NotI site. Lentiviral packaging constructs (pCMV.HIVdelta, pCMC.VSV-G, and pCMV.Rev) used to generate viral stocks from transient transfection of 293s (293 suspension adapted cell line) cells may be obtained (pCMV.VSV-G) or generated (pCMV.HIVdelta, pCMV.REV). HIV strain MN (Nakamura, G R et al., 1993, *J. Virol.* 67(10):6179-6191) may be used to generate the pCMV.HIVdelta packaging vector and contains an internal EcoRI partial digest deletion to inactivate by deletion the HIV viral envelope and modifications to the 5' and 3'LTRs for safety purposes. HIV Rev is cloned from pCMV.HIVdelta transfected 293s cell RNA by RT-PCR and introduced into the ClaI-Xho site of pRK5.tk.neo. The use of VSV-G to pseudotype the lentiviral reporters (substituting VSV-G for HIV env) enables the infection of any cell type. Lentiviral expression plasmids and packaging constructs are amplified in Stbl2 competent cells (Life Technologies, Cat. No. 10268-019) and DNA purified using Qiagen Maxi Prep kit (Cat. No. 12662). All DNA constructs are confirmed by DNA sequencing.

Reporter gene assay cell line development: Jurkat CD4+ T cell line (DSMZ, Cat. No. ACC 282) and CTLL-2 CD8+ cell line (Life Technologies, Cat. No. K1653) are used to evaluate the feasibility of a reporter gene assay to monitor the activation of T cells by the TDB. Lentiviral vectors are constructed that express the reporter gene firefly luciferase, *Renilla* luciferase, or Nanoluciferase under the control of a minimal TK promoter regulated by DNA recognition elements for NFAT (Nuclear Factor of Activated T cells), AP-1 (Fos/Jun), NFAT/AP1, NFκB, FOXO, STAT3,5, and IRF. Reporter gene viral stocks are generated by transient transfection of 293s cells and pseudotyped with VSV-G, concentrated, and titered using standard methods (Naldini, L., et al, 1996 *Science,* 272:263-267). The Jurkat CTLL-2 cells are infected with the lentiviral reporter viral stock at an MOI of 10 by spinoculation and after 3 days infected cells are selected for antibiotic resistance. After 2 weeks, stable pools are generated and evaluated for the response to purified TDB. A qPCR method that evaluates copy number and integration is used to demonstrate that all stable pools are stably infected with the reporter constructs. On the basis of these experiments, limiting dilution of Jurkat/NFκB-luciferase and Jurkat/NFAT-Luciferase are set up to enable single cell cloning and generation of single stable reporter cell lines.

Development and evaluation of the T cell activation assay: To quantitate the potency of TDB-mediated T cell activation, the amount of luciferase activity observed for a plurality of dilutions of a TDB test sample incubated with a population of Jurkat/NFκB-fireflyLuciferase effector cells and target cells is compared to the luciferase activity observed for a reference TDB. The relative potency of the test TDB samples is determined from the standard curve generated by using the reference TDB.

III. Non Cell-Based Reporter Assays

The present invention in some aspects provides non cell-based assays to detect simultaneous TDB binding of a target antigen and a TCS (such as a CD3 subunit), wherein one antigen binding fragment of the TDB binds the target antigen and the other antigen binding fragment binds the TCS. Simultaneous binding of the TDB to a T cell receptor (TCR) complex subunit (such as a CD3 subunit, e.g., CD3ε) and to a target antigen expressed on the surface of a target cell results in TCR clustering, leading to T cell activation and the cytotoxic depletion of the target cell. These non cell-based assays serve as a surrogate measure of T cell activation.

In some embodiments, the invention provides methods of detecting simultaneous binding of a TDB to a target antigen and a TCS (such as a CD3 subunit), wherein one antigen binding fragment of the TDB hinds a first epitope on the target antigen and the other antigen binding fragment binds a second epitope on the TCS, the method comprising performing an ELISA-based bridging binding assay using immobilized target antigen, or a fragment thereof comprising the first epitope, and a conjugate of biotin and the TCS, or a fragment thereof comprising the second epitope. In some embodiments, the first epitope is localized to an extracellular portion of the target antigen and/or the second epitope is localized to an extracellular portion of the TCS.

In some embodiments, the invention provides methods of detecting simultaneous binding of a TDB to a target antigen and a TCS (such as a CD3 subunit), wherein one antigen binding fragment of the TDB binds a first epitope on the target antigen and the other antigen binding fragment binds a second epitope on the TCS, the method comprising a) immobilizing the target antigen, or a fragment thereof comprising the first epitope, to a solid phase; b) incubating the TDB with the target antigen, or fragment thereof comprising the first epitope, immobilized to the solid phase; c) incubating the TDB with a conjugate of a reporter molecule and the TCS, or a fragment thereof comprising the second epitope (biotin-TCS conjugate); d) optionally incubating the reporter-TCS conjugate with an accessory molecule needed to detect the reporter molecule; e) removing molecules unbound to the solid phase (such as by washing); and f) detecting the reporter molecule bound to the solid phase using a detection agent, thereby detecting simultaneous binding of the TDB to the target antigen and the TCS. In some embodiments, the invention provides methods of detecting simultaneous binding of a TDB to a target antigen and a TCS (such as a CD3 subunit), wherein one antigen binding fragment of the TDB binds a first epitope on the target antigen and the other antigen binding fragment binds a second epitope on the TCS, the method comprising a) immobilizing the target antigen, or a fragment thereof comprising the first epitope, to a solid phase; b) incubating the TDB with the target antigen, or fragment thereof comprising the first epitope, immobilized to the solid phase; c) incubating the TDB with a conjugate of biotin and the TCS, or a fragment thereof comprising the second epitope (biotin-TCS conjugate); d) incubating the biotin-TCS conjugate with a streptavidin-HRP conjugate; e) removing molecules unbound to the solid phase (such as by washing); and f) detecting HRP bound to the solid phase using a detection agent, thereby detecting simultaneous binding of the TDB to the target antigen and the TCS. Washing steps may be included between the incubation steps to remove molecules unbound to the solid phase. In some embodiments, the incubation steps are independently carried out for about any of 1 hr, 2 hr, 3 hr, 4 hr, 5 hr, 6 hr, 7 hr, 8 hr, 9 hr, 10 hr, 12 hr, 16 hr, 20 hr, 24 hr, or more, including any ranges between these values. In some embodiments, the TCS is a CD3 subunit. In some embodiments, the CD3 subunit is CD3ε. In some embodiments, the target antigen is expressed on the surface of a cell. In some embodiments, the target antigen is CD4, CD8, CD18, CD19, CD11a, CD11b, CD20, CD22, CD34, CD40, CD79α (CD79a), CD79β (CD79b), EGF receptor, HER2 receptor, HER3 receptor, HER4 receptor, FcRH5, CLL1, LFA-1, Mac1, p150, 95, VLA-4, ICAM-1, VCAM, αv/β3 integrin, VEGF, flk2/flt3 receptor; obesity (OB) receptor; mpl receptor; CTLA-4; protein C, BR3, c-met, tissue factor, β7, Tenb2, STEAP, or transmembrane tumor-associated antigens (TAA). In some embodiments, the first epitope is localized to an extracellular portion of the target antigen and/or the second epitope is localized to an extracellular portion of the TCS.

In some embodiments, the TDB included in an incubation step is at a concentration range of any of about 0.01 ng/mL to about 100 µg/mL, about 005 ng/mL to about 100 µg/mL, about 0.1 ng/mL, to about 100 µg/mL, about 0.5 ng/mL to about 100 µg/mL, about 1 ng/mL, to about 100 µg/mL, about 5 ng/mL to about 100 µg/mL, about 10 ng/mL to about 100 µg/mL, about 0.01 ng/mL to about 50 µg/mL, about 0.01 ng/mL to about 10 µg/mL, about 0.01 to about 1 µg/mL, about 0.01 ng/mL to about 100 ng/mL, about 0.01 ng/mL, to about 50 ng/mL, about 0.01 ng/mL to about 10 ng/mL, about 0.01 ng/mL to about 0.1 ng/mL, about 0.01 ng/mL to about 0.05 ng/mL, about 0.01 ng/mL to about 0.05 ng/mL, about 0.1 ng/mL to about 1 µg/mL, about 0.5 ng/mL to about 1 µg/mL to about 1 ng/mL to about 100 ng/mL, about 1 ng/mL, to about 1 µg/mL, or about 5 ng/mL, to about 5 µg/mL.

In some embodiments, the invention provides methods of quantifying simultaneous binding of a TDB to a target antigen and a TCS (such as a CD3 subunit), wherein one antigen binding fragment of the TDB binds a first epitope on the target antigen and the other antigen binding fragment binds a second epitope on the TCS, the method comprising a) immobilizing the target antigen, or a fragment thereof comprising the first epitope, to a solid phase; b) incubating the TDB with the target antigen, or fragment thereof comprising the first epitope, immobilized to the solid phase; incubating the TDB with a conjugate of a reporter and the TCS, or a fragment thereof comprising the second epitope (e.g., biotin-TCS conjugate); d) optionally incubating the reporter-TCS conjugate with an accessory reporter molecule; e) removing molecules unbound to the solid phase (such as by washing); f) detecting reporter bound to the solid phase using a detection agent; and g) determining the relative potency of the TDB by comparing the signal intensity of the detection agent to a standard generated using a reference TDB. In some embodiments, the invention provides methods of quantifying simultaneous binding of a TDB to a target antigen and a TCS (such as a CD3 subunit), wherein one antigen binding fragment of the TDB binds a first epitope on the target antigen and the other antigen binding fragment binds a second epitope on the TCS, the method comprising a) immobilizing the target antigen, or a fragment thereof comprising the first epitope, to a solid phase; b) incubating the TDB with the target antigen, or fragment thereof comprising the first epitope, immobilized to the solid phase; c) incubating the TDB with a conjugate of biotin and the TCS, or a fragment thereof comprising the second epitope (biotin-TCS conjugate); d) incubating the biotin-TCS conjugate with a streptavidin-HRP conjugate; e) removing molecules unbound to the solid phase (such as by washing); f) detecting HRP bound to the solid phase using a detection agent; and g) determining the relative potency of the TDB by comparing the signal intensity of the detection agent to a standard generated using a reference TDB. In some embodiments, comparing the signal intensity comprises generating a dose-response curve for each of the TDB and the reference TDB, and determining the ratio between the $EC_{50}$ values derived from the curves. Washing steps may be included between the incubation steps to remove molecules unbound to the solid phase. In some embodiments, the incubation steps are independently carried out for about any of 1 hr, 2 hr, 3 hr, 4 hr, 5 hr, 6 hr, 7 hr, 8 hr, 9 hr, 10 hr, 12 hr, 16 hr, 20 hr, 24 hr, or more, including any ranges between these values. In some embodiments, the TCS is a CD3 subunit. In some embodiments, the CD3 subunit is CD3ε. In some embodiments, the target antigen is expressed on the surface of a cell. In some embodiments, the target antigen is CD4, CD8, CD18, CD19, CD11a, CD11b, CD20, CD22, CD34, CD40, CD79 (CD79a), CD79β (CD79b), EGF receptor, HER2 receptor. HER3 receptor, HER4 receptor, FcRH5, CLL1, Mac1, p150, 95, VLA-4, ICAM-1, VCAM, αv/β3 integrin, VEGF, flk2/flt3 receptor; obesity (OB) receptor; mpl receptor; CTLA-4; protein C, BR3, c-met, tissue factor, β7, Tenb2, STEAP, or transmembrane tumor-associated antigens (TAA). In some embodiments, the first epitope is localized to an extracellular portion of the target antigen and/or the second epitope is localized to an extracellular portion of the TCS.

In some embodiments, the TDB included in an incubation step is at a concentration range of any of about 0.01 ng/mL to about 100 μg/mL, about 0.05 ng/mL to about 100 μg/mL, about 0.1 ng/mL to about 100 μg/mL, about 0.5 ng/mL to about 100 μg/mL, about 1 ng/mL, to about 100 μg/mL about 5 ng/mL to about 100 μg/mL, about 10 ng/mL to about 100 μg/mL, about 0.01 ng/mL, to about 50 μg/mL, about 0.01 ng/mL to about 10 μg/mL, about 0.01 ng/mL to about 1 μg/mL, about 0.01 ng/mL to about 100 ng/mL, about 0.01 ng/mL to about 50 ng/mL, about 0.01 ng/mL to about 10 ng/mL, about 0.01 ng/mL to about 0.1 ng/mL, about 0.01 ng/mL to about 0.05 ng/mL, about 0.01 ng/mL to about 0.05 ng/mL, about 0.1 ng/mL to about 1 μg/mL, about 0.5 ng/mL to about 1 ng/mL about 1 ng/mL to about 100 ng/mL, about 1 ng/mL to about 1 μg/mL, or about 5 ng/mL to about 5 μg/mL.

In some embodiments, the standard curve from the reference TDB is generated by incubating the reference TDB at a plurality of concentrations ranging from about any one of 0.01 ng/mL to 100 μg/mL. In some embodiments, the plurality of concentrations of reference TDB include about any one of 0.01 ng/ml, 0.1 ng/ml, 1 ng/ml, 10 ng/ml, 100 ng/mL, 250 ng/mL, 500 ng/mL, 1 μg/mL, 2.5 μg/mL, 5 μg/mL, 10 μg/mL, 25 μg/mL, 50 μg/mL, 100 μg/mL, 250 μg/mL, or 500 μg/mL. In some embodiments, the plurality of concentrations of reference TDB is about three, four, five, six, seven, eight, nine, ten or more than ten concentrations.

IV. Kits

In some aspects of the invention, a kit or article of manufacture is provided for use in various methods involving a TDB comprising a target antigen-binding fragment and a TCS-binding fragment (such as a CD3-binding fragment), comprising a container which holds a composition comprising engineered T cells comprising nucleic acid encoding a reporter operably linked to a promoter and/or enhancers that are responsive to T cell activation as described herein, and optionally provides instructions for its use. In some embodiments, the kit further comprises a container which holds a reference TDB assay standard (a purified TDB of known concentration), and/or a container which holds a TDB control. In some embodiments, the kit further comprises a container which holds a composition comprising target cells expressing the target antigen. In some embodiments, the reporter is a luciferase, a fluorescent protein, an alkaline phosphatase, a beta lactamase, or a beta galactosidase. In some embodiments, the luciferase is a firefly luciferase, a *Renilla* luciferase, or a nanoluciferase. In some embodiments, the promoter and/or enhancer responsive to T cell activation is an NFAT promoter, an AP-1 promoter, an NFκB promoter, a FOXO promoter, a STAT3 promoter, a STAT5 promoter or an IRF promoter. In some embodiments, the promoter and/or enhancer responsive to T cell activation comprises T cell activation responsive elements from any one or more of NFAT, AP-1, NFκB, FOXO, STAT3, STAT5 and IRF. In some embodiments, the engineered T cells are $CD4^+$ T cells or $CD8^+$ T cells. In some embodiments, the engineered T cells are Jurkat T cells or CTLL-2 T cells. In some embodiments, the TCS-binding fragment is a CD3-binding fragment. In some embodiments, the CD3-binding fragment is a CD3ε-binding fragment. In some embodiments, the target antigen is expressed on the surface of the target cells. In some embodiments, the target antigen is CD4, CD8, CD 18, CD19, CD11a, CD11b, CD20, CD22, CD34, CD40, CD79α (CD79a), CD79β (CD79b), EGF receptor, HER2 receptor, HER3 receptor, HER4 receptor, FcRH5, CLL1, LFA-1, p150, 95, VLA-4, ICAM-1, VCAM, αv/β3 integrin, VEGF, flk2/flt3 receptor; obesity (OB) receptor; mpl receptor; CTLA-4; protein C, BR3, c-met, tissue factor, β7, Tenb2, STEAP, or transmembrane tumor-associated antigens (TAA). In some embodiments, a) the target antigen is HER2 receptor and the target cell is a BT-474 cell, b) the target antigen is HER2 receptor and the target cell is a SKBR3 cell, c) the target antigen is CD20 and the target cell is a Wil2-S cell, or d) the target antigen is CD79b and the target cell is a BJAB cell. The containers hold the formulations and the labels on, or associated with, the containers may indicate directions for use. The article of manufacture may further include other materials desirable from a commercial and user standpoint, including other buffers, diluents, cultureware, reagents for detecting reporter molecules, and package inserts with instructions for use.

In some aspects of the invention, a kit or article of manufacture is provided comprising a container which holds a composition comprising a TCS (such as a CD3 subunit), or a fragment thereof, conjugated with biotin, and optionally provides instructions for its use. In some embodiments, the TCS is a CD3 subunit. In some embodiments, the CD3 subunit is CD3ε. In some embodiments, the kit further provides a target antigen, or a fragment thereof. In some embodiments, the target antigen is expressed on the surface of a cell. In some embodiments, the target antigen is CD4, CD8, CD18, CD19, CD11a, CD11b, CD20, CD22, CD34, CD40, CD79α (CD79a), CD79β (CD79b), EGF receptor, HER2 receptor, HER3 receptor, HER4 receptor, FcRH5, CTLL1, LFA-1, Mac1, p150, 95, VLA-4, ICAM-1, VCAM, αv/β3 integrin, VEGF, flk2/flt3 receptor; obesity (OB) receptor; mpl receptor; CTLA-4; protein C, BR3, c-met, tissue factor, β7, Tenb2, STEAP, or transmembrane tumor-associated antigens (TAA). In some embodiments, the kit further provides a reference TDB assay standard (a purified TDB of known concentration), and/or a TDB control. The containers hold the formulations and the labels on, or associated with, the containers may indicate directions for use. The article of manufacture may further include other materials desirable from a commercial and user standpoint, including other buffers, diluents, cultureware, reagents for detecting reporter molecules, and package inserts with instructions for use.

VI. Polypeptides

The polypeptides to be analyzed using the methods described herein are generally produced using recombinant techniques. Methods for producing recombinant proteins are described, e.g., in U.S. Pat. Nos. 5,534,615 and 4,816,567, specifically incorporated herein by reference. In some embodiments, the protein of interest is produced in a CHO cell (see, e.g. WO 94/11026). In some embodiments, the polypeptide of interest is produced in an *E. coli* cell. See, e.g., U.S. Pat. Nos. 5,648,237; 5,789,199; 5,840,523, which describes translation initiation region (TIR) and signal sequences for optimizing expression and secretion. See also Charlton, Methods in Molecular Biology, Vol. 248 (B. K. C. Lo, ed., Humana Press, Totowa, N.J., 2003), pp. 245-254, describing expression of antibody fragments in *E. coli*. When using recombinant techniques, the polypeptides can be produced intracellularly, in the periplasmic space, or directly secreted into the medium.

The polypeptides may be recovered from culture medium or from host cell lysates. Cells employed in expression of the polypeptides can be disrupted by various physical or chemical means, such as freeze-thaw cycling, sonication, mechanical disruption, or cell lysing agents. If the polypeptide is produced intracellularly, as a first step, the particulate debris, either host cells or lysed fragments, are removed, for example, by centrifugation or ultrafiltration. Carter et al., *Bio/Technology* 10: 163-167 (1992) describe a procedure for isolating polypeptides which are secreted to the periplasmic space of *E. coli*. Briefly, cell paste is thawed in the presence of sodium acetate (OH 3.5), EDTA, and phenylmethylsulfonylfluoride (PMSF) over about 30 min. Cell debris can be removed by centrifugation. Where the polypeptide is secreted into the medium, supernatants from such expression systems are generally first concentrated using a commercially available polypeptide concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

In some embodiments, the polypeptide in the composition comprising the polypeptide and one or more contaminants has been purified or partially purified prior to analysis by the methods of the invention. For example, the polypeptide of the methods is in an eluent from an affinity chromatography, a cation exchange chromatography, an anion exchange chromatography, a mixed mode chromatography and a hydrophobic interaction chromatography. In some embodiments, the polypeptide is in an eluent from a Protein A chromatography.

Examples of polypeptides that may be analyzed by the methods of the invention include but are not limited to immunoglobulins, immunoadhesins, antibodies, enzymes, hormones, fusion proteins, Fc-containing proteins, immunoconjugates, cytokines and interleukins.

(A) Antibodies

In some embodiments of any of the methods described herein, the polypeptide for use in any of the methods of analyzing polypeptides and formulations comprising the polypeptides by the methods described herein is an antibody. In some embodiments, the polypeptide is a T cell-dependent bispecific (TDB) antibody.

Molecular targets for antibodies include CD proteins and their ligands, such as, but not limited to: (i) CD3, CD4, CD8, CD19, CD11a, CD20, CD22, CD34, CD40, CD79α (CD79a), and CD79β (CD79b); (ii) members of the ErbB receptor family such as the EGF receptor, HER2, HER3 or HER4 receptor; (iii) cell adhesion molecules such as LFA-1, Mac1, p150,95, VLA-4, ICAM-1, VCAM and αv/β3 integrin, including either alpha or beta subunits thereof (e.g, anti-CD11a, anti-CD18 or anti-CD11b antibodies); (iv) growth factors such as VEGF; IgE; blood group antigens; flk2/flt3 receptor; obesity (OB) receptor; mpl receptor; CTLA-4; protein C, BR3, c-met, tissue factor, β7 etc; (v) cell surface and transmembrane tumor-associated antigens (TAA), such as those described in U.S. Pat. No. 7,521,541, and (vi) other targets such as FcRH5, TenB2 and STEAP. In some embodiments, the antibody is an anti-CD2O/anti-CD3 antibody. Exemplary bispecific antibodies are provided in Table 1.

TABLE 1

Exemplary antibodies

| CD3 Arm | Type | Seq |
|---|---|---|
| 40G5c | HVR-H1 | NYYIH (SEQ ID NO: 1) |
|  | HVR-H2 | WIYPGDGNTKYNEKFKG (SEQ ID NO: 2) |
|  | HVR-H3 | DSYSNYYFDY (SEQ ID NO: 3) |
|  | HVR-L1 | KSSQSLLNSRTRKNYLA (SEQ ID NO: 4) |
|  | HVR-L2 | WASTRES (SEQ ID NO: 5) |
|  | HVR-L3 | TQSFILRT (SEQ ID NO: 6) |
| 38E4v1 | HVR-H1 | SYYIH (SEQ ID NO: 7) |
|  | HVR-H2 | WIYPENDNTKYNEKFKD (SEQ ID NO: 8) |
|  | HVR-H3 | DGYSRYYFDY (SEQ ID NO: 9) |
|  | HVR-L1 | KSSQSLLNSRTRKNYLA (SEQ ID NO: 10) |
|  | HVR-L2 | WTSTRKS (SEQ ID NO: 11) |
|  | HVR-L3 | KQSFILRT (SEQ ID NO: 12) |
| UCHT1v9 | HVR-H1 | GYTMN (SEQ ID NO: 13) |
|  | HVR-H2 | LINPYKGVSTYNQKFKD (SEQ ID NO: 14) |
|  | HVR-H3 | SGYYGDSDWYFDV (SEQ ID NO: 15) |
|  | HVR-L1 | RASQDIRNYLN (SEQ ID NO: 16) |
|  | HVR-L2 | YTSRLES (SEQ ID NO: 17) |
|  | HVR-L3 | QQGNTLPWT (SEQ ID NO: 18) |

TABLE 1-continued

Exemplary antibodies

| CD3 Arm | Type | Seq |
|---|---|---|
| 40G5c | VH (hu) | EVQLVQSGAEVKKPGASVKVSCKASGYTFTNYYIHWVRQAPGQGL EWIGWIYPGDGNTKYNEKFKGRATLTADTSTSTAYLELSSLRSEDTA VYYCARDSYSNYYFDYWGQGTLVTVSS (SEQ ID NO: 19) |
| | VL (hu) | DIVMTQSPDSLAVSLGERATINCKSSQSLLNSRTRKNYLAWYQQKP GQPPKLLIYWASTRESGVPDRFSGSGSGTDFTLTISSLQAEDVAVYY CTQSFILRTFGQGTKVEIK (SEQ ID NO: 20) |
| 38E4v1 | VH (hu) | EVQLVQSGAEVKKPGASVKVSCKASGFTFTSYYIHWVRQAPGQGL EWIGWIYPENDNTKYNEKFKDRVTITADTSTSTAYLELSSLRSEDTA VYYCARDGYSRYYFDYWGQGTLVTVSS (SEQ ID NO: 21) |
| | VL (hu) | DIVMTQSPDSLAVSLGERATINCKSSQSLLNSRTRKNYLAWYQQKP GQSPKLLIYWISTRKSGVPDRFSGSGSGTDFTLTISSLQAEDVAVYY CKQSFILRTFGQGTKVEIK (SEQ ID NO: 22) |
| UCHT1v9 | VH (hu) | EVQLVESGGGLVQPGGSLRLSCAASGYSFTGYTMNWVRQAPGKD LEWVALINPYKGVSTYNQKFKDRFTISVDKSKNTAYLQMNSLRAEDT AVYYCARSGYYGDSDWYFDVWGQGTLVTVSS (SEQ ID NO:23) |
| | VL (hu) | DIQMTQSPSSLSASVGDRVTITCRASQDIRNYLNWYQQKPGKAPKL LIYYTSRLESGVPSRFSGSGSGTDYTLTISSLQPEDFATYYCQQGNT LPWTFGQGTKLELK (SEQ ID NO: 24) |
| Target Arm | | |
| 2h7 v 16 CD20 | HVR-H1 | GYTFTSYNMH (SEQ ID NO: 25) |
| | HVR-H2 | AIYPGNGDTSYNQKFKG (SEQ ID NO: 26) |
| | HVR-H3 | VVYYSNSYWYFDV (SEQ ID NO: 27) |
| | HVR-L1 | RASSSVSYMH (SEQ ID NO: 28) |
| | HVR-L2 | APSNLAS (SEQ ID N0: 29) |
| | HVR-L3 | QQWSFNPPT (SEQ ID NO: 30) |
| 2h7 v 16 | VH | EVQLVESGGGLVQPGGSLRLSCAAS GYTFTSYNMH WVRQA PGKGLEWVG AIYPGNGDTSYNQKFKG RFTISVDKSKNTLYL QMNSLRAEDTAVYYCAR VVYYSNSYWYFDV WGQGTLVTVSS (SEQ ID NO: 31) |
| | VL | DIQMTQSPSSLSASVGDRVTITC RASSSVSYMH WYQQKP GKAPKPLIY APSNLAS GVPSRFSGSGSGTDFILTISSLQP EDFATYYC QQWSFNPPT FGQGTKVEIKR (SEQ ID NO: 32) |
| 4D5 Her2 | HVR-H1 | DTYIH (SEQ ID NO: 33) |
| | HVR-H2 | RIYPTNGYTRYADSVKG (SEQ ID NO: 34) |
| | HVR-H3 | WGGDGFYAMDY (SEQ ID NO: 35) |
| | HVR-L1 | RASQDVNTAVA (SEQ ID NO: 36) |
| | HVR-L2 | SASFLYS (SEQ ID NO: 37) |
| | HVR-L3 | QQHYTTPPT (SEQ ID NO: 38) |
| 4D5 | VH (hu) | EVQLVESGGGLVQPGGSLRLSCAASGFNIKDTYIHWVRQA PGKGLEWVARIYPTNGYTRYADSVKGRFTISADTSKNTAYL QMNSLRAEDTAVYYCSRWGGDGFYAMDYWGQGTLVTVSS (SEQ ID NO: 39) |
| | VL (hu) | DIQMTQSPSSLSASVGDRVTITCRASQDVNTAVAWYQQKP GKAPKLLIYSASFLYSGVPSRFSGSRSGTDFTLTISSLQPE DFATYYCQQHYTTPPTFGQGTKVEIK (SEQ ID NO: 40) |

Other exemplary antibodies include those selected from, and without limitation, anti-estrogen receptor antibody, anti-progesterone receptor antibody, anti-p53 antibody, anti-HER-2/neu antibody, anti-EGFR antibody, anti-cathepsin D antibody, anti-Bcl-2 antibody, anti-E-cadherin antibody, anti-CA125 antibody, anti-CA15-3 antibody, anti-CA19-9 antibody, anti-c-erbB-2 antibody, anti-P-glycoprotein antibody, anti-CEA antibody, anti-retinoblastoma protein antibody, anti-ras oncoprotein antibody, anti-Lewis X antibody, anti-Ki-67 antibody, anti-PCNA antibody, anti-CD3 antibody, anti-CD4 antibody, anti-CD5 antibody, anti-CD7 antibody, anti-CD8 antibody, anti-CD9/p24 antibody, anti-CD10 antibody, anti-CD11a antibody, anti-CD11c antibody, anti-CD13 antibody, anti-CD14 antibody, anti-CD15 antibody, anti-CD19 antibody, anti-CD20 antibody, anti-CD22 antibody, anti-CD23 antibody, anti-CD30 antibody, anti-CD31 antibody, anti-CD33 antibody, anti-CD34 antibody, anti-CD35 antibody, anti-CD38 antibody, anti-CD41 antibody, anti-LCA/CD45 antibody, anti-CD45RO antibody, anti-CD45RA antibody, anti-CD39 antibody, anti-CD100 antibody, anti-CD95/Fas antibody, anti-CD99 antibody, anti-CD106 antibody, anti-ubiquitin antibody, anti-CD71 antibody, anti-c-myc antibody, anti-cytokeratins antibody, anti-vimentin antibody, anti-HPV proteins antibody, anti-kappa light chains antibody, anti-lambda light chains antibody, anti-melanosomes antibody, anti-prostate specific antigen antibody, anti-S-100 antibody, anti-tau antigen antibody, anti-fibrin antibody, anti-keratins antibody, anti-TebB2 antibody, anti-STEAP antibody, and anti-Tn-antigen antibody.

(i) Monoclonal Antibodies

In some embodiments, the antibodies are monoclonal antibodies. Monoclonal antibodies are obtained from a population of substantially homogeneous antibodies, i.e., the individual antibodies comprising the population are identical and/or bind the same epitope except for possible variants that arise during production of the monoclonal antibody, such variants generally being present in minor amounts. Thus, the modifier "monoclonal" indicates the character of the antibody as not being a mixture of discrete or polyclonal antibodies.

For example, the monoclonal antibodies may be made using the hybridoma method first described by Kohler et al., *Nature* 256:495 (1975), or may be made by recombinant DNA methods (U.S. Pat. No. 4,816,567).

In the hybridoma method, a mouse or other appropriate host animal, such as a hamster, is immunized as herein described to elicit lymphocytes that produce or are capable of producing antibodies that will specifically bind to the polypeptide used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

In some embodiments, the myeloma cells are those that fuse efficiently, support stable high-level production of antibody by the selected antibody-producing cells, and are sensitive to a medium such as HAT medium. Among these, in some embodiments, the myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.* 133:3001 (1984); Brodeur et al., *Monoclonal Antibody Production Techniques and Applications* pp. 51-63 (Marcel Dekker, Inc., New York, 1987)).

Culture medium in which hybridoma cells are growing is assayed for production of monoclonal antibodies directed against the antigen. In some embodiments, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.* 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice* pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, polypeptide A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). In some embodiments, the hybridoma cells serve as a source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce immunoglobulin polypeptide, to obtain the synthesis of monoclonal antibodies in the recombinant host cells. Review articles on recombinant expression in bacteria of DNA encoding the antibody include Skerra et al., *Curr. Opinion in Immunol.* 5:256-262 (1993) and Plückthun, *Immunol. Revs.*, 130:151-188 (1992).

In a further embodiment, antibodies or antibody fragments can be isolated from antibody phage libraries generated using the techniques described in McCafferty et al., *Nature* 348:552-554 (1990). Clackson et al., *Nature* 352:624-628 (1991) and Marks et al., *J. Mol. Biol.* 222:581-597 (1991) describe the isolation of murine and human antibodies, respectively, using phage libraries. Subsequent publications describe the production of high affinity (nM range) human antibodies by chain shuffling (Marks et al., *Bio/Technology* 10:779-783 (1992)), as well as combinatorial infection and in vivo recombination as a strategy for constructing very large phage libraries (Waterhouse et al., *Nuc. Acids. Res.* 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light chain constant domains in place of the homologous murine sequences (U.S. Pat. No. 4,816,567; Morrison et al., *Proc. Natl Acad. Sci. USA* 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

In some embodiments of any of the methods described herein, the antibody is IgA, IgD, IgE, IgG, or IgM. In some embodiments, the antibody is an IgG monoclonal antibody.

(ii) Humanized Antibodies

In some embodiments, the antibody is a humanized antibody. Methods for humanizing non-human antibodies have been described in the art. In some embodiments, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et at., *Nature* 321:522-525 (1986); Riechmann et al., *Nature* 332:323-327 (1988); Verhoeyen et al., *Science* 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence that is closest to that of the rodent is then accepted as the human framework region (FR) for the humanized antibody (Sims et al. *J. Immunol.* 151:2296 (1993): Chothia et al., *J. Mol. Biol.* 196:901 (1987)). Another method uses a particular framework region derived from the consensus sequence of all human antibodies of a particular subgroup of light or heavy chain variable regions. The same framework may be used for several different humanized antibodies (Carter et at., *Proc. Natl. Acad. Sci. USA* 89:4285 (1992); Presta et al., *J. Immunol.* 151:2623 (1993)).

It is further important that antibodies be humanized with retention of high affinity for the antigen and other favorable biological properties. To achieve this goal, in some embodiments of the methods, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

(iii) Human Antibodies

In some embodiments, the antibody is a human antibody. As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA* 90:2551 (1993); Jakobovits et al., *Nature* 362:255-258 (1993); Bruggermann et al., *Year in Immuno.* 7:33 (1993); and U.S. Pat. Nos. 5,591,669; 5,589,369; and 5,545,807.

Alternatively, phage display technology (McCafferty et al., *Nature* 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat polypeptide gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell, Phage display can be performed in a variety of formats; for their review see, e.g., Johnson, Kevin S. and Chiswell, David J., *Current Opinion in Structural Biology* 3:564-571 (1993). Several sources of V-gene segments can be used for phage display. Clackson et al., *Nature* 352:624-8 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See also, U.S. Pat. Nos. 5,565,332 and 5,573,905.

Human antibodies may also be generated by in vitro activated B cells (see U.S. Pat. Nos. 5,567,610 and 5,229,275).

(iv) Antibody Fragments

In some embodiments, the antibody is an antibody fragment. Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992) and Brennan et al., *Science* 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form $F(ab')_2$ fragments (Carter et al., *Bio/Technology* 10:163-167 (1992)). According to another approach. $F(ab')_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. Nos. 5,571,894; and 5,587,458. The antibody fragment may also be a "linear antibody," e.g., as described in U.S. Pat. No. 5,641,870 for example. Such linear antibody fragments may be monospecific or bispecific.

In some embodiments, fragments of the antibodies described herein are provided. In some embodiments, the antibody fragment is an antigen binding fragment. In some embodiments, the antigen binding fragment is selected from the group consisting of a Fab fragment, a Fab' fragment, a $F(ab')_2$ fragment, a scFv, a Fv, and a diabody.

Bispecfic Antibodies

In some embodiments, the antibody is a bispecific antibody. Bispecific antibodies are antibodies that have binding specificities for at least two different epitopes. Exemplary bispecific antibodies may hind to two different epitopes. Alternatively, a bispecific antibody binding arm may be combined with an arm that binds to a triggering molecule on a leukocyte such as a T-cell receptor molecule (e.g. CD2 or CD3), or Fc receptors for IgG (FcγR), such as FcγRI (CD64), FcγRII (CD32) and FcγRIII (CD16) so as to focus cellular defense mechanisms to the cell. Bispecific antibodies can be prepared as full length antibodies or antibody fragments (e.g. F(ab')$_2$ bispecific antibodies). In some embodiments, the antibody is a T cell-dependent bispecific (TDB) antibody. In some embodiments, the TDB comprises a target antigen binding fragment and a T cell receptor binding fragment. In some embodiments, the TDB comprises a target antigen binding fragment and a CD3 binding fragment. In some embodiments, the TDB comprises a target antigen binding fragment and a CD3ε binding fragment.

Methods for making bispecific antibodies are known in the art. Traditional production of full length bispecific antibodies is based on the coexpression of two immunoglobulin heavy chain-light chain pairs, where the two chains have different specificities (Millstein et al., *Nature* 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655-3659 (1991).

According to a different approach, antibody variable domains with the desired binding specificities (antibody-antigen combining sites) are fused to immunoglobulin constant domain sequences. In some embodiments, the fusion is with an immunoglobulin heavy chain constant domain, comprising at least part of the hinge, CH2, and CH3 regions. In some embodiments, the first heavy chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In some embodiments of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology* 121:210 (1986).

According to another approach described in U.S. Pat. No. 5,731,168, the interface between a pair of antibody molecules can be engineered to maximize the percentage of heterodimers that are recovered from recombinant cell culture. In some embodiments, the interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science* 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Various techniques for making and isolating bispecific antibody fragments directly from recombinant cell culture have also been described. For example, bispecific antibodies have been produced using leucine zippers. Kostelny et al., *J. Immunol.* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444-6448 (1993) has provided an alternative mechanism for making bispecific antibody fragments. The fragments comprise a heavy chain variable domain ($V_H$) connected to a light chain variable domain ($V_L$) by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.* 152:5368 (1994).

Antibodies with more than two valencies are contemplated. For example, trispecific antibodies can be prepared. Tutt et al., *J. Immunol.* 147: 60 (1991).

(i) Multivalent Antibodies

In some embodiments, the antibodies are multivalent antibodies. A multivalent antibody may be internalized (and/or catabolized) faster than a bivalent antibody by a cell expressing an antigen to which the antibodies bind. The antibodies provided herein can be multivalent antibodies (which are other than of the IgM class) with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)n-VD2-(X2) n-Fc, wherein VD1 is a first variable domain, VD2 is a second variable domain. Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain. In some embodiments, the multivalent antibody comprises a T cell binding fragment. In some embodiments, the multivalent antibody comprises a T cell receptor binding fragment. In some embodiments, the multivalent antibody comprises a CD3 binding fragment. In some embodiments, the multivalent antibody comprises a CD3ε binding fragment.

In some embodiments, the antibody is a multispecific antibody. Example of multispecific antibodies include, but are not limited to, an antibody comprising a heavy chain variable domain ($V_H$) and a light chain variable domain ($V_L$) where the $V_H V_L$ unit has polyepitopic specificity, antibodies having two or more $V_L$ and $V_H$ domains with each $V_H V_L$ unit binding to a different epitope, antibodies having two or more single variable domains with each single variable domain binding to a different epitope, full length antibodies, antibody fragments such as Fab, FV, dsFv, scFv, diabodies, bispecific diabodies, triabodies, tri-functional antibodies, antibody fragments that have been linked covalently or non-covalently. In some embodiment that antibody has polyepitopic specificity; for example, the ability to specifically bind to two or more different epitopes on the same or different target(s). In some embodiments, the antibodies are monospecific; for example, an antibody that binds only one epitope. According to one embodiment the multispecific antibody is an IgG antibody that binds to each epitope with an affinity of 5 µM to 0.001 pM, 3 µM to 0.001 pM, 1 µM to 0.001 pM, 0.5 µM to 0.001 pM, or 0.1 µM to 0.001 pM.

(vi) Other Antibody Modifications

It may be desirable to modify the antibody provided herein with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et at., *J. Exp Med.* 176:1191-1195 (1992) and Shopes, B. J., *Immunol.* 148:2918-2922 (1992). Homodimeric antibodies with enhanced anti-tumor activity may also be prepared using heterobifunctional cross-linkers as described in Wolff et al., *Cancer Research* 53:2560-2565 (1993). Alternatively, an antibody can be engineered which has dual Fc regions and may thereby have enhanced complement mediated lysis and ADCC capabilities. See Stevenson et al., *Anti-Cancer Drug Design* 3:219-230 (1989).

For increasing serum half the serum half life of the antibody, amino acid alterations can be made in the antibody as described in US 2006/0067930, which is hereby incorporated by reference in its entirety.

(B) Polypeptide Variants and Modifications

Amino acid sequence modification(s) of the polypeptides, including antibodies, described herein may be used in the methods of purifying polypeptides (e.g., antibodies) described herein.

(i) Variant Polypeptides

"Polypeptide variant" means a polypeptide, preferably an active polypeptide, as defined herein having at least about 80% amino acid sequence identity with a full-length native sequence of the polypeptide, a polypeptide sequence lacking the signal peptide, an extracellular domain of a polypeptide, with or without the signal peptide. Such poly peptide variants include, for instance, polypeptides wherein one or more amino acid residues are added, or deleted, at the N or C-terminus of the full-length native amino acid sequence. Ordinarily, a TAT polypeptide variant will have at least about 80% amino acid sequence identity, alternatively at least about any of 85%, 90%, 95%, 96%, 97%, 98%, or 99% amino acid sequence identity, to a full-length native sequence polypeptide sequence, a polypeptide sequence lacking the signal peptide, an extracellular domain of a polypeptide, with or without the signal peptide. Optionally, variant polypeptides will have no more than one conservative amino acid substitution as compared to the native polypeptide sequence, alternatively no more than about any of 2, 3, 4, 5, 6, 7, 8, 9, or 10 conservative amino acid substitution as compared to the native polypeptide sequence.

The variant polypeptide may be truncated at the N-terminus or C-terminus, or may lack internal residues, for example, when compared with a full length native polypeptide. Certain variant polypeptides may lack amino acid residues that are not essential for a desired biological activity. These variant polypeptides with truncations, deletions, and insertions may be prepared by any of a number of conventional techniques. Desired variant polypeptides may be chemically synthesized. Another suitable technique involves isolating and amplifying a nucleic acid fragment encoding a desired variant polypeptide, by polymerase chain reaction (PCR). Oligonucleotides that define the desired termini of the nucleic acid fragment are employed at the 5' and 3' primers in the PCR. Preferably, variant polypeptides share at least one biological and/or immunological activity with the native polypeptide disclosed herein.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme or a polypeptide which increases the serum half-life of the antibody, For example, it may be desirable to improve the binding affinity and/or other biological properties of the polypeptide. Amino acid sequence variants of the polypeptide are prepared by introducing appropriate nucleotide changes into the antibody nucleic acid, or by peptide synthesis. Such modifications include, for example, deletions from, and/or insertions into and/or substitutions of, residues within the amino acid sequences of the polypeptide. Any combination of deletion, insertion, and substitution is made to arrive at the final construct, provided that the final construct possesses the desired characteristics. The amino acid changes also may alter post-translational processes of the polypeptide (e.g., antibody), such as changing the number or position of glycosylation sites.

Guidance in determining which amino acid residue may be inserted, substituted or deleted without adversely affecting the desired activity may be found by comparing the sequence of the polypeptide with that of homologous known polypeptide molecules and minimizing the number of amino acid sequence changes made in regions of high homology.

A useful method for identification of certain residues or regions of the polypeptide (e.g., antibody) that are preferred locations for mutagenesis is called "alanine scanning mutagenesis" as described by Cunningham and Wells, *Science* 244:1081-1085 (1989). Here, a residue or group of target residues are identified (e.g., charged residues such as Arg, Asp, His, Lys, and Glu) and replaced by a neutral or negatively charged amino acid (most preferably Alanine or Polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in the Table 2 below under the heading of "exemplary substitutions." If such substitutions result in a change in biological activity, then more substantial changes, denominated "substitutions" in the Table 2, or as further described below in reference to amino acid classes, may be introduced and the products screened.

TABLE 2

| Original Residue | Substitutions | Exemplary Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |

TABLE 2-continued

| Original Residue | Substitutions | Exemplary Substitutions |
| --- | --- | --- |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains A. L. Lehninger, *Biochemistry* second ed., pp. 73-75, Worth Publishers, New York (1975)):

(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (Q)
(3) acidic: Asp (D), Glu (E)
(4) basic: Lys (K), Arg (R), His(H)

Alternatively, naturally occurring residues may be divided into groups based on common side-chain properties:

(1) hydrophobic: Norleucine, Met, Ala, Val, Leu, Ile
(2) neutral hydrophilic: Cys, Ser, Thr, Asn, Gln,
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the polypeptide to improve its stability (particularly where the antibody is an antibody fragment such as an Fv fragment).

A particularly preferred type of substitutional variant involves substituting one or more hypervariable region residues of a parent antibody (e.g., a humanized antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e,g, binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and target. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the polypeptide alters the original glycosylation pattern of the antibody. The polypeptide may comprise non-amino acid moieties. For example, the polypeptide may be glycosylated. Such glycosylation may occur naturally during expression of the polypeptide in the host cell or host organism, or may be a deliberate modification arising from human intervention. By altering is meant deleting one or more carbohydrate moieties found in the polypeptide, and/or adding one or more glycosylation sites that are not present in the polypeptide.

Glycosylation of polypeptide is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the polypeptide is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Removal of carbohydrate moieties present on the polypeptide may be accomplished chemically or enzymatically or by mutational substitution of codons encoding for amino acid residues that serve as targets for glycosylation. Enzymatic cleavage of carbohydrate moieties on polypeptides can be achieved by the use of a variety of endo- and exo-glycosidases.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains, acetylation of the N-terminal amine, and amidation of any C-terminal carboxyl group.

(11) Chimeric Polypeptides

The polypeptide described herein may be modified in a way to form chimeric molecules comprising the polypeptide fused to another, heterologous polypeptide or amino acid sequence. In some embodiments, a chimeric molecule comprises a fusion of the polypeptide with a tag polypeptide which provides an epitope to which an anti-tag antibody can selectively bind. The epitope tag is generally placed at the amino- or carboxyl-terminus of the polypeptide. The presence of such epitope-tagged forms of the polypeptide can be detected using an antibody against the tag polypeptide. Also, provision of the epitope tag enables the polypeptide to be readily purified by affinity purification using an anti-tag antibody or another type of affinity matrix that binds to the epitope tag.

In an alternative embodiment, the chimeric molecule may comprise a fusion of the polypeptide with an immunoglobulin or a particular region of an immunoglobulin. A bivalent form of the chimeric molecule is referred to as an "immunoadhesin."

As used herein, the term "immunoadhesin" designates antibody-like molecules which combine the binding specificity of a heterologous polypeptide with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

The Ig fusions preferably include the substitution of a soluble (transmembrane domain deleted or inactivated) form of a polypeptide in place of at least one variable region within an Ig molecule. In a particularly preferred embodiment, the immunoglobulin fusion includes the hinge, $CH_2$ and $CH_3$, or the hinge, $CH_1$, $CH_2$ and $CH_3$ regions of an IgG1 molecule.

(iii) Polypeptide Conjugates

The polypeptide for use in polypeptide formulations may be conjugated to a cytotoxic agent such as a chemotherapeutic agent, a growth inhibitory agent, a toxin (e.g., an enzymatically active toxin of bacterial, fungal, plant, or animal origin, or fragments thereof), or a radioactive isotope (i.e., a radioconjugate).

Chemotherapeutic agents useful in the generation of such conjugates can be used. In addition, enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, Phytolaca americana proteins (PAPI, PAPII, and PAP-S), Momordica charantia inhibitor, curcin, crotin, Sapaonaria officinalis inhibitor, gelonin, mitogellin, restrictocin, phenomycin, enomycin, and the tricothecenes. A variety of radionuclides are available for the production of radioconjugated polypeptides. Examples include $^{212}Bi$, $^{131}I$, $^{131}In$, $^{90}Y$, and $^{186}Re$. Conjugates of the polypeptide and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vittea et al., *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the polypeptide.

Conjugates of a polypeptide and one or more small molecule toxins, such as a calicheamicin, maytansinoids, a trichothene, and CC1065, and the derivatives of these toxins that have toxin activity, are also contemplated herein.

Maytansinoids are mitototic inhibitors which act by inhibiting tubulin polymerization. Maytansine was first isolated from the east African shrub *Maytenus serrata*. Subsequently, it was discovered that certain microbes also produce maytansinoids, such as maytansinol and C-3 maytansinol esters. Synthetic maytansinol and derivatives and analogues thereof are also contemplated. There are many linking groups known in the art for making polypeptide-maytansinoid conjugates, including, for example, those disclosed in U.S. Pat. No. 5,208,020. The linking groups include disufide groups, thioether groups, acid labile groups, photolabile groups, peptidase labile groups, or esterase labile groups, as disclosed in the above-identified patents, disulfide and thioether groups being preferred.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hyrdoxymethyl, the C-15 position modified with a hydroxyl group, and the C-20 position having a hydroxyl group. In a preferred embodiment, the linkage is formed at the C-3 position of maytansinol or a maytansinol analogue.

Another conjugate of interest comprises a polypeptide conjugated to one or more calicheamicin molecules. The calicheamicin family of antibiotics is capable of producing double-stranded DNA breaks at sub-picomolar concentrations. For the preparation of conjugates of the calicheamicin family, see, e.g., U.S. Pat. No. 5,712,374. Structural analogues of calicheamicin which may be used include, but are not limited to, $\gamma_1^1$, $\alpha_2^1$, $\alpha_3^1$, N-acetyl-$\gamma_1^1$, PSAG and $\theta_1^1$. Another anti-tumor drug that the antibody can be conjugated is QFA which is an antifolate. Both calicheamicin and QFA have intracellular sites of action and do not readily cross the plasma membrane. Therefore, cellular uptake of these agents through polypeptide (e.g., antibody) mediated internalization greatly enhances their cytotoxic effects.

Other antitumor agents that can be conjugated to the polypeptides described herein include BCNU, streptozoicin, vincristine and 5-fluorouracil, the family of agents known collectively LL-E33288 complex, as well as esperamicins.

In some embodiments, the polypeptide may be a conjugate between a polypeptide and a compound with nucleolytic activity (e.g., a ribonuclease or a DNA endonuclease such as a deoxyribonuclease; DNase)

In yet another embodiment, the polypeptide (e.g., antibody) may be conjugated to a "receptor" (such streptavidin) for utilization in tumor pre-targeting wherein the polypeptide receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

In some embodiments, the polypeptide may be conjugated to a prodrug-activating enzyme which converts a prodrug (e.g., a peptidyl chemotherapeutic agent) to an active anti-cancer drug. The enzyme component of the immunoconjugate includes any enzyme capable of acting on a prodrug in such a way so as to convert it into its more active, cytotoxic form.

Enzymes that are useful include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs into free active drugs.

(iv) Other

Another type of covalent modification of the polypeptide comprises linking the polypeptide to one of a variety of nonproteinaceous polymers, e,g., polyethylene glycol, polypropylene glycol, polyoxyalkylenes, or copolymers of polyethylene glycol and polypropylene glycol. The polypeptide also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical *Sciences,* 18th edition, Gennaro, A.R., Ed., (1990).

VII. Obtaining Polypeptides for Use in the Formulations and Methods

The polypeptides used in the methods of analysis described herein may be obtained using methods well-known in the art, including the recombination methods. The following sections provide guidance regarding these methods.

(A) Polynucleotides

"Polynucleotide," or "nucleic acid," as used interchangeably herein, refer to polymers of nucleotides of any length, and include DNA and RNA.

Polynucleotides encoding polypeptides may be obtained from any source including, but not limited to, a cDNA library prepared from tissue believed to possess the polypeptide mRNA and to express it at a detectable level. Accordingly, polynucleotides encoding polypeptide can be conveniently obtained from a cDNA library prepared from human tissue. The polypeptide-encoding gene may also be obtained from a genomic library or by known synthetic procedures (e.g., automated nucleic acid synthesis).

For example, the polynucleotide may encode an entire immunoglobulin molecule chain, such as a light chain or a heavy chain. A complete heavy chain includes not only a heavy chain variable region ($V_H$) but also a heavy chain constant region ($C_H$), which typically will comprise three constant domains: $C_H1$, $C_H2$ and $C_H3$; and a "hinge" region. In some situations, the presence of a constant region is desirable. In some embodiments, the polynucleotide encodes one or more immunoglobulin molecule chains of a TDB.

Other polypeptides which may be encoded by the polynucleotide include antigen-binding antibody fragments such as single domain antibodies ("dAbs"), Fv, scFv, Fab' and F(ab)$_2$ and "minibodies." Minibodies are (typically) bivalent antibody fragments from which the $C_H1$ and $C_K$ or $C_L$ domain has been excised. As minibodies are smaller than conventional antibodies they should achieve better tissue penetration in clinical/diagnostic use, but being bivalent they should retain higher binding affinity than monovalent antibody fragments, such as dAbs. Accordingly, unless the context dictates otherwise, the term "antibody" as used herein encompasses not only whole antibody molecules but also antigen-binding antibody fragments of the type discussed above. Preferably each framework region present in the encoded polypeptide will comprise at least one amino acid substitution relative to the corresponding human acceptor framework. Thus, for example, the framework regions may comprise, in total, three, four, five, six, seven, eight, nine, ten, eleven, twelve, thirteen, fourteen, or fifteen amino acid substitutions relative to the acceptor framework regions.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Further details of the invention are illustrated by the following non-limiting Examples. The disclosures of all references in the specification are expressly incorporated herein by reference.

EXAMPLES

The examples below are intended to be purely exemplary of the invention and should therefore not be considered to limit the invention in any way. The following examples and detailed description are offered by way of illustration and not by way of limitation.

Example 1

T Cell Activation Assay

Figure 2:
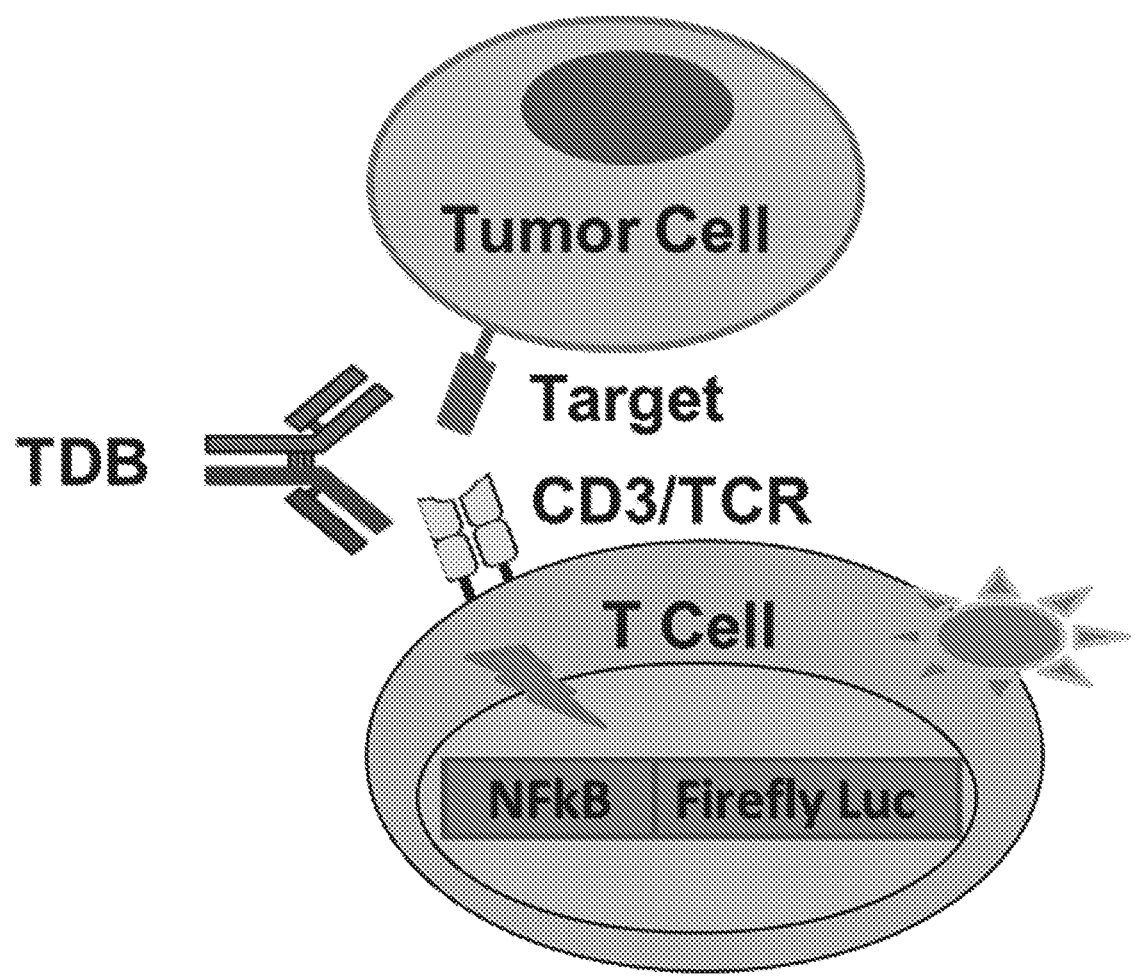
FIG. 2 shows a schematic representation of activation in a reporter T cell mediated by an exemplary TDB. The reporter cell contains the firefly luciferase reporter gene driven by NFκB response elements, which is expressed following T cell activation mediated by bridging of the reporter T cell with a target tumor cell by the TDB.
Figure 3A:
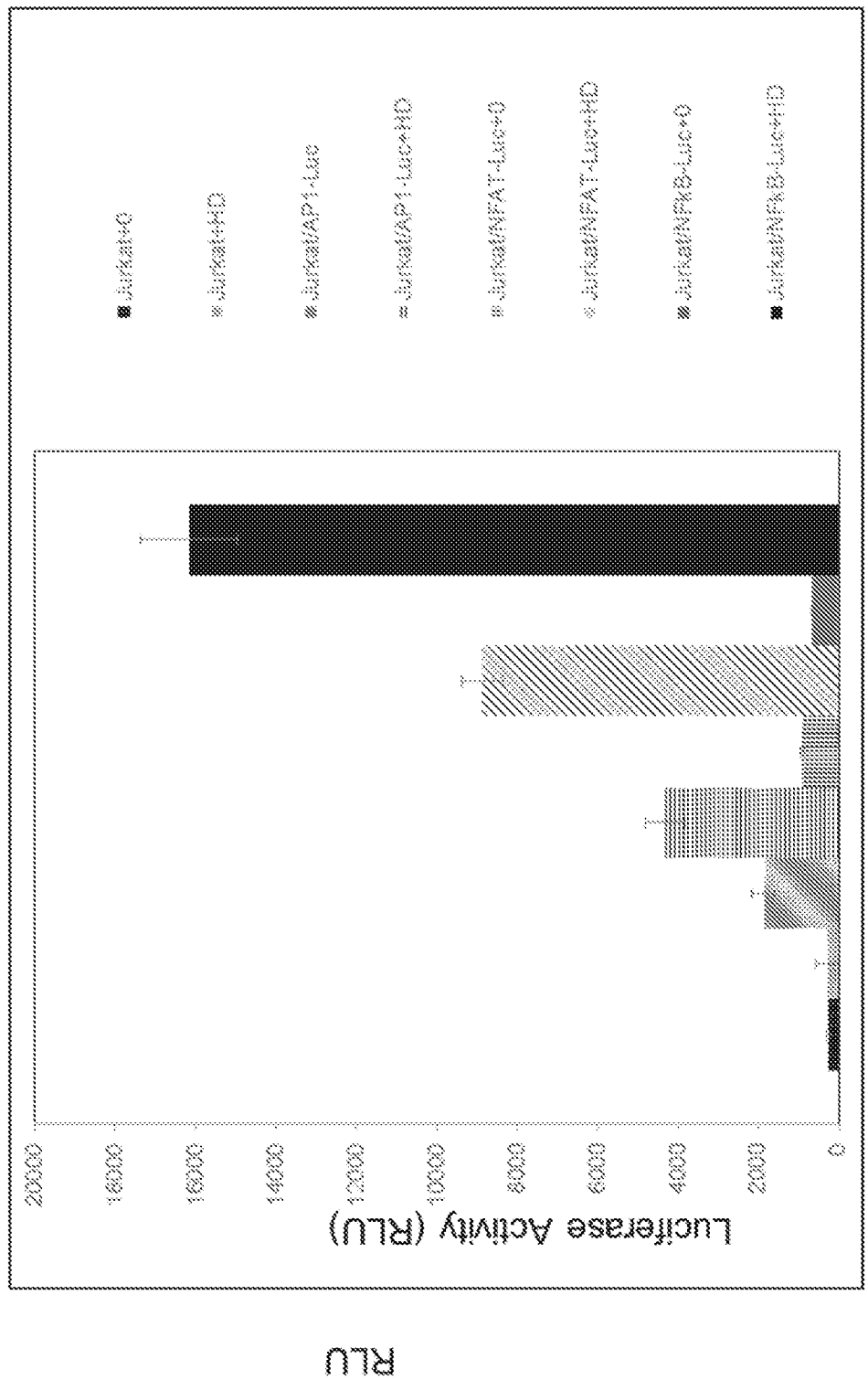
FIG. 3A shows T cell activation by Anti-CD3 homodimer can be monitored using a reporter gene assay. The human Jurkat CD4$^+$ T cell line was genetically engineered to stably express the firefly luciferase reporter gene driven by various T Cell Receptor (TCR) responsive transcriptional response elements (AP-1, NFAT, and NFκB), stable cell pools selected, and pools evaluated for response to treatment with 10 μg/mL of purified Anti-CD3 homodimer for 4 hours. Luminescence responses (luciferase reporter gene activity) were plotted, with the highest response observed from the Jurkat/NFκBluciferase stable pool.
Figure 3B:
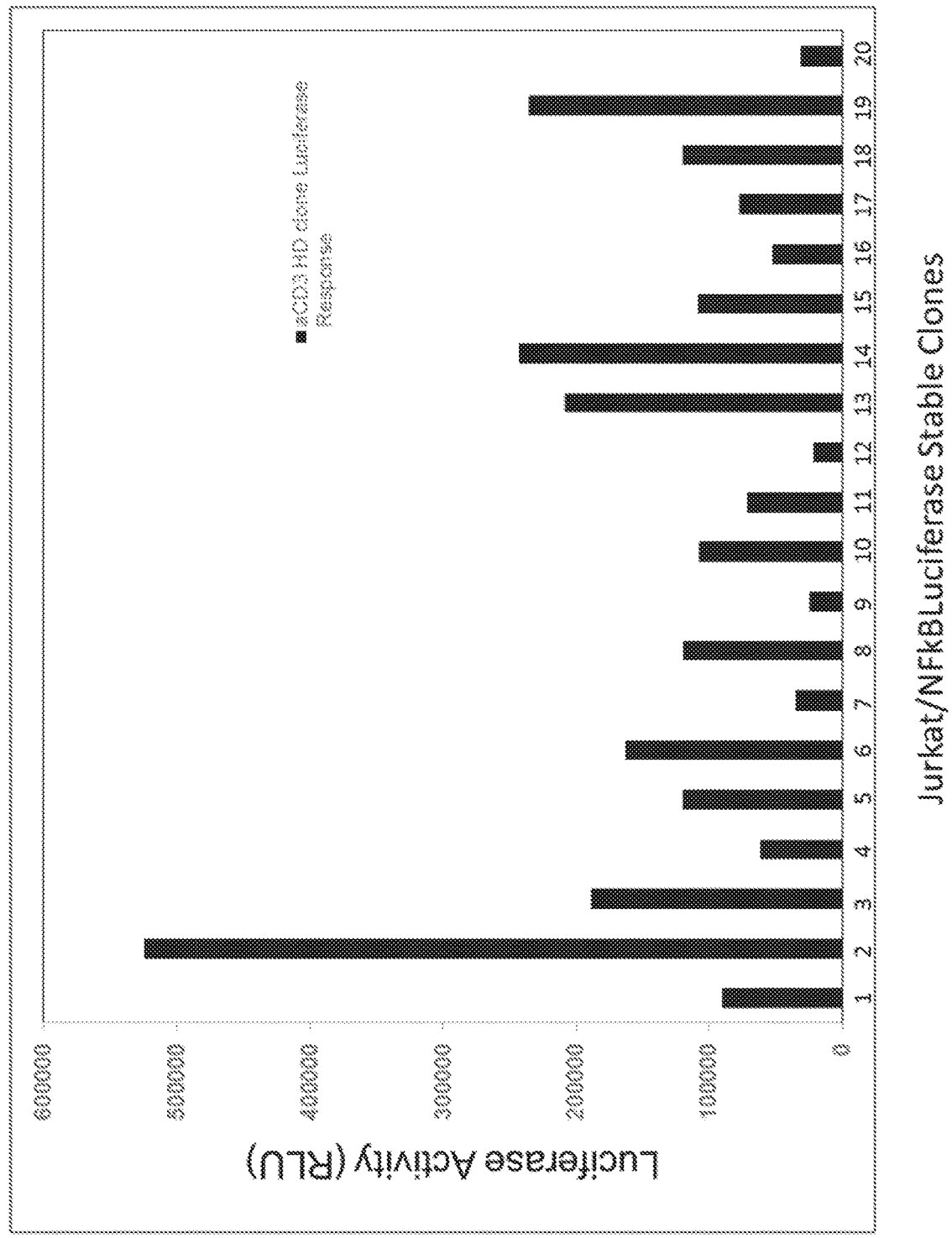
FIG. 3B shows Jurkat/NFκBLuciferase stable clones.

A T cell activation assay has been developed to determine the potency and specificity of a T Cell Dependent Bispecific (TDB) antibody for activating T cells in the presence of target cells. See FIG. 2 for an exemplary schematic representation. As TDBs are bivalent and bispecific, with one arm specific for a TCR complex subunit and the other specific for a target antigen, cross-linking of TCRs leading to T cell activation can only occur when both the target cell and the T cell are bound by the TDB. TCR mediated cross-linking by anti-CD3-containing TDBs activates T cell signal transduction cascades leading to the phosphorylation and nuclear localization of transcription factors, including NFAT and NFκB, resulting in the transcriptional induction of target genes such as cytokines or cell killing agents such as Fas, Granzyme B and Perforins (Brown, W M, 2006, *Curr Opin Investig Drugs* 7:381-388; Ferran, C et al., 1993 *Exp Nephrol* 1:83-89; Shannon, M F et al., 1995, *J. Leukoc. Biol.* 57:767-773; Shapiro, 1998; Pardo, J, et al., 2003, *Int Immunol.*, 15(12):1441-1450). Reporter genes, such as firefly luciferase, under the transcriptional control of AP1, MAT, or NFκB, have been used to monitor TCR activation of signaling pathways and T cell activation (Shannon, M F et al., 1995, *J. Leukoc. Biol.* 57:767-773; Shapiro, 1998). To evaluate if TDBs can activate T cells in vitro, Jurkat T cells (DSMZ, ACC 282) were infected with recombinant TCR-responsive reporter gene lentiviral stocks (AP1-Luciferase, NFAT-Luciferase, or NFκB-Luciferase) and stable pools of reporter T cells were isolated. To initially assess the suitability of the reporter T cells for assaying activation, they were treated with purified Anti-CD3 homodimer, which can cross-link TCR receptors in the absence of target cells, at 10 µg/mL for 4 hours. Jurkat/AP1Luciferase, Jurkat/NFATLuciferase, and Jurkat/NFκBLuciferase stable pools showed a dose-dependent induction of luciferase upon stimulation with purified Anti-CD3 homodimer. Luminescence responses (luciferase reporter gene activity) were plotted, with the highest response observed from the Jurkat/NFκBluciferase stable pool (FIG. 3A). Jurkat/NFκBLuciferase stable clones isolated by limiting dilution were screened for their response to 10 µg/mL of purified Anti-CD3 homodimer. Jurkat T cell NFκBLuciferase pools demonstrated the highest response to Anti-CD3 homodimer compared to other TCR-response elements, and were selected for further investigation (FIG. 39).

Figure 4A:
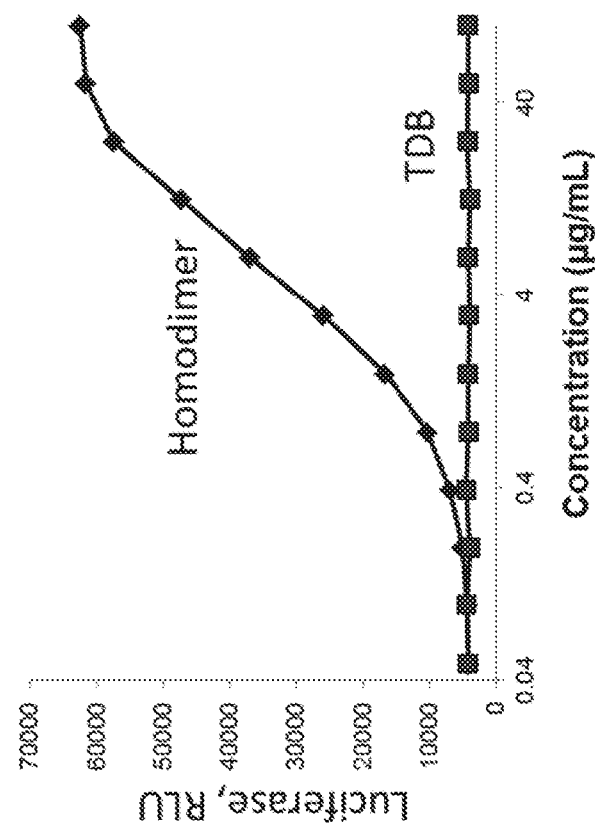
FIGS. 4A and 4B show that purified anti-CD3 homodimer can activate T cells in the presence of or absence of target cells.
Figure 4B:
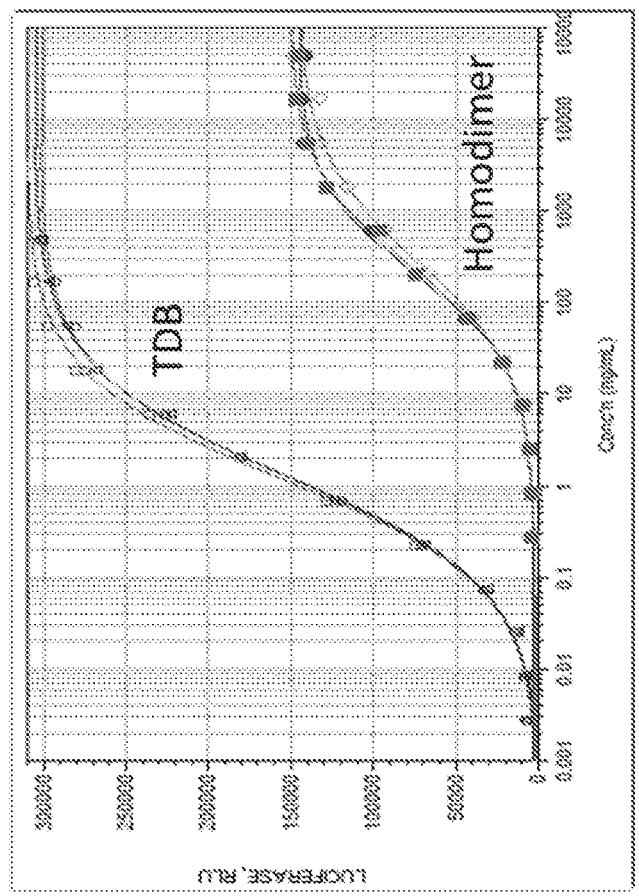

To determine the relative response of this clone to either αCD20/αCD3 TDB or to anti-CD3 homodimer, the Jurkat/NFκBLuciferase clone 2 cell line was treated with increasing concentrations of either αCD20/αCD3 TDB or anti-CD3 homodimer in the presence of a CD20 expressing target cell line, and luciferase activity was plotted (FIG. 4A). The cells were stimulated with αCD20/αCD3 TDB or a CD3 homodimer for 4 hours in RPMI 1640 medium supplemented with 10% Fetal Bovine Serum. Purified αCD20/αCD3 TDB was 1000-fold more active than purified anti-CD3 homodimer in the presence of co-stimulatory target cells. In the absence of target cells, αCD20/αCD3 TDB did not result in T cell activation at even high levels of the TDB, as measured by NFκB-dependent activation of luciferase transcription in this cell line, indicating the specificity of the assay for detecting simultaneous binding of the TDB to target and effector cells (FIG. 49). The T cell activation responses observed for the engineered Jurkat/NFκBLuciferase clone 2 reporter gene cell line is comparable to that observed using human T cells isolated from donor Peripheral Blood Mononuclear Cells (PBMCs) using other measures of T cell activation, indicating that the use of a reporter gene to monitor T cell activation response is comparable (Table 3). The Jurkat/NFκBluciferase clone 2 cell line (Jurkat-NFκBLuc), was used to develop and optimize a cell-based assay method for the detection of TDB-mediated T cell activation.

TABLE 3

| | Anti-CD3 homodimer ($EC_{50}$) in absence of target cells | αCD20/αCD3 TDB ($EC_{50}$) in presence of target cells |
|---|---|---|
| Human PBMC (CD69$^+$/CD25$^+$) Donor 1 | 526 ng/mL | 5.5 ng/mL |
| Human PBMC (CD69$^+$/CD25$^+$) Donor 2 | 169 ng/mL | 4.4 ng/mL |
| Jurkat/NFκBLuc | 210 ng/mL | 1.3 ng/mL |

Example 2

Quantitative Method to Detect TDB-Mediated T Cell Activation

A sensitive and quantitative platform TDB cell-based assay to determine the potency of anti-CD3 containing TDBs by measuring the induction of T cell activation in the presence of target cells has been developed. The TDB T cell activation assay detects activation of T cells by a TDB in the presence of target cells by measuring TCR cross-linking-induced activation of the Rel/NFκB signaling pathway using an engineered T cell reporter gene cell line, Jurkat-NFκBLuc. Activated NFκB translocates to the nucleus, binds to the 8 NFκB response elements in the synthetic promoter and drives the transcription of luciferase.

Figure 5:
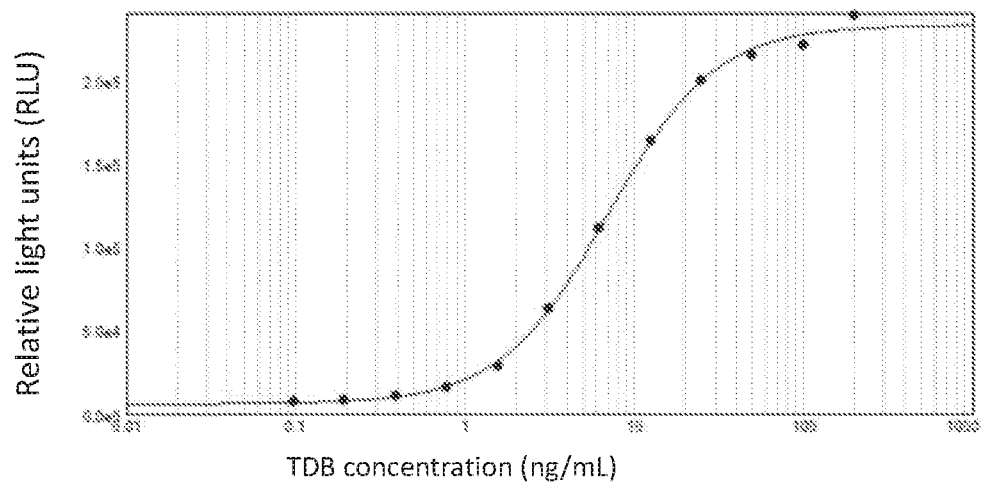
FIG. 5 shows T cell activation by αCD20/CD3, αHER2/CD3, and αCD79b/CD3 TDBs in the presence of appropriate target cells (Wil2-S, BT-474, and BJAB cells, respectively) can be monitored using a reporter gene assay with Jurkat/NFκB-fireflyLuciferase cells. Luminescence responses (Luciferase reporter gene activity) were plotted as a function of TDB concentration.
Figure 5:
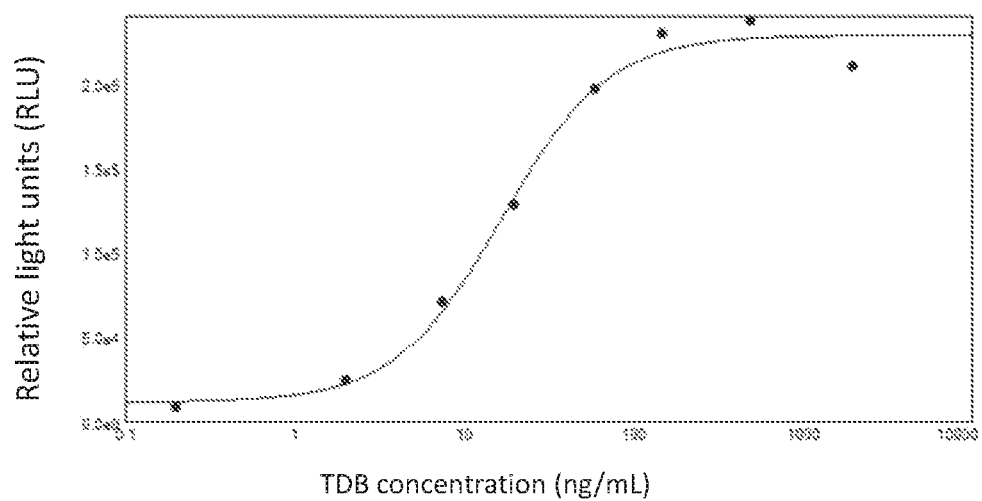
Figure 5:
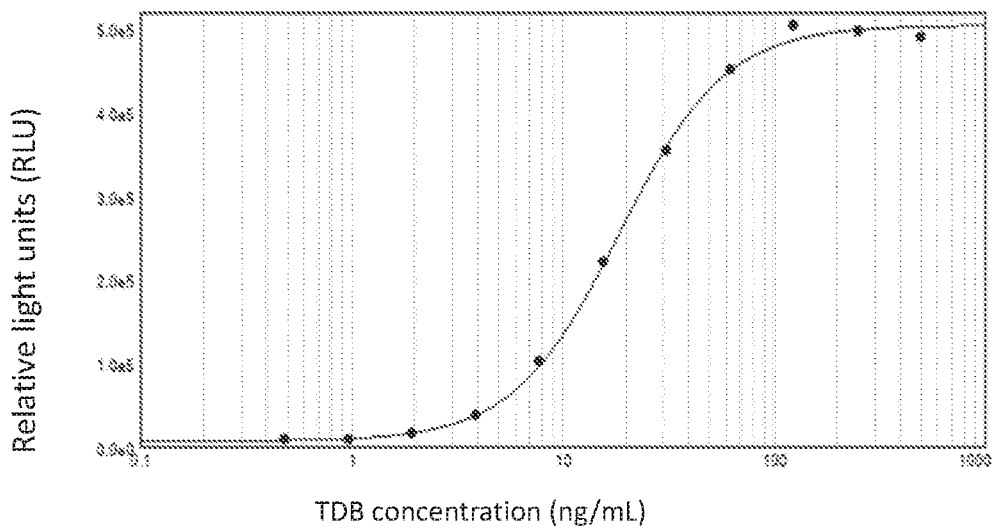

In the assay, dilutions of Anti-CD20/CD3 (or Anti-HER2/CD3 or Anti-CD79b/CD3) assay standard, control, and test samples were prepared and 50 μL was added to 96 well assay plates. Target cells (Wil2-S, BT-474 or SKBR3, and BJAB cells for αCD20/CD3, αHER2/CD3, and αCD79b/CD3, respectively) and JurkatNFkB reporter cells were then prepared, using either ready-to-use (R-to-U) frozen cells or cultured cells following assessment that frozen cells are comparable to fresh cultured cells. Equal volumes of 4.0×$10^5$ cells/mL of target cell diluent and 1.6×$10^6$ cells/mL JurkatNFkB cell diluent were combined to prepare a cell mixture with a target:effector (T:E) cell ratio of 1:4. 50 μL of the mixed target and JurkatNFkBLuc cells was added to the each TDB dilution in the assay plate. The same T:E ratio was used for αHER2/CD3 and αCD79b/CD3 cell based assays as well for the assays including the reference and control TDBs. Following target cell conjugation to the JurkatNFkBLuc T cell reporter cell line by the TDB, activated NFκB translocates to the nucleus, binds to the 8 NFκB response elements in the synthetic promoter and drives the transcription of luciferase. After 4-5 hours of assay incubation, the amount of luciferase activity induced by each sample was measured using a luminescence plate reader (FIG. 5). The relative potency of the control and the test samples was determined from a standard curve of luminescence generated from the TDB reference standard using 4P analysis as follows:

Use a 4-parameter logistic curve-fitting program to generate separate curves for standard, control and sample(s).

The equation is:

$y = ((A-D)/(1+(x/C)^B))+D$

Where: x=the independent variable
A=Zero Dose Response (Lower asymptote=LA)
B=Slope
C=EC50, ng/mL
D=Maximum Dose Response (Upper asymptote=UA)

Determine the fold response for the standard curve (ST) and each test article (TA) (control or sample(s)) curve as follows:
Amplitude of response=UA/LA
Report the value.
Check for similarity between the ST and each TA curve as follows:
Test for parallelism. Determine the Slope Ratio using the following equation:

$$\frac{|(D_{TA} - A_{TA}) \times B_{TA}|}{|(D_{ST} - A_{ST}) \times B_{ST}|}$$

Determine the Lower asymptote percent difference (LAD) using the following equation:

$$\left| \frac{LA_{TA} - LA_{ST}}{UA_{ST} - LA_{ST}} \times 100 \right|$$

Determine the Upper asymptote percent difference (UAD) using the following equation:

$$\left| \frac{UA_{TA} - UA_{ST}}{UA_{ST} - LA_{ST}} \times 100 \right|$$

Calculate the potency of the test article using a constrained 4-P parallel curve.
For the ST and TA generate constrained curves using the following equations:

$$y_{ST} = D + \frac{A - D}{1 + \left(\frac{x}{C_{ST}}\right)^B}$$

$$y_{TA} = D + \frac{A - D}{1 + \left(\frac{\rho x}{C_{ST}}\right)^B}$$

Where: x=the independent variable
A=Common lower asymptote
B=Common slope
CST=Standard EC50 value
D=Common upper asymptote
ρ=relative potency of test article (the relative potency is the ratio of EC50 of ST over EC50 of TA)

Figure 6A:
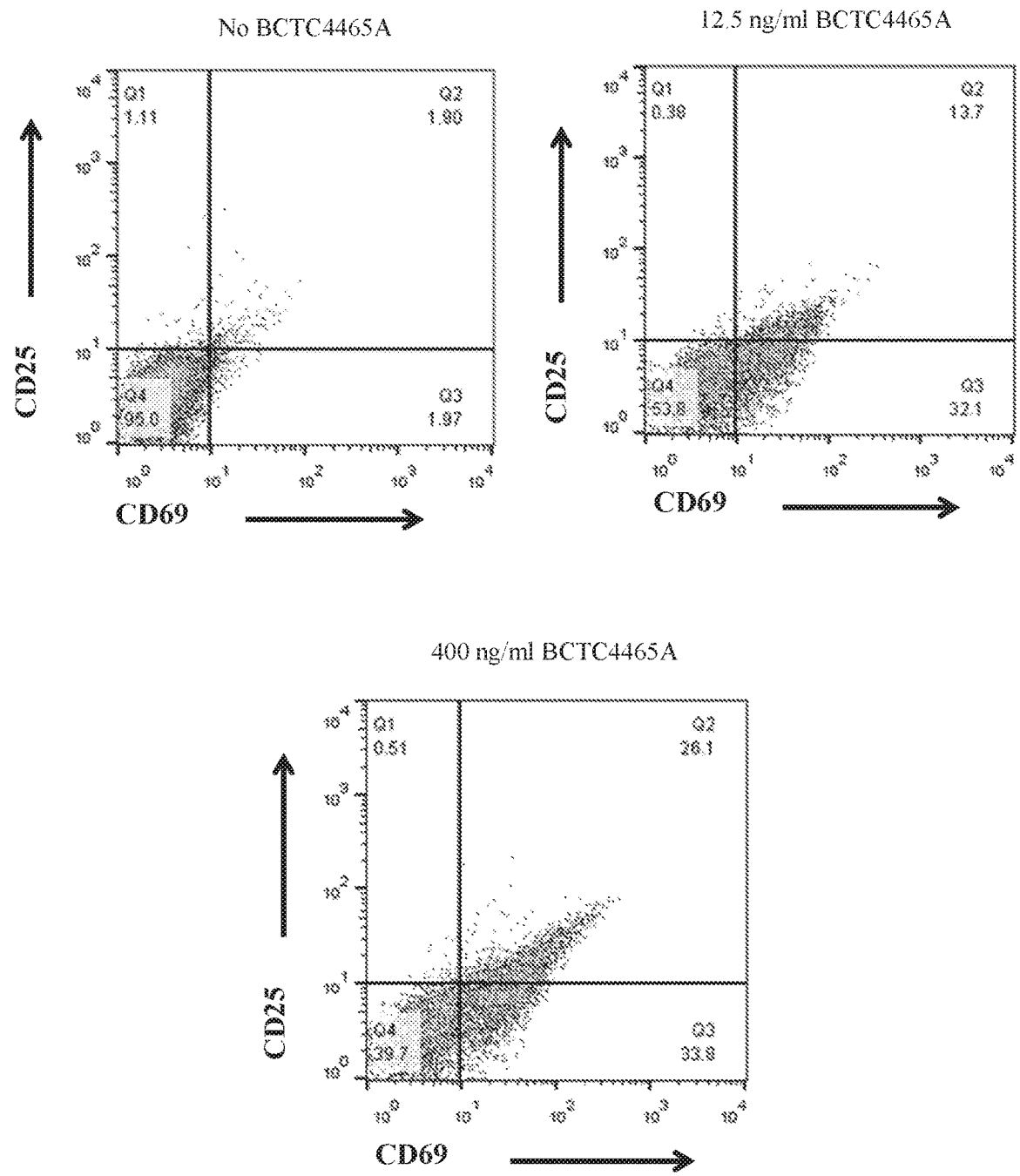
FIGS. 6A and 6B show that markers of T cell activation CD69 and CD25 increased in a dose-dependent manner in response to incubation with an αCD20/αCD3 TDB.
Figure 6B:
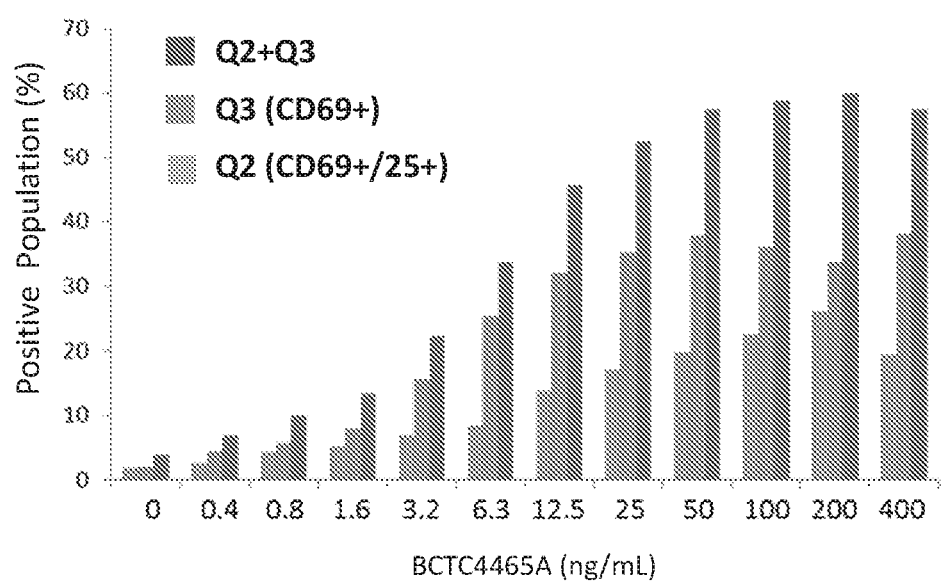
Figure 7:
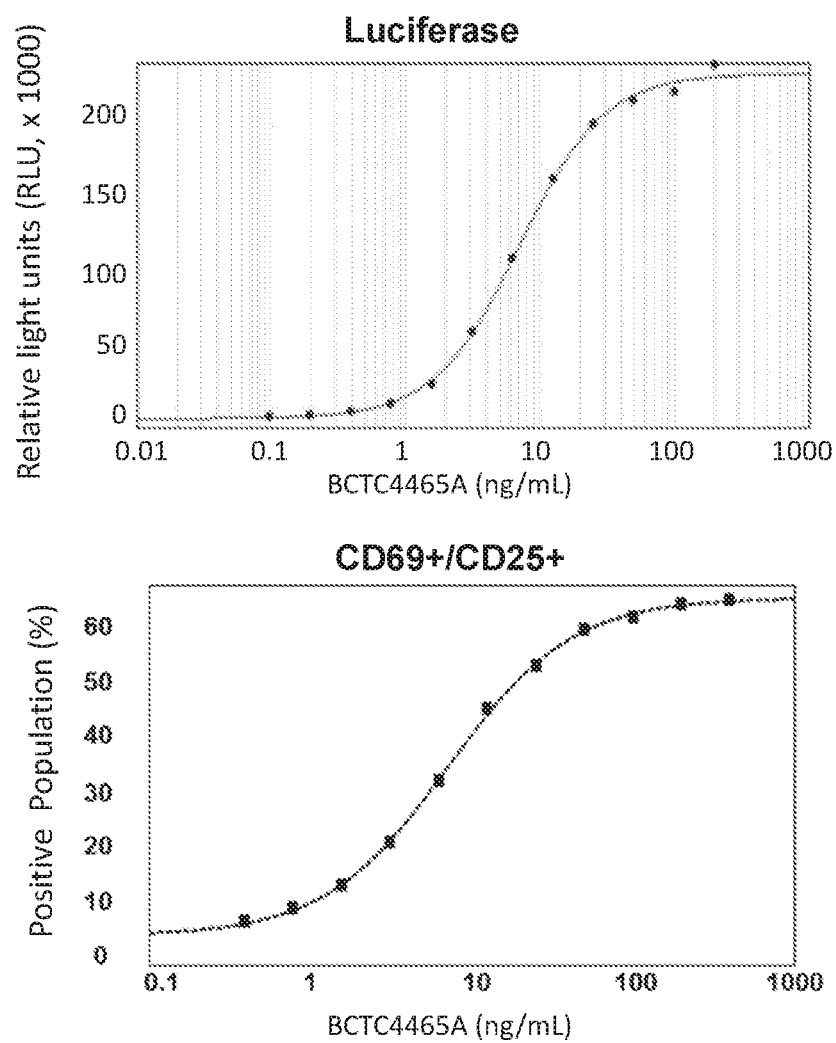
FIG. 7 shows a comparison of the dose-response curves for T cell activation by the αCD20/αCD3 TDB BCTC4465A, measured using either the Jurkat/NFκB-fireflyLuciferase-based reporter assay or flow cytometry for positive surface expression of CD69 and CD25.

Calculate the potency, expressed as % Relative Potency, for the control and sample(s):
Potency=ρ×Activity of Reference Material CD69 (C-type lectin protein) and CD25 (IL-2 receptor) are markers of T cell activation (Shipkova M, 2012, *Clin. Chim. Acta.* 413:1338-49 and Ziegler S F, et al., 1994, *Stem Cells* 12(5): 465-465), and their induction on the surface of T cells 24 hours following addition of the αCD20/CD3 TDB was evaluated by flow cytometry. CD69 and CD25 cell surface expression increased in a dose-dependent manner in response to incubation with the αCD20/αCD3 TDB (FIGS. 6A and 6B), and the dose-response curve correlated well with that obtained by measuring the luciferase signal from the JurkatNFkBLuc T cell reporter cell line (FIG. 7), demonstrating that the luciferase measurement is a relevant readout of T cell activation in the TDB cell-based assay using JurkatNFkBLuc cells.

Figure 8:
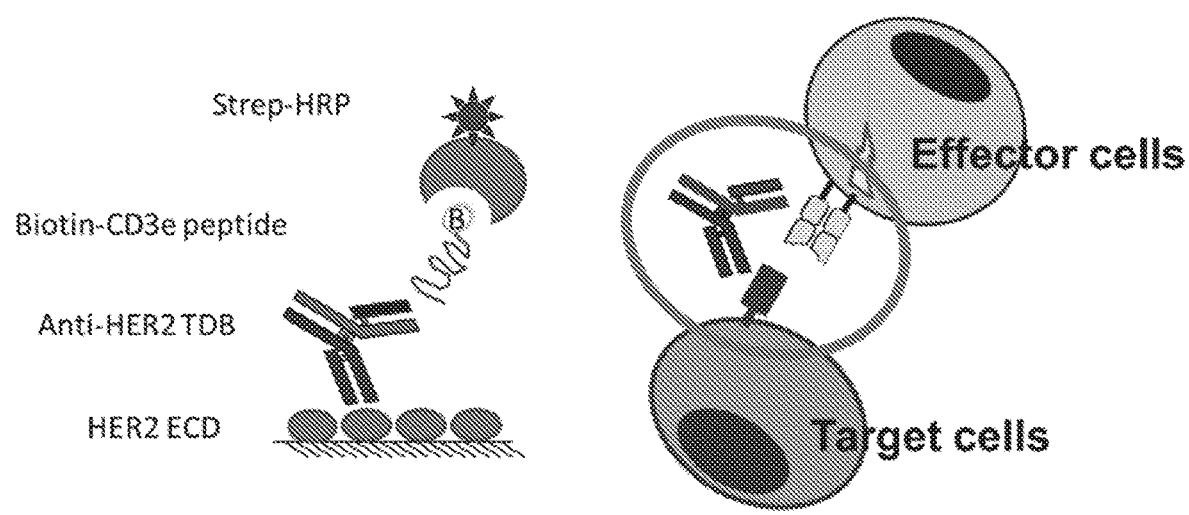
FIG. 8 shows a schematic representation of an exemplary TDB in an ELISA-based bridging binding assay, with a first arm of the TDB specific for a HER2 epitope and a second arm of the TDB specific for a CD3ε epitope. An extracellular fragment of the HER2 protein containing the HER2 epitope is coated on the surface of a plate and bridged with a biotin-labeled CD3ε peptide containing the CD3ε epitope by the anti-HER2/CD3ε TDB, and binding is detected by streptavidin-conjugated HRP.
Figure 9:
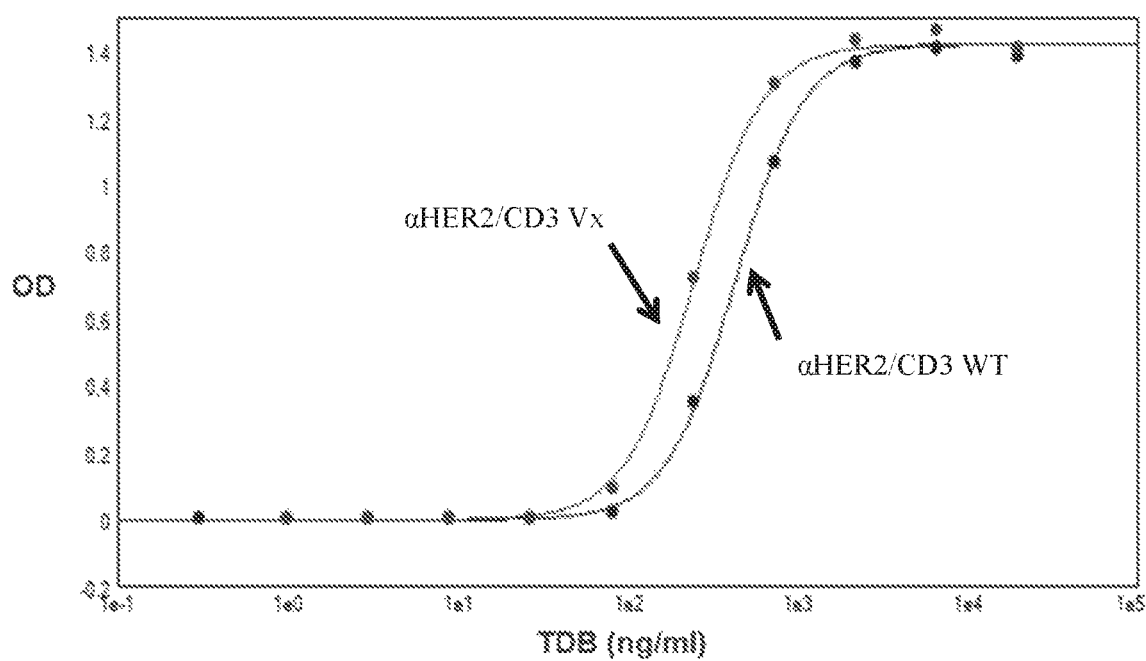
FIG. 9 shows that potency for T cell activation varies between two αHER2/CD3 TDBs (αHER2/CD3 Vx and αHER2/CD3 WT) with different CD3-binding affinities in the presence of BT-474 target cells, monitored using the Jurkat/NFκB-fireflyLuciferase cell-based reporter assay. Luminescence responses (luciferase reporter gene activity) were plotted as a function of TDB concentration.
Figure 10A:
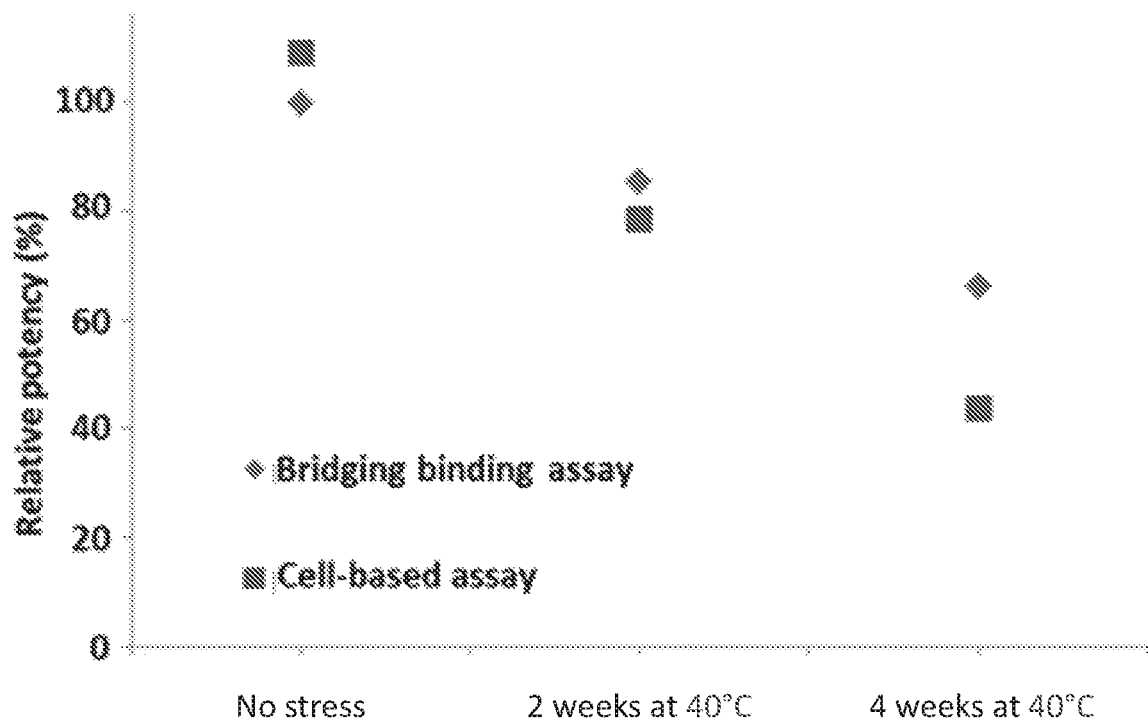
FIGS. 10A and 10B show that potency for T cell activation varies between αHER2/CD3 TDB samples subjected to different thermal stress conditions, including no stress, 2 weeks at 40° C., and 4 weeks at 40° C., monitored using the Jurkat/NFκB-fireflyLuciferase cell-based reporter assay and the ELISA-based bridging binding assay.
Figure 10B:
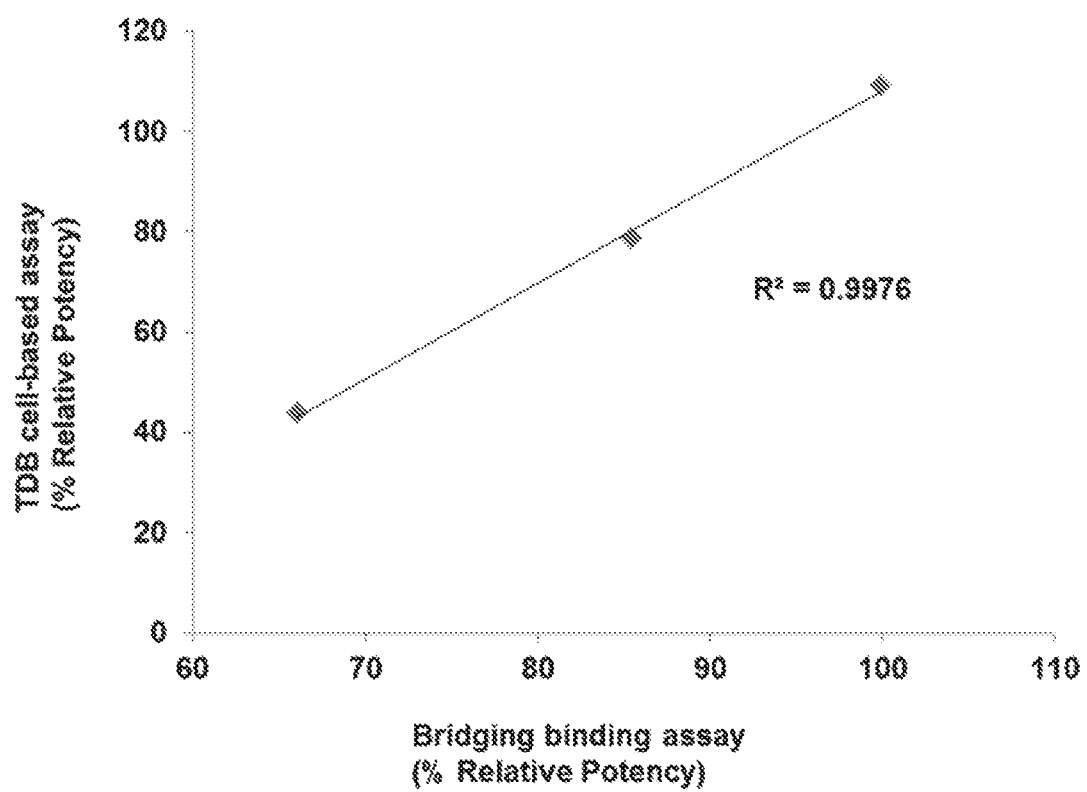

The amount of simultaneous binding of the TDB with its targets was assessed using an ELISA-based bridging binding assay. See FIG. 8 for an exemplary schematic representation. The bridging of a TCR complex subunit and the extracellular domain (ECD) of the target antigen by a TDB is an essential interaction representing the mechanism of action of the TDB. The assay was used to detect the different affinities of anti-HER2/CD3 TDB variants (FIG. 9), and anti-HER2/CD3 samples subjected to thermal stress conditions (2 wks and 4 wks at 40° C., see FIG. 10A). In the TDB bridging binding assay for anti-HER2/CD3, HER2 ECD (CR #156) was used as coating material on the plate. After 16-72 hours, the plate was washed and then αHER2/CD3 TDB was incubated for 1-2 hour in assay diluent. After washing, biotinylated CD3ε peptide was incubated for 1-2 hours, followed by Strep-HRP incubation. After a final wash, the amount of HRP conjugated to the plate was measured using a detection agent. A strong correlation ($R^2$=0.9976) between the bridging binding assay and the TDB cell-based assay was observed (FIG. 10B), further supporting the use of the TDB cell-based assay as a measure of TDB potency.

Bridging Assay

Materials

Coat material: HER2 ECD (CR #156)

Coating buffer: Dulbecco's Phosphate Buffered Saline without $CaCl_2$ and $MgCl_2$, Gibco Cat. No. 14190

Assay Diluent/Detection Dilution Buffer: PBS+0.5% BSA+0.05% PS20

Wash buffer:PBS+0.05% PS20

Detection: Strep-HRP

Coat plates

1. Dilute coat reagent to 4 μg/mL in coating butler
2. Coat all 96 wells with 100 μL.
3. Seal with plate sealer.
4. Incubate at 2-8° C. 16-72 hours.

Assay Procedure

1. Wash the plates 6 times with wash buffer using the wash program "Auto" (i.e., Run two cycles of Auto program).
2. Block the plates using 200 μL of AD per well. Seal and incubate 1-2 hours at 25° C. with shaking.
3. Prepare αHER2 TDB Ab in AD.
   4. After blocking, Wash the plate 6 times as step 1
5. Add 100 uL of diluted αHER2 TDB to each well. Incubated 1 hours+10 min at 25° C. with shaking.
6. Repeat Step 1.
7. Prepare CD3e peptide (16 mer) with final concentration: 1 μg/mL of CD3e peptide
8. Add 100 μL to each well. Incubate for 1 hour
9. Repeat Step 1.
   10. Add Strep-HRP, final concentration of 2 ng/mL, and incubate at 25C for 1 hour
11. Repeat Step 1.
12. Add 100 μL Sure Blue Reserve to wells. Develop until optimal color development before stopping reaction with 100 μL 0.6N Sulfuric Acid.
15. Read OD 450/650

Example 3

Analysis of Anti-FcRH5/Anti-CD3 Antibody

Figure 11:
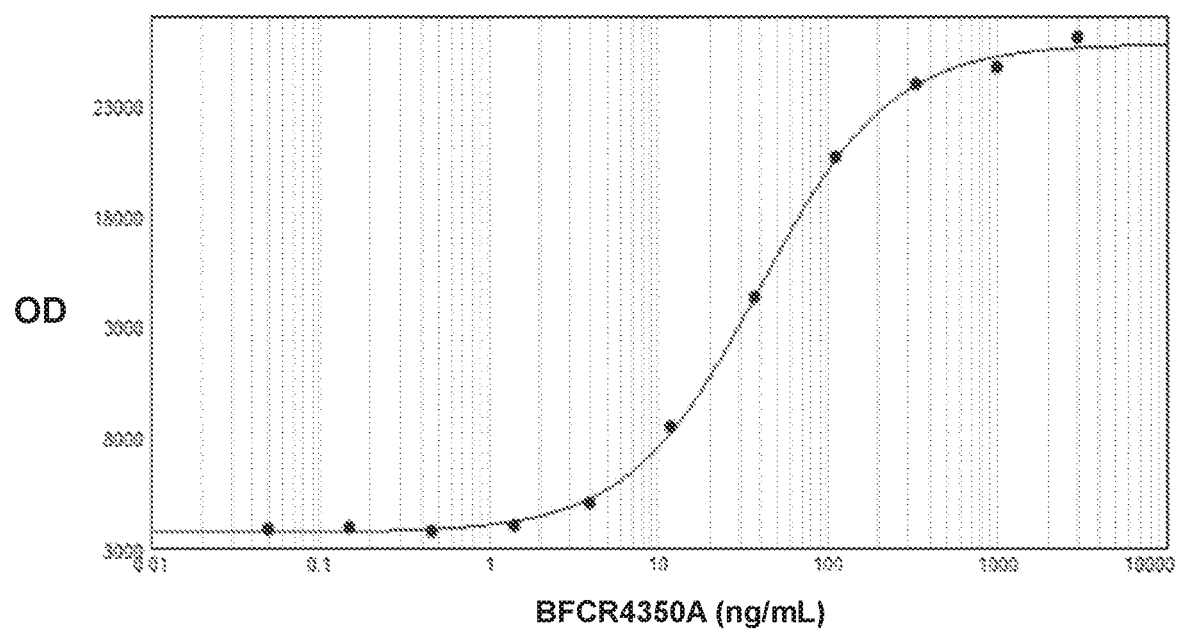
FIG. 11 shows the potency for T cell activation of an αFcRH5/CD3 TDB in the presence of FcRH5-expressing EJM target cells, monitored using the Jurkat/NFκB-firefly-Luciferase cell-based reporter assay. Luminescence responses (luciferase reporter gene activity) were plotted as a function of TDB concentration.

The assays described in Example 2 were used to measure the potency of and anti-FcRH5/anti-CD3 TBD. In the assay, dilutions of anti-FcRH5/CD3 assay standard, control, and test samples were prepared and 50 μL was added to 96 well assay plates. Target cells (FcRH5-expressing EJM cells) and JurkatNFkB reporter cells were then prepared, using either ready-to-use (R-to-U) frozen cells or cultured cells following assessment that frozen cells are comparable to fresh cultured cells. Equal volumes of $4.0×10^5$ cells/mL of target cell diluent and $1.6×10^6$ cells/mL JurkatNFkB cell diluent were combined to prepare a cell Mixture with a target:effector (T:E) cell ratio of 1:4. 50 μL of the mixed target and JurkatNFkBLuc cells was added to the each TDB dilution in the assay plate. The same T:E ratio was used for the reference and control TDBs. After 4-5 hours of assay incubation, the amount of luciferase activity induced by each sample was measured using a luminescence plate reader (FIG. 11). The relative potency of the control and the test samples was determined from a standard curve of luminescence generated from the TDB reference standard using 4P analysis as follows described in Example 2.

Figure 12:
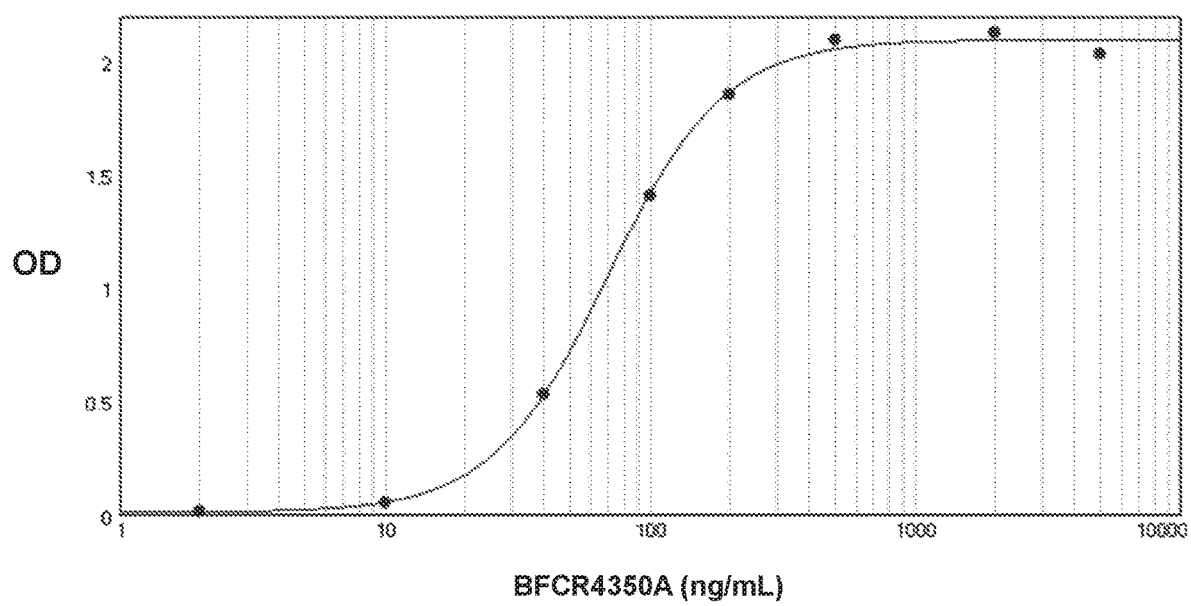
FIG. 12 shows potency for T cell activation of an αFcRH5/CD3 TDB using an ELISA-based bridging assay.

The amount of simultaneous binding of the anti-FcRH5/CD3 TDB with its targets was assessed using an ELISA-based bridging binding assay as described in Example 2. In the TDB bridging binding assay for anti-FcRH5/CD3, domain 9 FcRH5 ECD was used as coating material on the plate. After 16-72 hours, the plate was washed and then αFcRH5/CD3 TDB was incubated for 1-2 hour in assay diluent. After washing, biotinylated CD3ε peptide was incubated for 1-2 hours, followed by Strep-HRP incubation. After a final wash, the amount of HRP conjugated to the plate was measured using a detection agent (FIG. 12).

What is claimed is:

1. A method for detecting a T cell dependent bispecific antibody (TDB) in a composition, wherein the TDB comprises a target antigen binding fragment and a CD3 binding fragment, the method comprising contacting a population of T cells and target cells with the composition, wherein the T cells comprise nucleic acid encoding a reporter operably linked to a response element that is responsive to T cell activation, wherein the response element that is responsive to T cell activation is an NFκB promoter, and wherein the target cells express the target antigen;

wherein expression of the reporter indicates the presence of the TDB.

2. The method of claim 1, wherein the reporter is a luciferase, a fluorescent protein, an alkaline phosphatase, a beta lactamase, or a beta galactosidase.

3. The method of claim 2, wherein the luciferase is a firefly luciferase, a *Renilla* luciferase, or a nanoluciferase.

4. The method of claim 1, wherein the population of T cells is a population of CD4⁺T cells or CD8⁺T cells.

5. The method of claim 1, wherein the population of T cells is a population of Jurkat T cells or CTLL-2 T cells.

6. The method of claim 1, wherein the target antigen is expressed on the surface of the target cell.

7. The method of claim 1, wherein the target antigen is CD4, CD8, CD18, CD19, CD11a, CD11b, CD20, CD22, CD34, CD40, CD79α (CD79a), CD79β (CD79b), EGF receptor, HER2 receptor, HER3 receptor, HER4 receptor, FcRH5, CLL1, LFA-1, Mac1, p150, 95, VLA-4, ICAM-1, VCAM, αv/β3 integrin, VEGF, flk2/flt3 receptor; obesity (OB) receptor; mpl receptor; CTLA-4; protein C, BR3, c-met, tissue factor, β7, Tenb2, STEAP, or transmembrane tumor-associated antigens (TAA).

8. The method of claim 1, wherein
   a) the target antigen is HER2 receptor and the target cell is a BT-474 cell,
   b) the target antigen is HER2 receptor and the target cell is a SKBR3 cell,
   c) the target antigen is CD20 and the target cell is a Wil2-S cell, or
   d) the target antigen is CD79b and the target cell is a BJAB cell.

9. The method of claim 1, wherein the ratio of T cells to target cells in the population of cells is about 1:1, about 1:2, about 1:3, about 1:4, about 1:5, about 1:6, about 1:7, about 1:8, about 1:9 or about 1:10.

10. The method of claim 1, wherein the population of cells ranges from about $1 \times 10^3$ to about $1 \times 10^6$ cells or about $1 \times 10^4$ to about $5 \times 10^4$ cells.

11. The method of claim 1, wherein the population of T cells is contacted with a composition comprising the TDB at a concentration ranging from 0.01 ng/mL to 50 ng/mL.

12. The method of claim 1, wherein the reporter is detected after 1, 2, 3, 4, 5, 6, 7, 8, 12, 16, 20, or 24 hours after contacting the cells with the composition.

13. A method for quantitating the amount of T cell dependent bispecific antibody (TDB) in a composition, wherein the TDB comprises a target antigen binding fragment and a CD3 binding fragment, the method comprising
   contacting a population of T cells and target cells with the composition, wherein the T cells comprise nucleic acid encoding a reporter operably linked to a response element that is responsive to T cell activation, wherein the response element that is responsive to T cell activation is an NFκB promoter, and wherein the target cells express the target antigen;
   correlating the expression of the reporter as a function of antibody concentration with a standard curve generated by contacting the population of T cells and target cells with different concentrations of purified TDB.

14. A method for determining if a population of test cells expresses a target antigen, the method comprising
   a) contacting the population of test cells with a population of T cells, wherein the T cells comprise nucleic acid encoding a reporter operably linked to a response element that is responsive to T cell activation, wherein the response element that is responsive to T cell activation is an NFκB promoter,
   b) contacting the population of T cells and test cells with a T cell dependent bispecific (TDB), wherein the TDB comprises a target antigen binding fragment and a CD3 binding fragment,
   wherein expression of the reporter indicates the presence of the target antigen expressed by the test cell.

* * * * *